United States Patent
Shows et al.

(10) Patent No.: US 7,263,411 B2
(45) Date of Patent: Aug. 28, 2007

(54) SECURE MEDICAMENT DISPENSING CABINET, METHOD AND SYSTEM

(75) Inventors: Paul Randall Shows, Pineville, LA (US); Robert Parks, Pittsburgh, PA (US); Ryan Kaintz, Pittsburgh, PA (US); Eric Lamont Holmes, Pittsburgh, PA (US); Matthew Goodworth, Pittsburgh, PA (US); Stuart Morgan, West Chester, PA (US); Matthew Stuart Beale, Pittsburgh, PA (US); Michael A. Bergeron, Pineville, LA (US); Stan Jankowski, Pittsburgh, PA (US)

(73) Assignee: Parata Systems, LLC, Morrisville, NC (US)

( * ) Notice: Subject to any disclaimer, the term of this patent is extended or adjusted under 35 U.S.C. 154(b) by 173 days.

(21) Appl. No.: 10/637,867

(22) Filed: Aug. 8, 2003

(65) Prior Publication Data

US 2004/0108323 A1 Jun. 10, 2004

Related U.S. Application Data

(60) Provisional application No. 60/402,282, filed on Aug. 9, 2002, provisional application No. 60/458,160, filed on Mar. 27, 2003.

(51) Int. Cl.
*G06F 17/00* (2006.01)

(52) U.S. Cl. .................. 700/237; 700/232; 700/236; 700/244; 221/2; 221/9

(58) Field of Classification Search .................. 221/2, 221/7, 9, 13, 131, 129; 700/237, 232, 236, 700/244
See application file for complete search history.

(56) References Cited

U.S. PATENT DOCUMENTS 4,573,606 A * 3/1986 Lewis et al. .................. 221/2

(Continued)

FOREIGN PATENT DOCUMENTS

EP 1 053 738 A2 11/2000

(Continued)

OTHER PUBLICATIONS

Baker APS, Pharmacy 2000 The Pharmacy of the Future . . . Today, marketing brochure, Automated Prescription Systems, Inc., Pineville, Louisiana and Dorval, Quebec, Canada.

(Continued)

*Primary Examiner*—Khoi H. Tran
(74) *Attorney, Agent, or Firm*—Myers Bigel Sibley & Sajovec

(57) ABSTRACT

A medicament dispensing cabinet is comprised of a frame, at least one controller, and a plurality of drawers each movably carried by the frame and each defining a plurality of dispensing cells. A plurality of removable dispensing devices is provided with each one carried by one of the dispensing cells. Each of the dispensing cells further comprises a motor for providing rotary motion to one of the removable dispensing devices in response to the controller, a sensor operating in conjunction with the controller for counting medicament dispensed from one of the removable dispensing devices, a chute for receiving medicament dispensed from one of the removable dispensing devices and a chute gate for controlling access to the chute. The cabinet may additionally comprise a chute gate release responsive to the controller for controlling the chute gate and a chute gate sensor connected to the controller and responsive to the position of the chute gate. The cabinet may be used in conjunction with a number of processes including dispensing, secure-pickup (insuring the person picking up the dispensed medicament is authorized to do so), back-end verification (verifying the identity of the person picking up the dispensed medicament), a process for removing a dispensing device from a drawer, and a process for inserting a dispensing device into a drawer.

8 Claims, 42 Drawing Sheets

U.S. PATENT DOCUMENTS

| | | | |
|---|---|---|---|
| 4,785,969 A * | 11/1988 | McLaughlin | 221/2 |
| 5,337,919 A | 8/1994 | Spaulding et al. | |
| 5,597,995 A | 1/1997 | Williams et al. | |
| 5,720,154 A | 2/1998 | Lasher et al. | |
| 5,897,024 A | 4/1999 | Coughlin et al. | |
| 5,907,493 A * | 5/1999 | Boyer et al. | 700/231 |
| 5,915,589 A * | 6/1999 | Lim | 221/3 |
| 6,073,834 A * | 6/2000 | Michael et al. | 232/43.1 |
| 6,112,502 A | 9/2000 | Frederick et al. | |
| 6,161,721 A | 12/2000 | Kudera et al. | |
| 6,343,711 B1 | 2/2002 | Coughlin | |
| 6,393,339 B1 * | 5/2002 | Yeadon | 700/237 |
| 6,510,962 B1 * | 1/2003 | Lim | 221/15 |
| 6,580,968 B1 | 6/2003 | Yuyama et al. | |
| 6,636,780 B1 * | 10/2003 | Haitin et al. | 700/236 |
| 2002/0095238 A1 | 7/2002 | Ahlin et al. | |
| 2003/0055531 A1 | 3/2003 | Liff et al. | |

FOREIGN PATENT DOCUMENTS

| | | |
|---|---|---|
| EP | 1053738 A2 | 11/2000 |
| WO | WO 00/18644 | 4/2000 |

OTHER PUBLICATIONS

Baker Cells, Standard Cabinets, marketing brochure, Automated Prescription Systems, Inc., Pineville, Louisiana and Dorval, Quebec, Canada.

The Baker Autoscript System, marketing brochure, Automated Prescription Systems, Inc., Pineville, Louisiana and Dorval, Quebec, Canada and Sl—Baker, Easton, Pennsylvania.

* cited by examiner

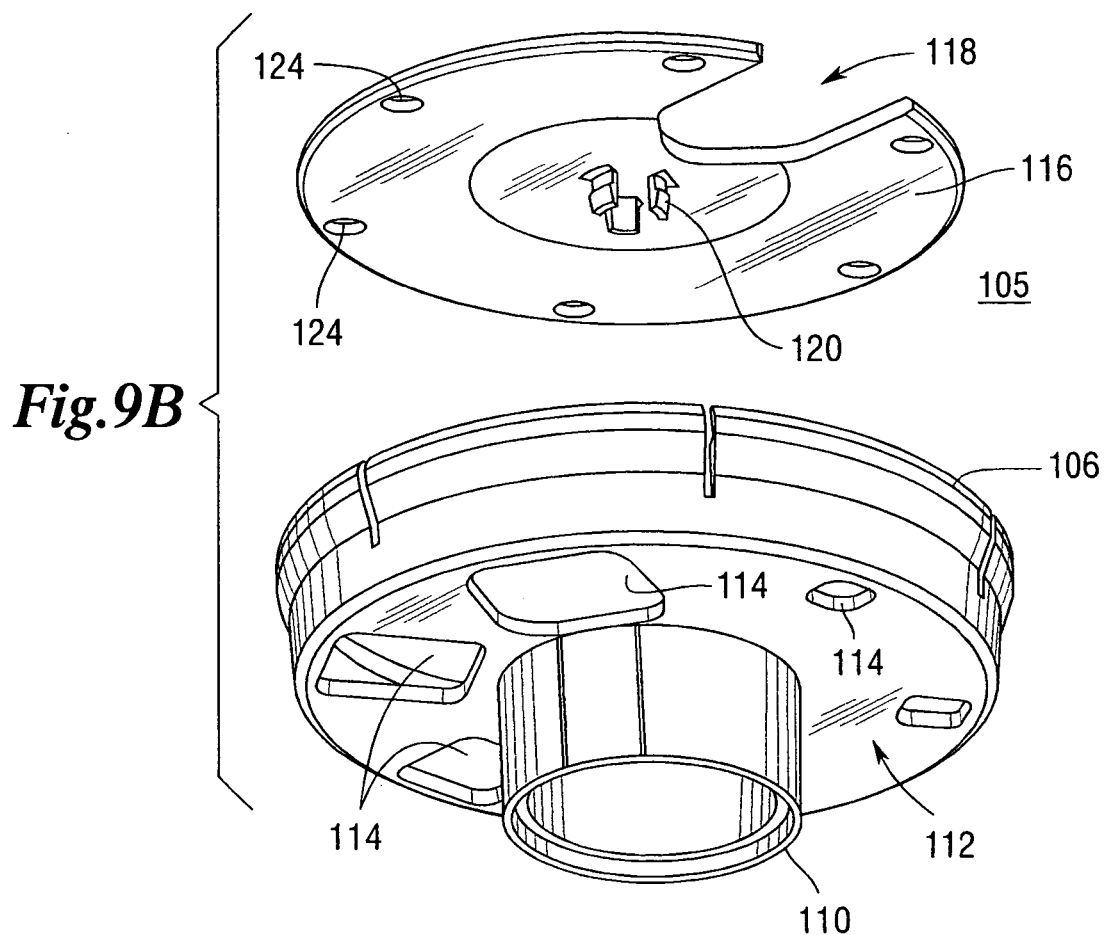
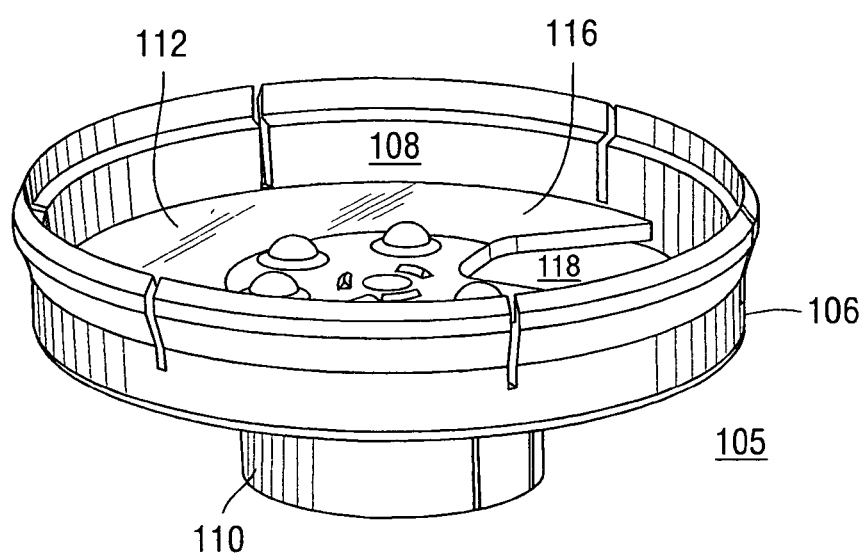

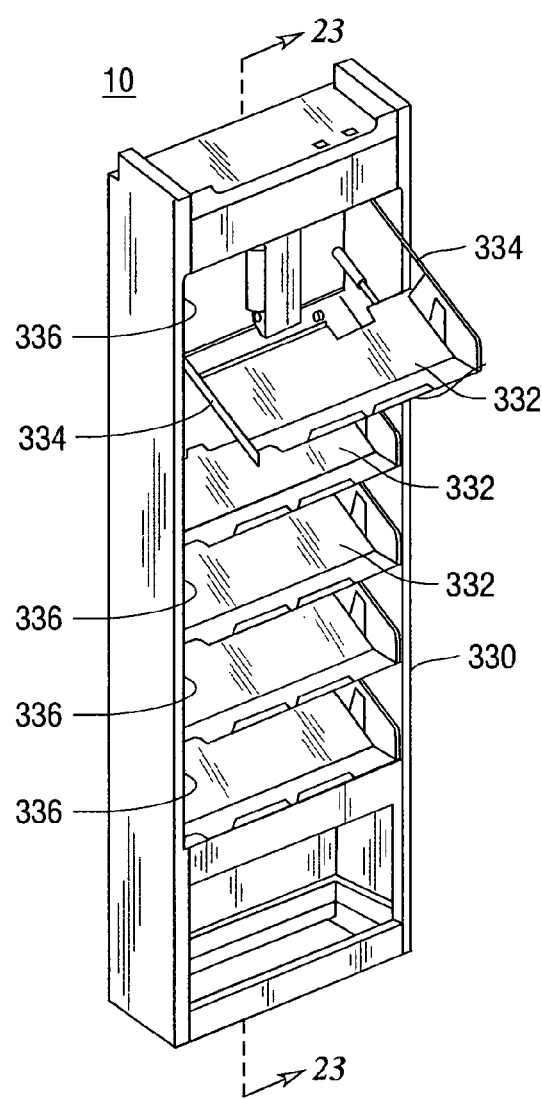
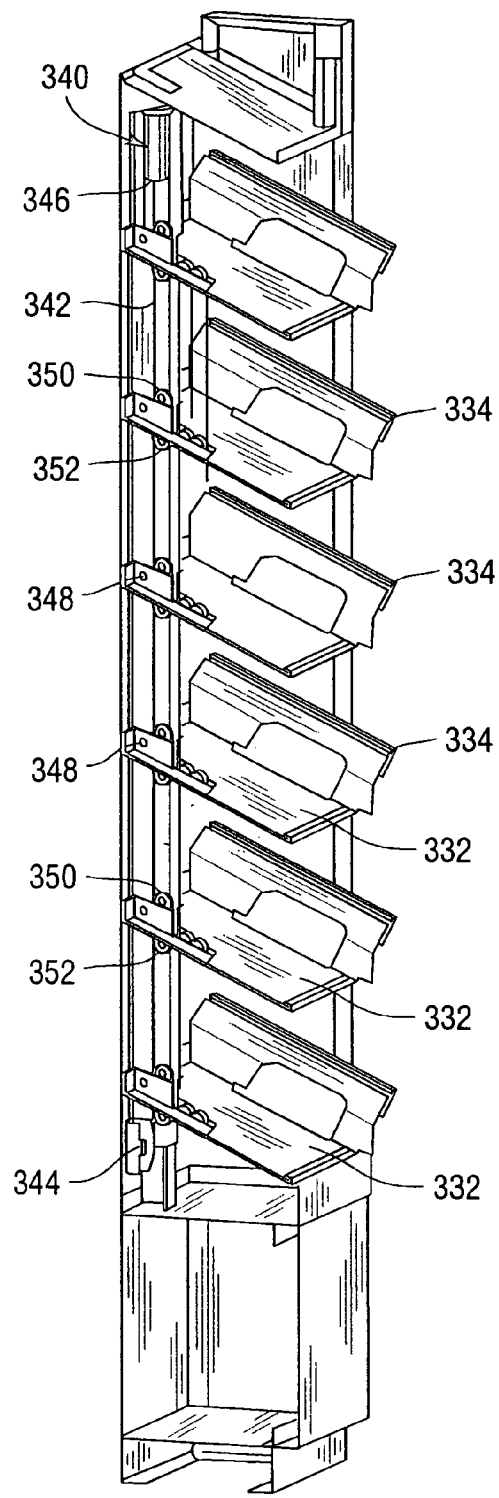
Fig.22
Fig.23

SECURE MEDICAMENT DISPENSING CABINET, METHOD AND SYSTEM

CROSS-REFERENCE TO RELATED APPLICATIONS

This application claims priority from U.S. provisional application Ser. No. 60/402,282 filed Aug. 9, 2002 entitled Drug Cartridge and Cabinet for Holding the Same, the entirety of which is hereby incorporated by reference, and U.S. provisional application Ser. No. 60/458,160 filed Mar. 27, 2003 entitled Secure Medicament Dispensing Cabinet, Method and System, the entirety of which is hereby incorporated by reference. The present application is related to U.S. application Ser. No. 10/637,775 filed herewith and entitled Dispensing Device having A storage Chamber, Dispensing Chamber and Feed Regulator Therebetween and U.S. application Ser. No. 10/637,772 filed herewith and entitled Drug Dispensing Cabinet Having A Drawer Interlink, Counterbalance And Locking System.

BACKGROUND OF THE INVENTION

The present invention is broadly concerned with using a dispenser carried in a locking drawer of a storage cabinet to insure patient prescriptions are filled with the proper medicament and the pharmacy worker replenishes and maintains the dispenser with the proper medicament while also tracking medicament inventory quantities and other medicament specific information for each patient prescription.

Over the years, the pharmacy industry has matured into an industry that dispenses medicament to patients from bulk stock bottles to keep up with the ever increasing demand of new medicaments, treatment plans and regimens, and more patients. These increased supply demands have occurred in the pharmacy industry while a significant decrease in pharmacies was occurring as a result of pharmacy consolidation and acquisitions. An ever present pressure exists within the pharmacy to reduce dispensing costs and drive down the overall cost of patient prescriptions while maintaining the highest prescription quality level and minimizing medication errors.

Medicament dispensing equipment has been employed by pharmacies to increase the pharmacy staff productivity, insure quality and reliability of prescriptions filled for patients, and drive down prescription filling costs. The primary approach used in pharmacies has been to deploy medicament dispensing equipment for the highest volume medicaments dispensed within a pharmacy. As a pharmacy's prescription volume increases, additional medicament is placed in the dispensing equipment to further reduce costs, and increase productivity of the pharmacy personnel.

This approach to deploying dispensing equipment works due to the fact that prescription dispensing is not linear across all medicaments stocked by a pharmacy. A typical pharmacy may carry approximately 1500 unique bulk medicaments that will be repackaged into smaller patient prescription quantities by the pharmacy workers. A small fraction of these bulk medicaments represent a high percentage of dispensed patient prescriptions. This allows the pharmacy to utilize automatic medicament dispensing equipment for this small fraction of the total formulary to greatly reduce the patient prescription dispensing time. By using medicament dispensing equipment, the actual patient waiting times are reduced while increasing the customer satisfaction and reducing the pharmacy labor costs.

Current medicament dispensing solutions include those produced by the assignee under the trade name of Baker Cell™ and Baker Cassette™ and shown in U.S. Pat. Nos. 4,111,332 and 4,869,394. The Baker Cell™ places each medicament in a dispenser hopper attached to a dispensing unit for use by high volume pharmacies where speed of dispensing a specific formulary is desired. The Baker Cassette™ places each medicament in a separate drug cartridge sharing a common dispensing unit and is used by low to medium volume pharmacies.

A medicament dispensing solution available from Innovation Associates, sold under the trade name of PharmAssist™ and shown in U.S. Pat. Nos. 5,907,493 and 5,884,806, places each medicament in a separate dispensing unit. The medicament container is an integral part of the dispensing unit which cannot be removed for cleaning, maintenance, or replenishment at a workstation that allows easier access to the bulk medicament stored separate from the dispensing units and to allow the other dispensing units co-located in a common drawer to be returned to an operable dispensing condition. The PharmAssist™ dispensing cell has an annunciator LED for indicating to the pharmacy technician which dispensing cell has completed its dispensing process and is ready for the pharmacy technician to retrieve. However, in a high volume pharmacy where the equipment is installed, the pharmacy must rely upon several pharmacy technicians and pharmacists to handle the workload. In these high volume pharmacies, the dispensing cell annunciator LED is inadequate to insure the correct pharmacy worker retrieves the medicament from the dispensing cell for a specific patient prescription; leading to a potential medication error.

A medicament dispensing solution available from ScriptPro, sold under the trade name ScriptPro200™ and shown in U.S. Pat. Nos. 5,897,024 and 6,161,721, places each medicament in a separate dispensing cell and uses a robotic vial manipulator and dispensing unit. The dispensing unit is brought to the dispensing cell by the robotic vial manipulator for medicament dispensing.

In today's pharmacy, the medicament dispensing systems must continue to dispense medicament while being maintained and replenished with medicament from bulk stock bottles. These dispensing systems are simultaneously operated by several pharmacy workers performing different tasks. Several pharmacy technicians and pharmacists may be using the medicament dispensing system at the same time to dispense patient prescriptions. The pharmacy inventory specialist or pharmacy technicians may be replenishing the depleted dispensing cells with medicament under the supervision of the pharmacist. Other dispensing cells may require cleaning or maintenance to insure optimal performance.

To efficiently dispense patient prescriptions, the dispensing equipment must inform the pharmacy workers of the current state of each dispensing cell. The pharmacy workers must be informed when each dispensing cell has completed the dispensing of a patient's prescription and clearly identify which pharmacy worker should retrieve the medicament from the dispensing cell. Likewise, the pharmacy workers must be informed when the drug cartridge or dispensing cell requires maintenance that may occur while operating, or due to cleaning intervals based on a prescribed time interval or quantity of medicament dispensed by the dispensing cell.

The present medicament dispensing systems are limited in their ability to operate in pharmacies requiring each patient prescription retrieved from the dispensing unit to be verified and recorded as to the pharmacy worker performing the operation. These medicament dispensing systems lack the ability to operate efficiently when utilized by several pharmacy workers retrieving patient prescriptions from the dispensing unit or when replenishing or maintaining the dispensing cells because the medicament dispensing system must restrict access to a single dispensing cell at a time to insure the pharmacy worker access.

The present medicament dispensing systems do not include a method of operating the medicament dispensing equipment to insure proper replenishment from bulk medicament in stock bottles by an authorized pharmacy worker while tracking the medicament specifics for batch information, lot number and expiration dates.

The dispensing equipment must insure it is properly replenished with medicament by the pharmacy worker as directed by the dispensing computer. The dispensing computer must record and verify the pharmacy worker, drug cartridge, and bulk medicament specifics to insure the proper medicament is poured from the bulk medicament stock bottle into the drug cartridge.

The dispensing computer must provide a process of verification and authentication to insure the drug cartridge is replenished with the proper bulk medicament and restrict the replenishment to authorized personnel only. The dispensing computer should provide a product verification step that allows the pharmacist to delegate the inventory and replenishment tasks to a trained pharmacy technician while knowing that accidental replenishment mistakes will be detected and the dispensing computer will then prevent further prescription filling from the dispensing cell and drug cartridge until the problem has been corrected by the pharmacist.

BRIEF SUMMARY OF THE INVENTION

The present invention is directed to a medicament dispensing cabinet comprising a frame, at least one controller, and a plurality of drawers each movably carried by the frame and each defining a plurality of dispensing cells. A plurality of removable dispensing devices is provided with each one carried by one of the dispensing cells. Each of the dispensing cells further comprises a motor for providing rotary motion to one of the removable dispensing devices in response to the controller, a sensor operating in conjunction with the controller for counting medicament dispensed from one of the removable dispensing devices, a chute for receiving medicament dispensed from one of the removable dispensing devices and a chute gate for controlling access to the chute. The cabinet may additionally comprise a chute gate release responsive to the controller for controlling the chute gate and a chute gate sensor connected to the controller and responsive to the position of the chute gate.

Other embodiments of the invention include providing each drawer with an electronically controlled lock responsive to the controller, a drawer position sensor connected to the controller and responsive to the position of the drawer, and a drawer release switch operable by a user and connected to the controller. Each dispensing device may additionally comprise a lid, and wherein each dispensing cell additionally comprises a dispensing device sensor connected to the controller and responsive to the presence or absence of the lid from its home position.

Each dispensing cell may additionally comprise a cell display responsive to the controller for providing various information to a user. Each dispensing cell may additionally carry a machine readable indicia and wherein each removable device also carries a machine readable indicia for use in various methods such as restocking, servicing, etc.

Other embodiments of the present invention include providing a counterbalance, and wherein each of the drawers is responsive to the counterbalance such that only one drawer can be fully open at a time. The drawers may be carried by drawer glides mounted at an angle with respect to the frame.

The present invention is also directed to various methods of operation including dispensing an amount of medicament into a chute, inputting information identifying a person requesting access to the dispensed medicament, determining if the person requesting access may pick up the dispensed medicament, and selectively releasing a chute gate in response to the determining. The process of determining may include determining if the person requesting access is the same as the person initiating the dispensing or if the person has authority to pick up medicament for the person initiating the dispensing. The method may additionally comprise inputting information identifying the person picking up the dispensed medication after the medicament has been picked up and/or inputting information identifying the dispenser which has performed the dispensing.

Another method of the present invention comprises identifying a dispenser which requires service, inputting user information, determining if the user has authority to access all dispensers in the drawer carrying the dispenser requiring service and, if so, issuing an unlock command for the drawer carrying the dispenser requiring service. The process further comprises awaiting receipt of a signal from a drawer unlock switch and, upon receipt of that signal, monitoring a dispensing device switch to insure that the dispenser requiring service is the dispenser removed or accessed (e.g., the lid is opened). Finally a drawer position switch is monitored to determine when the drawer is closed. The service may include cleaning, stocking, and maintenance.

Another method of the present invention comprises identifying a dispenser which requires insertion into a drawer, inputting user information, determining if the user has authority to access all dispensers in the drawer into which the dispenser is to be inserted and, if so, issuing an unlock command for the drawer. The process further comprises awaiting receipt of a signal from a drawer unlock switch and, upon receipt of that signal, monitoring a dispensing device switch to insure that the dispenser is inserted into the proper position. Finally a drawer position switch is monitored to determine when the drawer is closed.

BRIEF DESCRIPTION OF THE DRAWINGS

For the present invention to be easily understood and readily practiced, the present invention will now be described, for purposes of illustration and not limitation, in conjunction with the following figures, wherein:

FIG. 9B is an exploded, perspective view from the bottom of the feed regulator;

FIG. 9C is a perspective view from the top of the feed regulator;

FIG. 22 is a perspective view of the dispensing cabinet of FIG. 1 with the drawers and doors removed;

FIG. 23 is a sectional view of the cabinet taken along the lines III-III in FIG. 22;

FIG. 45 is a flow chart illustrating the back end verification procedure shown in FIG. 42.

DETAILED DESCRIPTION OF THE INVENTION

Figure 1:
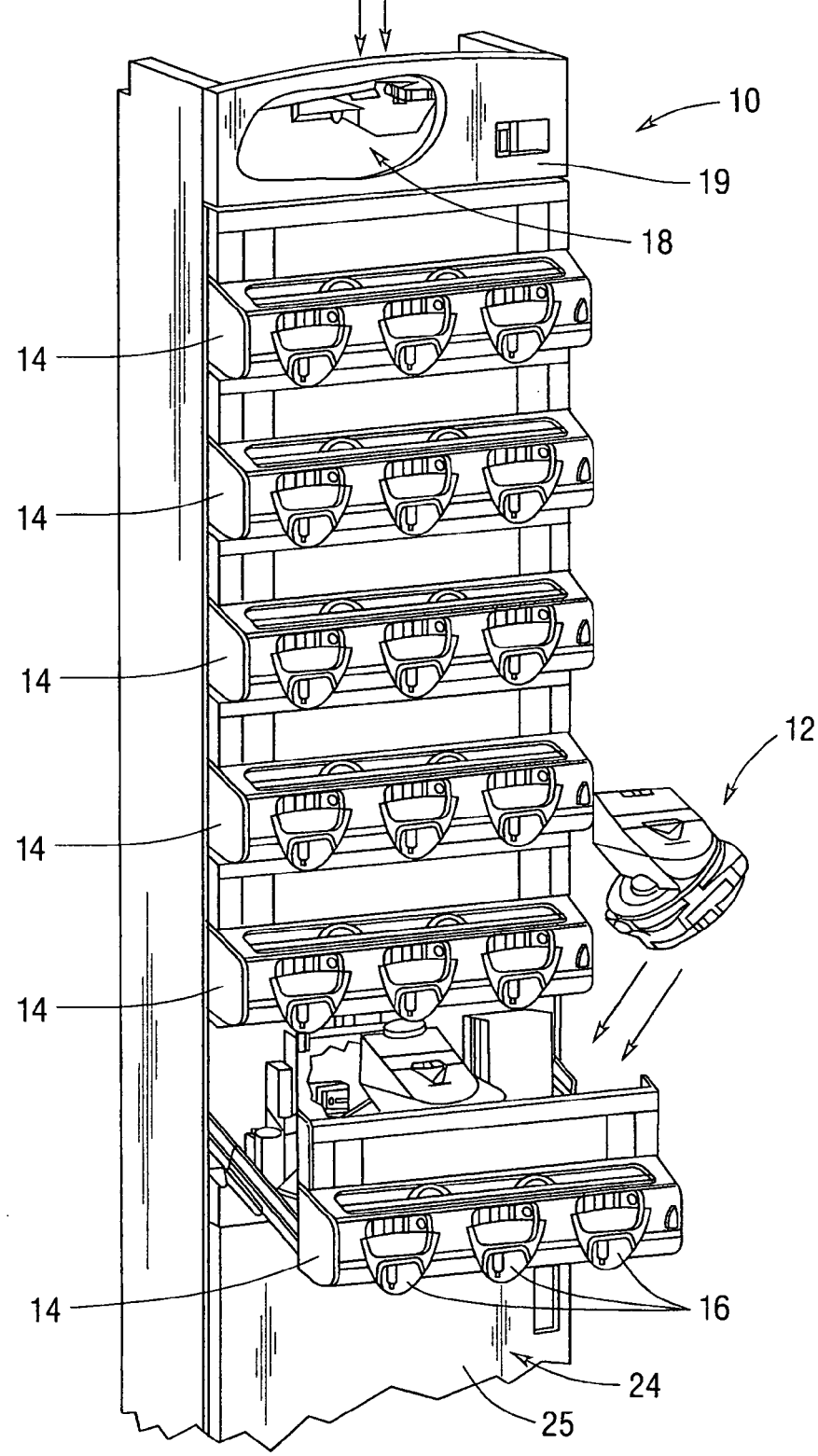
FIG. 1 is a front perspective view of a medicament dispensing cabinet.

FIG. 1 illustrates a front view of a medicament dispensing cabinet 10 in which a dispensing device 12 of the present invention may be used. The medicament dispensing cabinet 10 is comprised of a plurality of dispensing drawers 14 each containing three dispensing cells 16. Each dispensing cell 16 is comprised of certain electrical and mechanical components (described below) carried by the drawers 14, which cooperate with a dispensing device 12. Each dispensing cell 16 and dispensing device 12 form one type of dispenser although any type of dispenser, such as a Baker Cell, may be carried by drawers 14. It should be apparent to those skilled in the art that the construction of the medicament dispensing cabinet 10 may be modified to contain fewer or more dispensing drawers 14 to meet different requirements. Also, each dispensing drawer 14 may be constructed to contain fewer than three dispensing cells 16 or more than three dispensing cells 16. Each medicament dispensing cabinet 10 contains a cabinet controller 18 contained behind a door 19. The cabinet controller 18 is connected to a dispensing computer, filling workstation, embedded controller, or other control device by an interface cable 20 or by a radio frequency connection used in conjunction with a device such as a PDA (not shown in FIG. 1). Whenever the term "computer", "workstation" or the like is used in this document it should be broadly construed to mean any appropriate type of control device. Additional medicament dispensing cabinets 10 may be connected to the dispensing computer or filling workstation by an interconnect cable 22 connected between successive medicament dispensing cabinets 10 to form a medicament dispensing cabinet system. All medicament dispensing cabinets 10 may be controlled by the common dispensing computer or filling workstation. A storage area 24 is located in the medicament dispensing cabinet 10 behind a door 25 for storing bulk medicament stock bottles, alternative removable dispensing devices 12, or other materials or inventory.

Figure 2A:
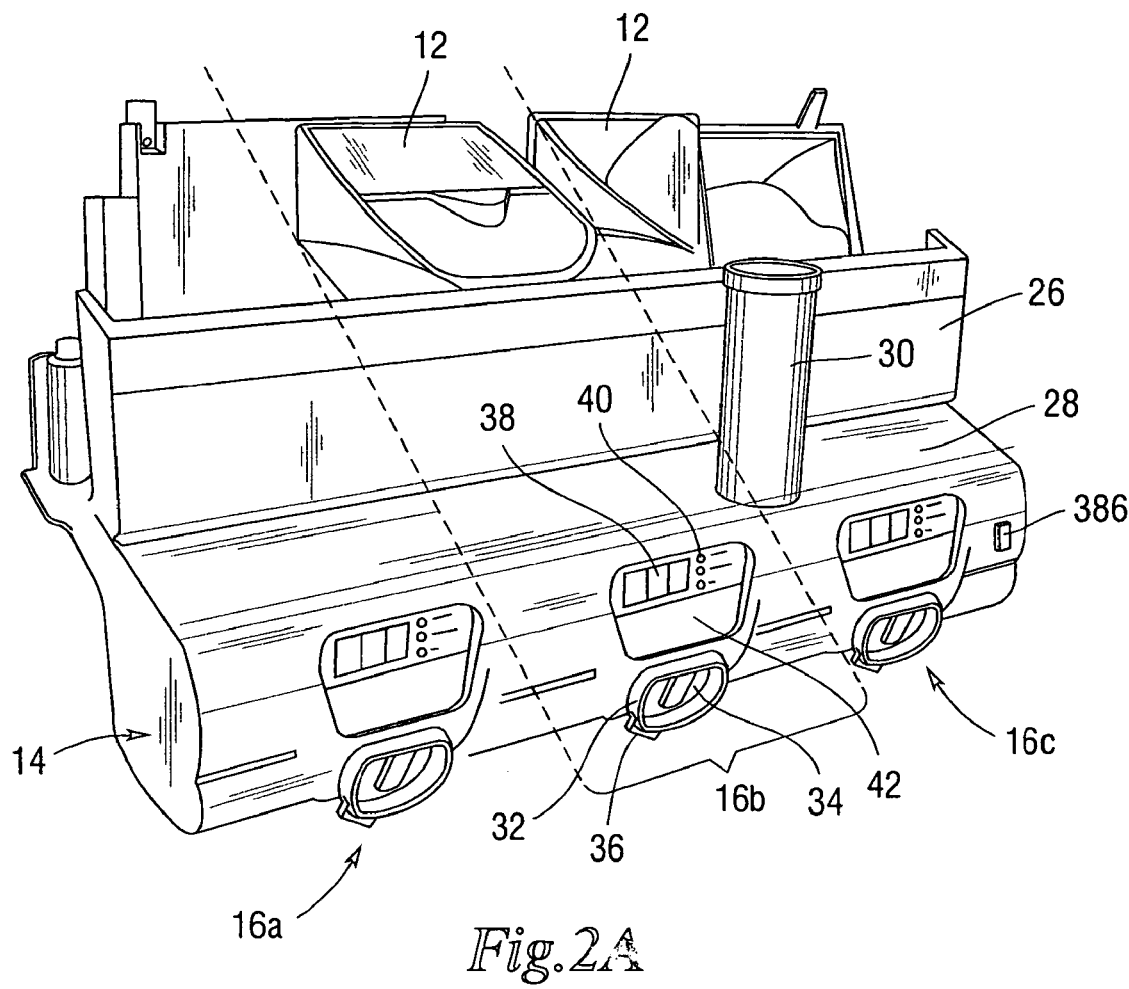
FIG. 2A is a left-front perspective view of a medicament dispensing drawer with the far left dispensing device removed and the lid opened on the far right dispensing device.

FIG. 2A shows a front-left view of the dispensing drawer 14 (all dispensing drawers 14 being of a similar construction). In the present embodiment, each dispensing drawer 14 is comprised of three dispensing cells 16a, 16b, 16c and a drawer controller 46 (see FIG. 3B). Each dispensing cell 16 contains a removable dispensing device 12 filled with medicament (not shown in FIG. 2A). In FIG. 2A, the removable dispensing device 12 has been removed from the left most dispensing cell 16a while the removable dispensing device 12 in the right most dispensing cell 16c is shown in an opened condition (for restocking). Each dispensing drawer 14 may also comprise an instruction fascia panel 26, a ledge 28 for temporarily holding a prescription vial 30 or bulk medicament stock bottle (not shown). The dispensing drawer's ledge 28 may be used by the pharmacy worker to temporarily place empty or full prescription vials 30 while dispensing medicament from another dispensing cell 16 into another prescription vial 30.

Figure 2C:
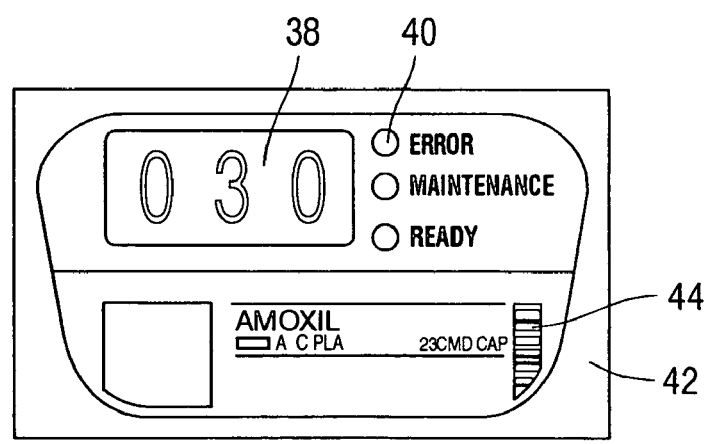
FIG. 2C illustrates details of a display, annunciator and a cell label.
Figure 2B:
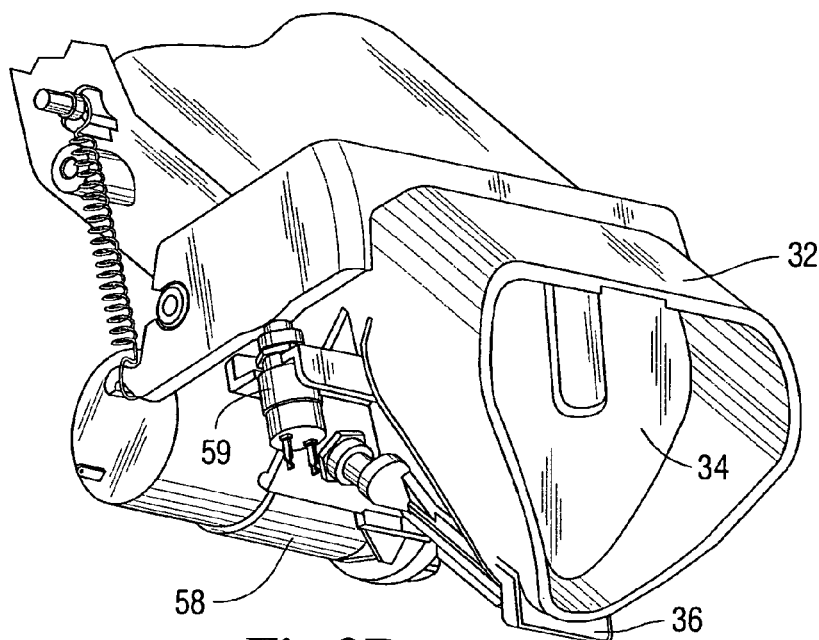
FIG. 2B illustrates details of the chute, chute gate, and gate release.

Each dispensing cell 16 includes a chute 32, chute gate 34 and gate release 36, as shown in FIG. 2B. Each dispensing cell 16 also includes a cell display 38, annunciators (e.g. LEDs) 40 and a cell label 42 as shown in FIG. 2C. In the present embodiment, the cell display 38 consists of three alpha-numeric digits for displaying information to the pharmacy worker while the dispensing cell 16 is operating. It should be apparent to those skilled in the art that the cell display 38 may include additional characters, symbols, pictures, etc. to better communicate with the pharmacy worker. It should also be apparent to those skilled in the art that the techniques to display information on the cell display 38 may be varied by the drawer controller in such a manner as to effectively display more than three characters of information to the pharmacy worker. The information display techniques may include alternating between multiple message segments consisting of three characters, scrolling a message from left to right through the three digits, or changing the intensity of the display characters while either alternating or scrolling the message.

The annunciator LEDs 40 provide immediate status information to the pharmacy worker about the current state of the dispensing cell 16 or dispensing device 12. In the present embodiment, the dispensing cell 16 comprises three different annunciators 40 with each annunciator representing a single state when illuminated. In the present embodiment, the annunciators 40 represent the dispensing cell states of 'READY', 'MAINTENANCE' and 'ERROR'. Multiple annunciators 40 may be illuminated at any moment in time. In the present embodiment, the annunciators 40 are implemented using independent LEDs. It should be apparent to those skilled in the art that the annunciators 40 may also be implemented using incandescent light bulbs integrated into the cell display, or implemented with display icons on the cell display 38 which may or may not comprise a backlight that may be provided by various light sources. Likewise, it should be apparent that additional annunciators 40 may be added to the dispensing cell 16 to present other information to the pharmacy worker. The cell display 38 and annunciators 40 are connected to and controlled by the drawer controller 46 (shown in FIG. 29).

The cell label 42 is attached to the front of each dispensing cell 16 and provides a visual and a machine readable representation, i.e., bar code indicia 44, of the medicament contained in the removable dispensing device 12 of the dispensing cell 16. In the alternative, a display that presents a picture of the product, a sample of the product or a barcode, may be used. The dispensing cell bar code indicia 44 uniquely identifies the dispensing cell 16 to the dispensing computer or other system components for purposes discussed below. The cell label 42 also contains textual information representing the medicament in the removable dispensing device 12. This textual information identifies the medicament to the pharmacy worker and may comprise one or more of the following: a drug number (i.e. either a U.S. National Drug Code (NDC) or Canadian Drug Identification Number (DIN)), a drug name, a generic drug name, a drug strength and dosage form, a manufacturer and a distributor, among others, which represents some or all of the same textual information shown on a bulk medicament stock bottle used to fill dispensing device 12. The cell label 42 may also comprise textual information representing a unique drug identification number (e.g., NDC or pharmacy generated ID) to create a unique representation for a medicament that may be supplied under the same drug number but having several different physical representations due to different manufacturers, size variations, color variations or imprints, among others. The cell label 42 may further comprise a photographic image or illustration of the medicament to allow the pharmacy worker a visual means to verify the medicament dispensed from the removable dispensing device 12 and dispensing cell 16.

The cabinet controller 18 (See FIG. 1) is connected to the drawer controller 46 (See FIG. 3B) located in each drawer 14 by an electrical or optical cable or any wireless means to communicate instructions and data. The cabinet controller 18 receives instructions from the dispensing computer or filling workstation and determines the appropriate drawer controller 46 and dispensing cell 16. The instructions or data are then forwarded to the appropriate drawer controller 46 by the cabinet controller 18 for further processing. After the drawer controller 46 has executed the instruction or processed the data, the drawer controller 46 responds to the cabinet controller 18. The cabinet controller 18 in turn responds to the dispensing computer or other control device. While the cabinet controller 18 and drawer controllers 46 are described as separate components, it should be apparent to those skilled in the art that the cabinet controller 18 and drawer controller 46 may be combined in various ways, and with functions shifted among them. Additionally, duplicate components are also intended to be within the scope of the present invention. For example, each dispensing cell 16 may consist of its own controller connected to the cabinet controller 18 or directly to the dispensing computer or other control device.

Figure 3A:
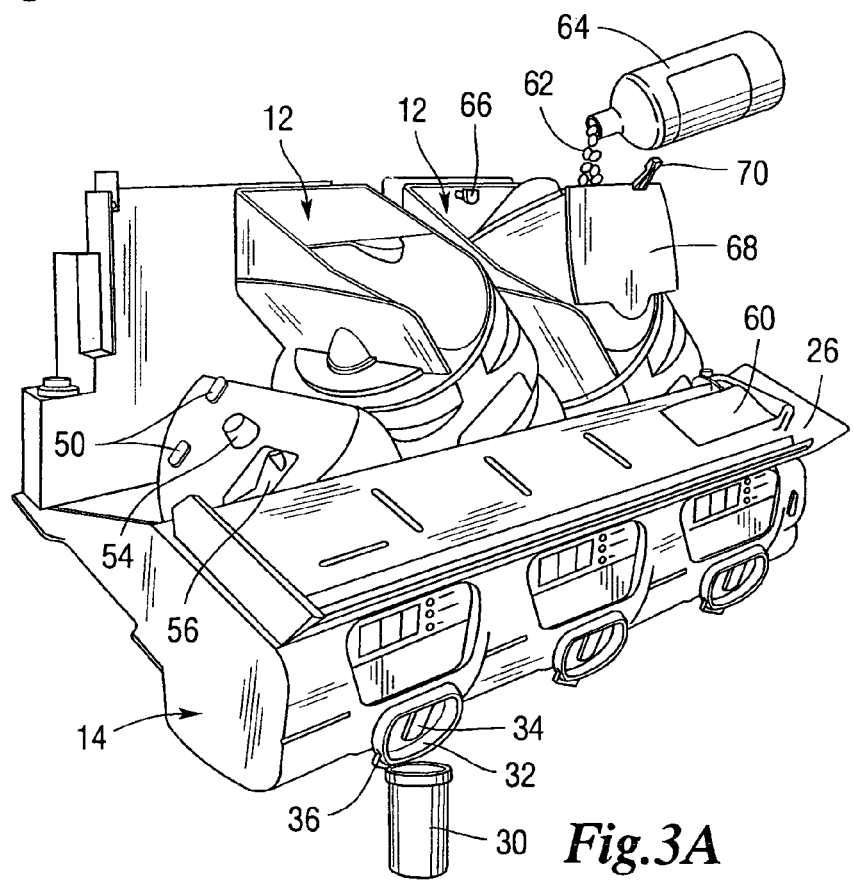
FIG. 3A is a left-front perspective view of the medicament dispensing drawer as shown in FIG. 2 with the instructional fascia panel in the open position.

FIG. 3A is a left-front perspective view of a dispensing drawer 14 with the instruction panel 26 lowered to provide easier access when removing the removable dispensing devices 12 from the dispensing cell 16. Also, the removable dispensing device 12 has been removed from the first dispensing cell 16a. Each dispensing cell 16 further comprises a pair of alignment sockets 50 that mate with alignment pins (discussed below) on the removable dispensing device 12 to properly orient and center the removable dispensing device 12 onto the dispensing cell 16. Those of ordinary skill in the art will recognize that other devices for alignment may be used while remaining within the scope of the invention. A motor drive block 54 (See FIG. 3C) driven by a motor 55 (See FIG. 3B) engages a hopper disk (discussed below) located within the removable dispensing device 12 which is rotated to dispense medicament from the removable dispensing device 12. The motor drive block may be allowed to "float" to allow for misalignment. As the motor drive block 54 and hopper disk rotate, the medicament falls from the dispensing device 12 through a dispensing cell drop out opening 56 and passes in front of a medicament sensor 57 (See FIG. 3C). As the medicament passes in front of the medicament sensor 57, the medicament is counted by the drawer controller 46. The dispensed medicament is temporarily stored in the dispensing cell's chute 32 awaiting retrieval by the pharmacy worker.

Once the medicament is dispensed into the chute 32, the pharmacy worker may release the medicament into the prescription vial 30 by pressing the gate release 36 which will actuate a gate actuator 58 thus opening the chute gate 34 allowing the medicament to fall into the prescription vial 30. The gate actuator 58 slowly opens the chute gate 34 to prevent the medicament from spilling over the top of the prescription vial 30. A gate open sensor 59 provides feedback to the drawer controller 46 to indicate the current position of the chute gate 34, which may simply be an 'open' or 'closed' indication. When the gate release 36 is activated, the drawer controller 46 will close the chute gate 34 by operating the gate actuator 58 until the gate open sensor 59 indicates the chute gate 34 has returned to the closed position. The chute gate 34 may be composed of a flexible material to seal the lower end of the chute 32 to prevent any medicament from escaping while being dispensed from the removable dispensing device 12. The flexible gate material prevents very small medicaments from escaping from the chute 32 while being dispensed. In the present embodiment, the gate actuator 58 may be comprised of a motor and cam which lifts the chute gate 34. It should be apparent to those skilled in the art that other means may be used to lift or slowly open the chute gate 34, to thereby open the lower end of the chute 32 to allow medicament to fall from the chute 32 into an awaiting prescription vial 30 or other container. For example, an electric solenoid may be used to open the chute gate 34. The electric solenoid could have either a linear or rotary motion when actuated.

Referring to FIG. 3A, the interior surface of the instruction panel 26 comprises tabs and slots for the pharmacy worker to insert a medicament lot card 60 to record the medicament 62 provided by stock bottle 64 and contained in the removable dispensing device 12. A pharmacy worker, inventory clerk, or pharmacist, among others, may record date, time, worker initials and other comments while performing routine maintenance on each dispensing cell 16 or removable dispensing device 12. The medicament specific information (e.g. lot number and expiration date) from the bulk medicament stock bottle 64 may also be recorded by the workers.

The dispensing cell 16 further comprises a dispensing device switch 66 (see also FIG. 29) which is actuated when the removable dispensing device 12 is inserted and its lid 68 is in the closed position. The lid 68 of the removable dispensing device 12 contains a tab 70 that mechanically actuates the switch 66. Likewise, the tab 70 will de-activate the switch 66 when either the lid 68 is opened or the removable dispensing device 12 is removed from the dispensing cell 16. It should be apparent to those skilled in the art that the switch 66 and tab 70 may be implemented in other ways so as to provide information as to the state of the removable dispensing device 12 being inserted into the dispensing cell 16 or the lid 68 being in the open position. For example, an optical or magnetic sensor could replace the mechanical switch 66 shown in the present embodiment to detect when the removable dispensing device 12 is inserted or its lid 68 is in the open position.

Figure 4:
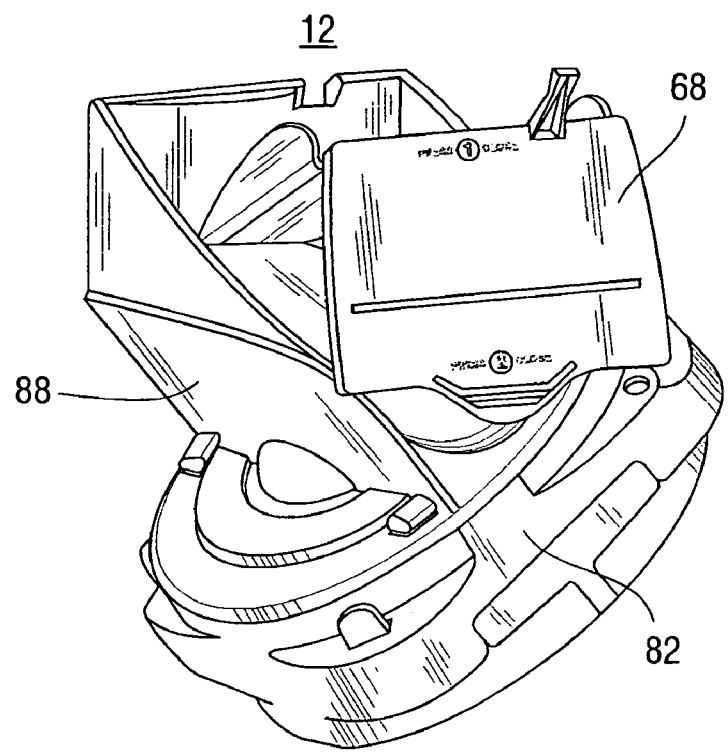
FIG. 4 is a perspective view from the top of one embodiment of the dispensing device of the present invention with its lid opened.
Figure 5:
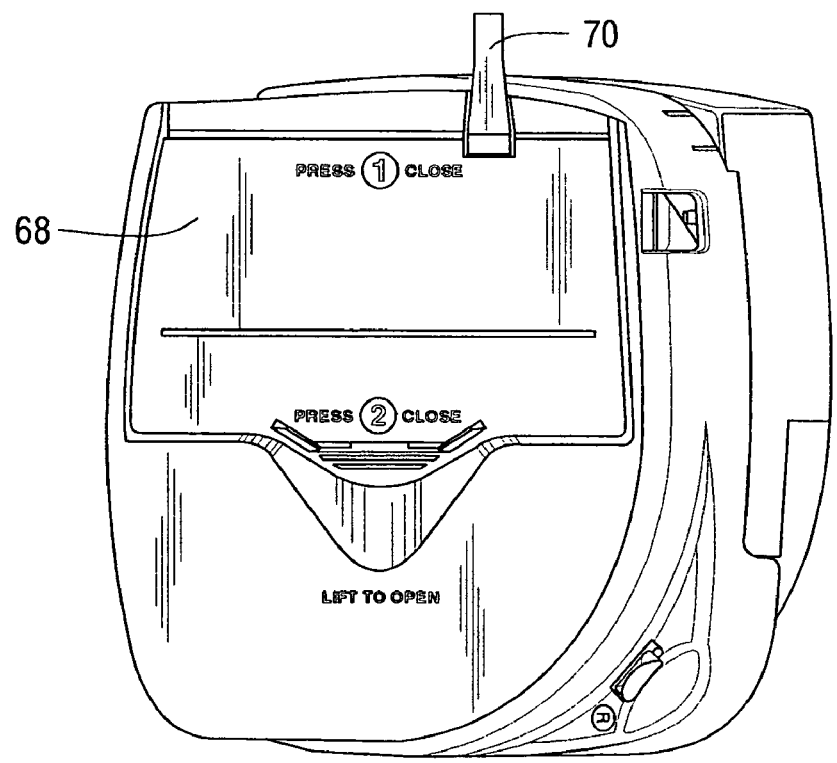
FIG. 5 is a top view of the dispensing device shown in FIG. 4.
Figure 6:
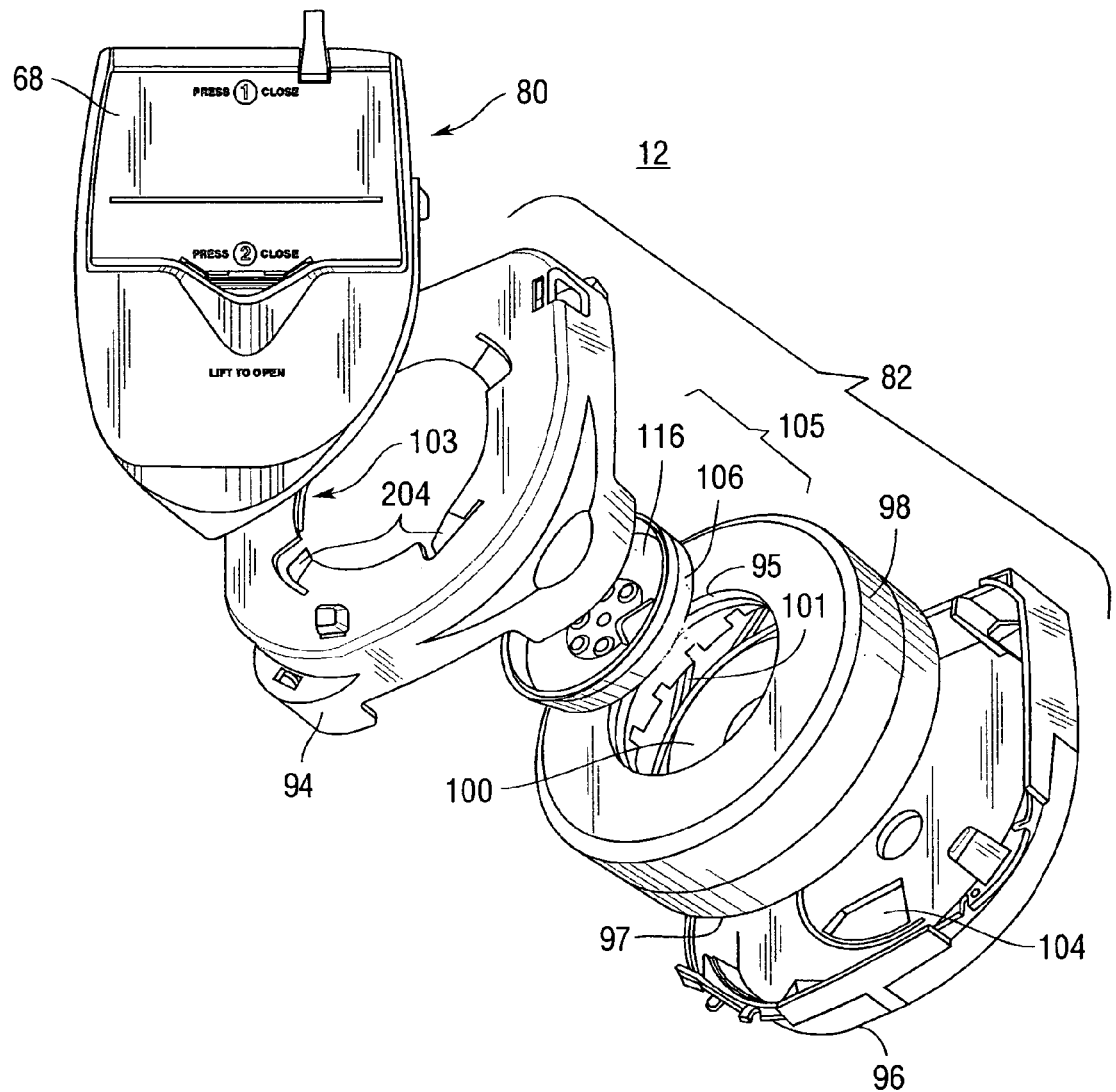
FIG. 6 is an exploded view of the dispensing device of FIG. 4.
Figure 7:
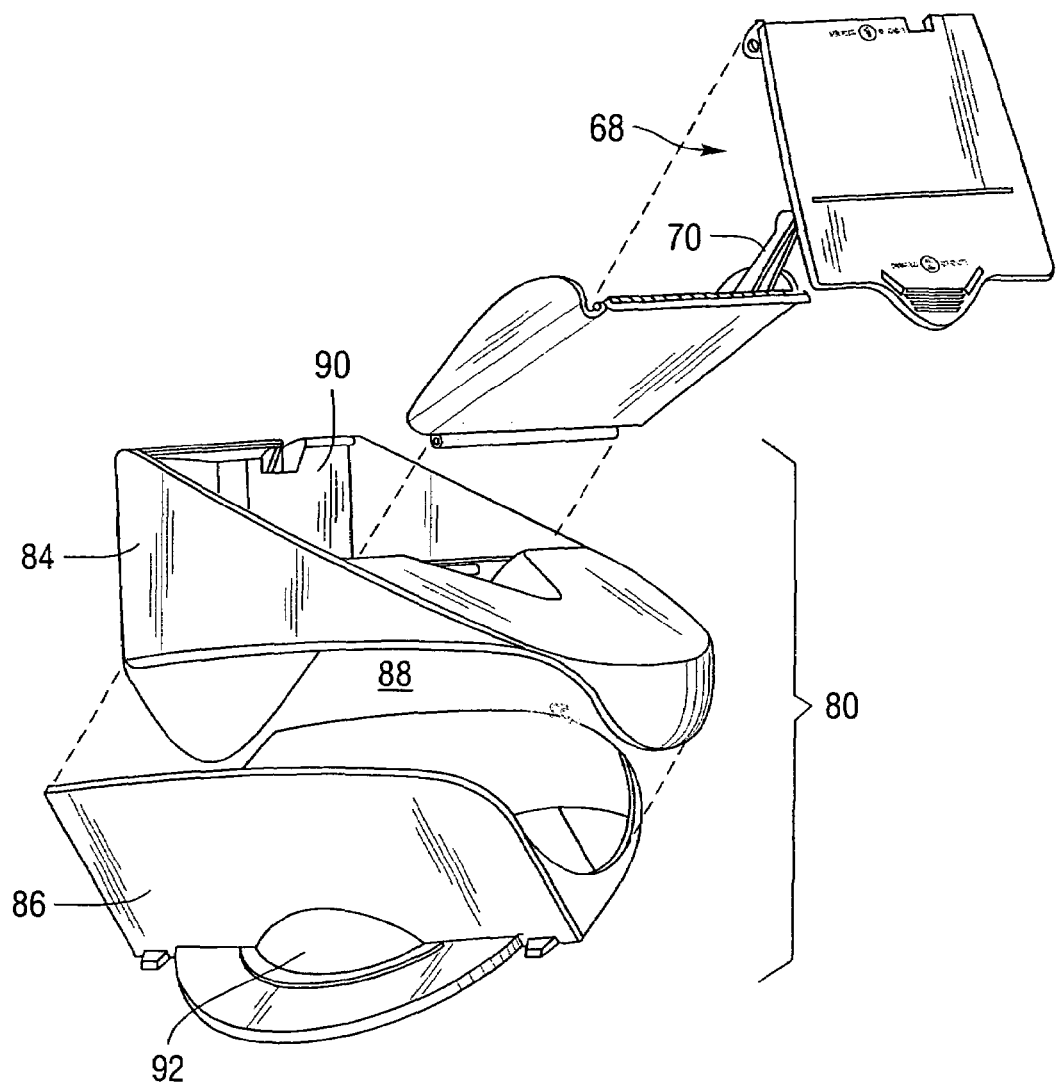
FIG. 7 is an exploded view of the upper hopper and lid.

One embodiment of a dispensing device 12 will now be described in conjunction with FIGS. 4 through 11. In FIG. 4, the dispensing device 12 is shown as being comprised of an upper hopper 80 and a lower hopper 82. Positioned between the upper hopper 80 and lower hopper 82 is a regulator (not visible in FIG. 4), sometimes referred to as a feed regulator, as will be described in detail below. FIG. 5 is a top view of the embodiment of the dispensing device illustrated in FIG. 4 while FIG. 11 is a bottom view of the dispensing device 12 illustrated in FIG. 4. FIG. 6 is an exploded view of the dispensing device 12 illustrated in FIG. 4. FIG. 7 is an exploded view of the upper hopper 80 and lid 68 and FIG. 10 is a cross-sectional view of the dispensing device 12 illustrated in FIG. 4.

Figure 10:
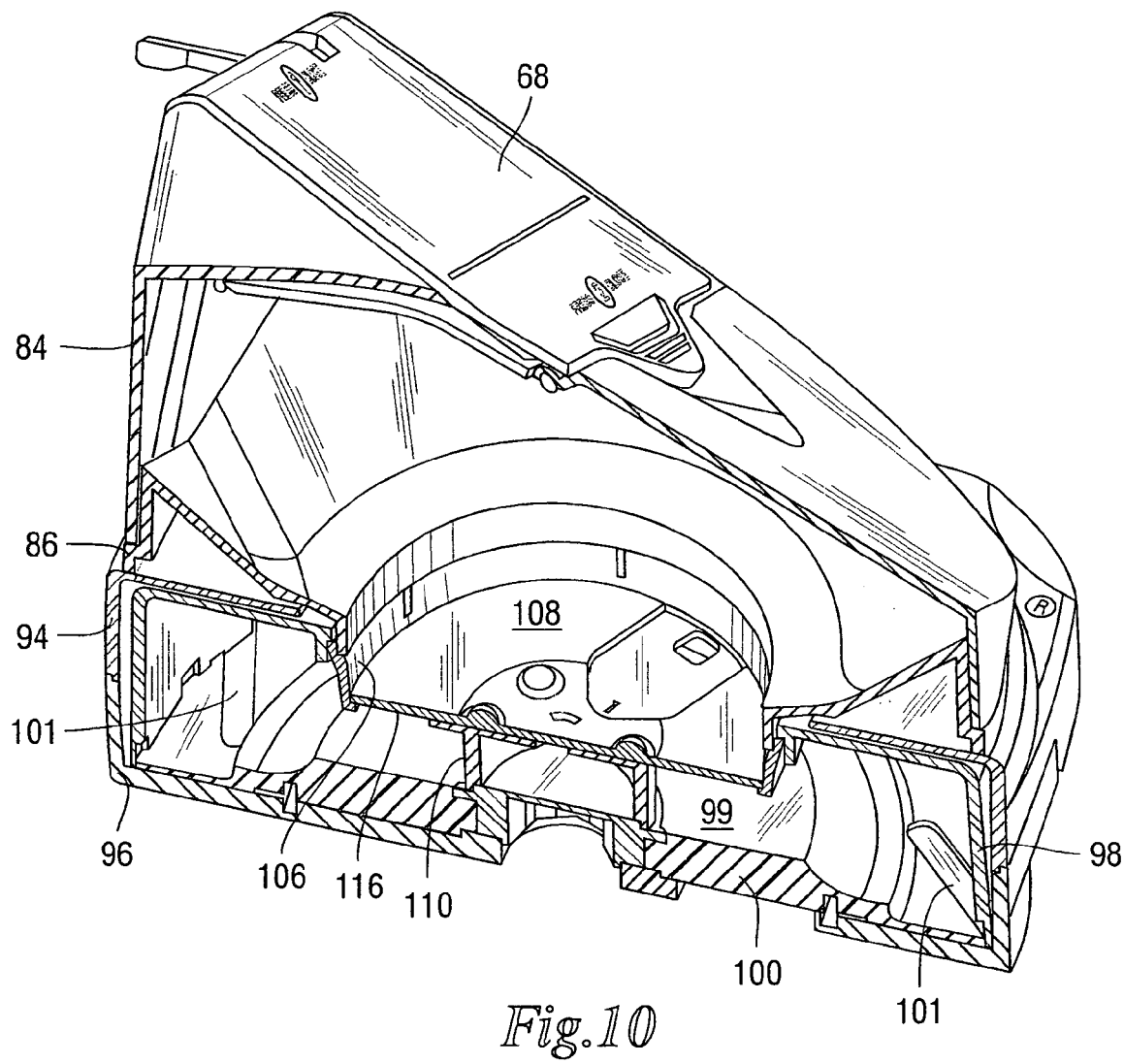
FIG. 10 is a cross sectional view of the embodiment of the dispensing device of FIG. 4.
Figure 11:
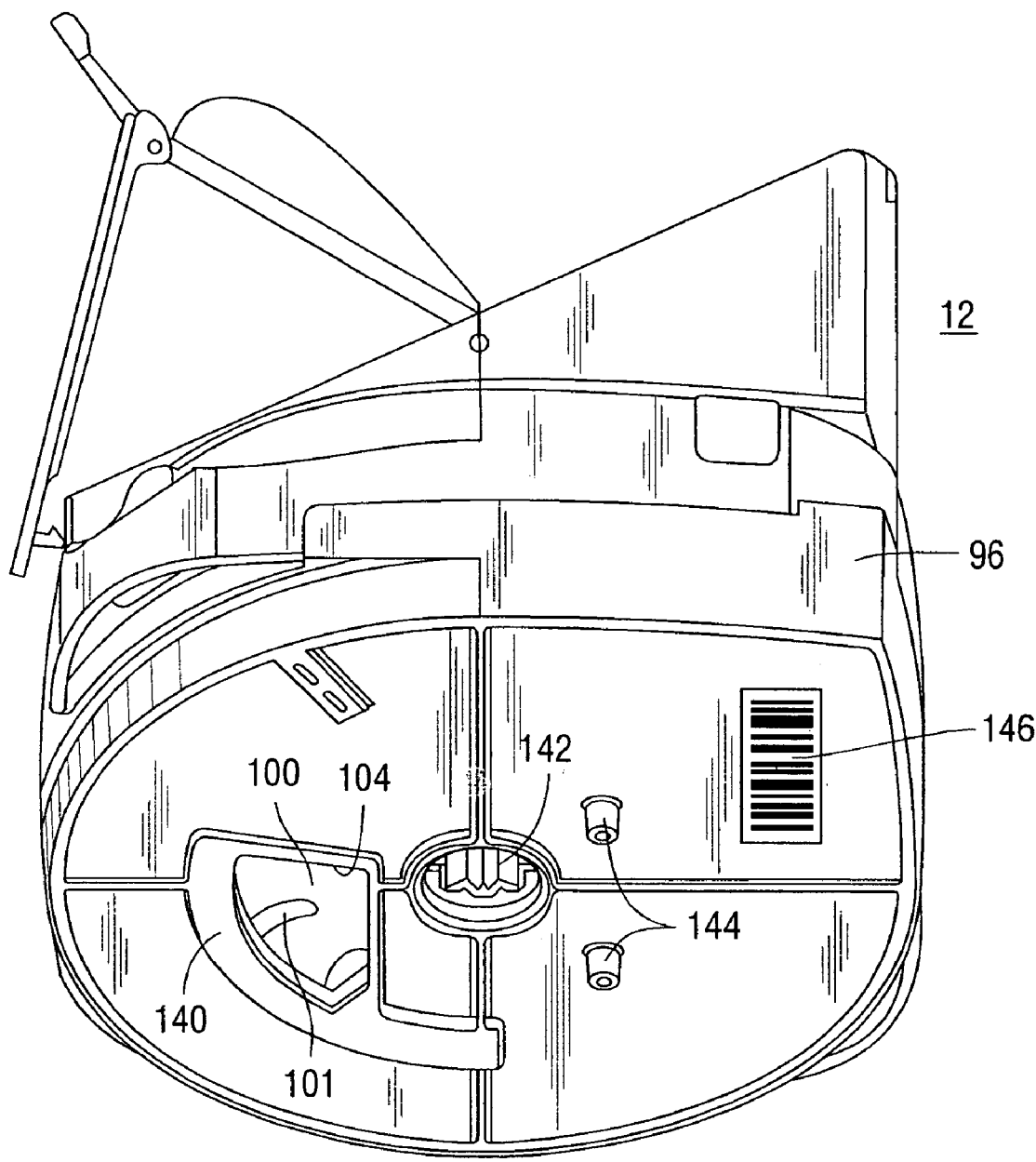
FIG. 11 is a perspective view from the bottom of the dispensing device of FIG. 4.

Turning now to FIGS. 6, 7 and 10, it will be seen that the upper hopper 80 may be comprised of two components, an upper component 84 and a lower component 86 which, when combined define an upper hopper chamber 88. The upper hopper 80 has an upper opening 90, which may be opened or closed depending upon the position of the lid 68, and a lower opening 92. The upper component 84 and the lid 68 may cooperate such that when the lid 68 is opened, a chute is formed to enable easy filling of the upper chamber 88. The upper hopper chamber 88 is sized to form a bulk storage area for storing a plurality of medicament and may have a volume on the order of 280 drams. The specific components used to form the upper hopper 80 are not important. The significance of the upper hopper 80 is to form the upper chamber 88 which is used for bulk storage of medicament.

In FIG. 6, it is seen that the lower hopper 82 is comprised of an upper platform 94 and a lower platform 96 for containing the various other components comprising the lower hopper 82. Those components include a lower hopper shell 98 having an upper opening 95 and a lower opening 97. Positioned within lower opening 97 is a rotating dispensing disc 100. The lower hopper shell 98 defines a dispensing chamber 99 (see FIG. 10) which defines the capacity of the lower hopper 82. The dispensing disc 100 is rotatable and has a plurality of grooves 101 formed therein, seen partially in FIG. 6 and FIG. 10. The lower hopper shell 98 and dispensing disc 100 are connected as shown in FIG. 8 to form a hopper disc assembly 102.

A feed regulator 105, which in this embodiment is contained within but is not a part of lower hopper 82, is positioned between the upper chamber 88 and dispensing chamber 99 defined by the lower hopper shell 98 as will be described. It should be noted, however, that although the feed regulator in this embodiment is contained within lower hopper 82, in other embodiments, the feed regulator may extend from the bottom of upper hopper 80, or may be a separate component interposed between upper hopper 80 and lower hopper 82. The purpose of the feed regulator is to regulate the rate at which medicament passes from upper hopper 80 into the dispensing chamber 99 defined by the lower hopper shell 98, and to insure a minimum continuous flow between upper hopper 80 and dispensing chamber 99, assuming capacity is available in the dispensing chamber 99 which is more likely the case during operation. Also, the specific components used to form the lower hopper 82 are not important. The significance of the lower hopper is to form the dispensing chamber 99 proximate to the dispensing disc 100.

In FIG. 6, it will be seen that the lower hopper shell 98 together with the upper platform 94 define an upper opening 103 into chamber 99. Lower platform 96 defines a lower opening 104 through which medicament dispensed by dispensing disc 100 may exit dispensing device 12.

Figure 8:
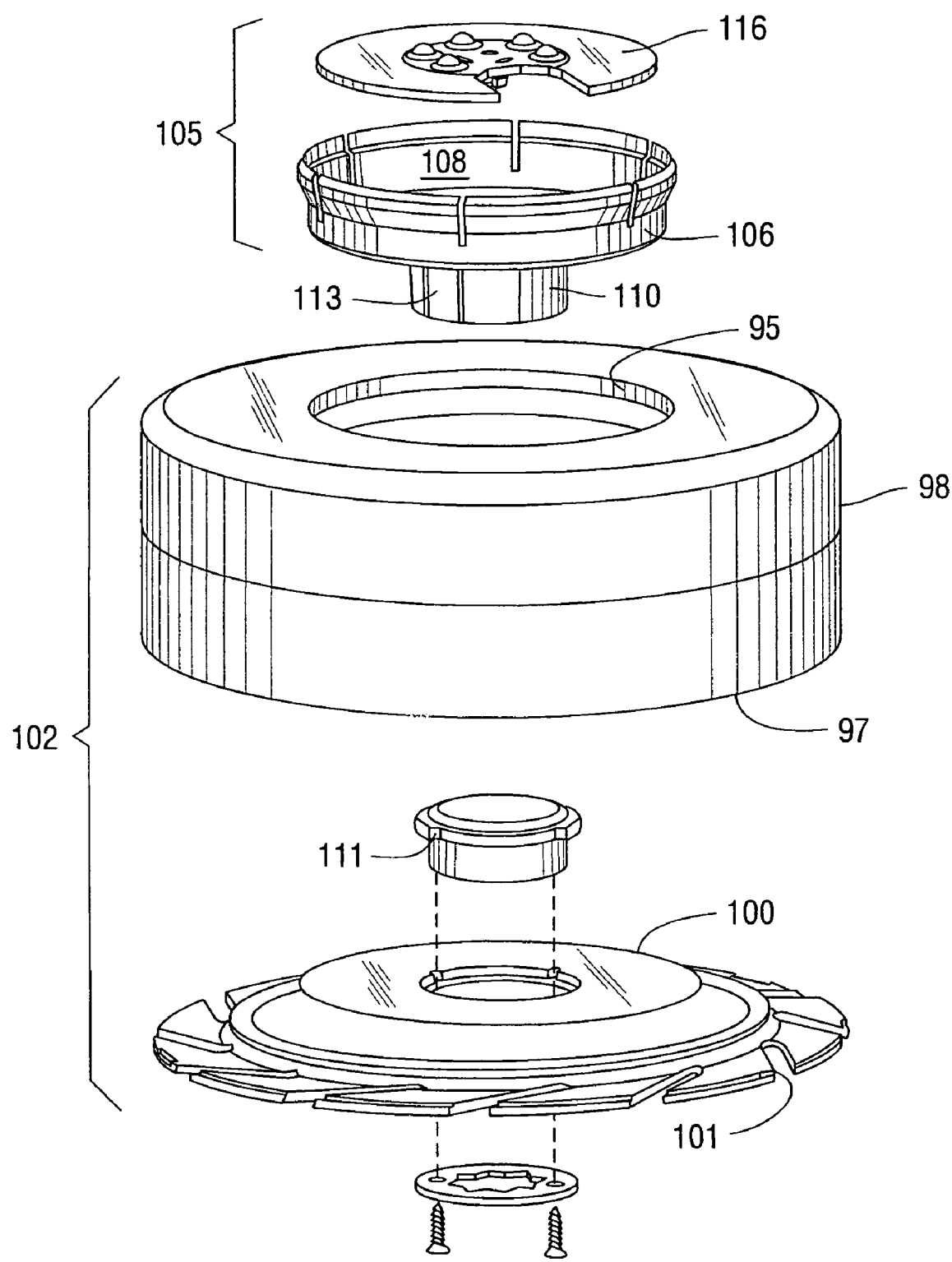
FIG. 8 is an exploded view of the hopper disc assembly and feed regulator.
Figure 9A:
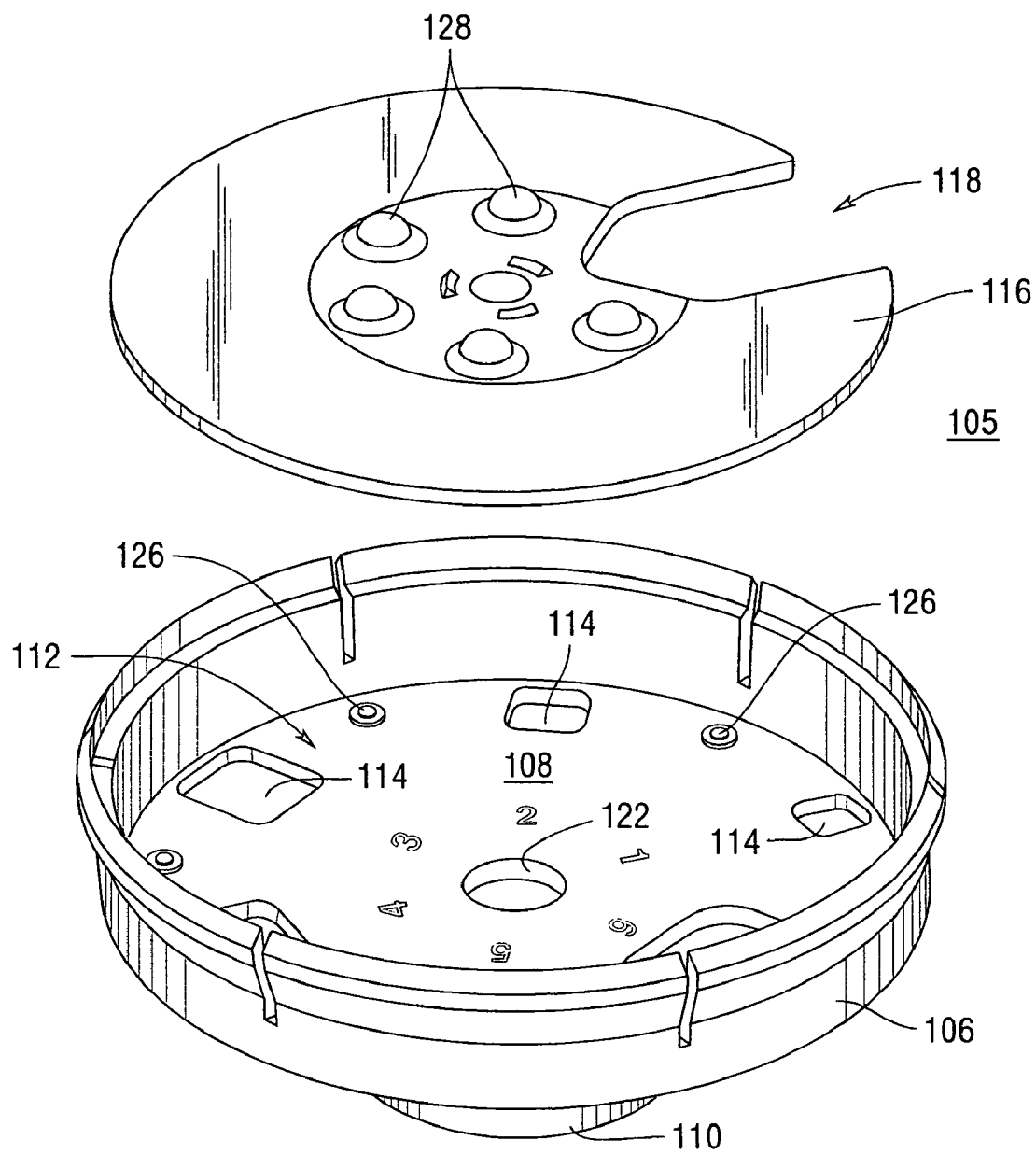
FIG. 9A is an exploded, perspective view from the top of the feed regulator.

The regulator 105 of the present embodiment is perhaps best seen in FIGS. 9A, 9B and 9C, which are various views of the components of the regulator 105, while the relationship between the components of the regulator 105 and the lower hopper shell 98 and dispensing disc 100 are perhaps best seen in FIGS. 8 and 10.

As seen in the aforementioned figures, the regulator 105 is comprised of a cup-shaped member 106 defining a metering section 108. A connecting collar 110 extends from the bottom of the cup-shaped member 106, although other forms of connection may be used. The connecting collar 110 is designed for connection to the rotating disc 100 as shown in FIG. 8. When the connecting collar 110 is connected to the rotating disc 100, the cup-shaped member 106 (which grips the sides of feed regulator 105 and may also have a detent 113 on collar 110 that fits into a notch 111) rotates with the dispensing disc 100.

A bottom 112 of the metering section 108, seen best in FIG. 9A, is a flat member having a plurality of openings 114 of various sizes formed therein. The various sized openings 114 are provided to enable metering or feeding of various sized medicaments. A selection plate 116 having a selection opening 118 is sized to fit within cup-shaped member 106 and cover all of the openings 114 except for one of the openings 114. A plurality of tabs 120 (see FIG. 9B) extending from the bottom of selection plate 116 cooperate with an opening 122 (see FIG. 9A) positioned in the center of cup-shaped member 106 to hold the selection plate 116 firmly in the bottom of the metering section 108. A plurality of recesses or holes 124 (see FIG. 9B) formed in the bottom of selection plate 116 cooperate with raised portions or pins 126 (see FIG. 9A) in the metering section 108 to maintain the selection opening 118 in the proper orientation with respect to the selected one of the plurality of openings 114. When the desired opening 114 is selected by lining up the selection opening 118 with the selected one of the plurality of openings 114, the selection plate 116 is snapped into position. In that manner, dispensing device 12 can be tailored to dispense medicaments of differing sizes by simply choosing the proper alignment of the selection opening 118 with the desired one of the plurality of openings 114. The upper surface of the selection plate 116 may carry a plurality of stirring devices 128 (see FIG. 9A) which, in the current embodiment, are raised portions or bubble-like structures.

Assembly of the dispensing device 12 is a matter of lining up the various components and snapping them together. The selection plate 116 is inserted into cup-shaped member 106. The feed regulator 105 is positioned within lower hopper shell 98 and connected to dispensing disc 100. Those components are inserted between upper platform 94 and lower platform 96, which may be designed with tabs to enable them to be held together with a snap fit, and aligning tabs in the upper hopper 80 with slots in the upper platform 94 to enable the upper hopper 80 to be snapped onto lower hopper 82 thus enabling the entire device 12 to be easily and readily assembled, as will be described in greater detail in conjunction with another embodiment of the present invention.

Turning now to FIG. 11, the lower platform 96 may be seen as the device 12 is viewed from the bottom. The lower opening 104 may be partially covered by a barrier strip 140. Barrier strip 140 permits one medicament to fall through opening 104 from one groove 101 at a time. A socket 142 is designed to receive motor drive block 54 (see FIG. 3C) to enable rotary motion to be imparted to the dispensing disc 100. The provision of the barrier strip 140 and the imparting of rotary motion to socket 142 are known in the art as illustrated, for example, by U.S. Pat. No. 4,869,394, which is hereby incorporated by reference.

The bottom of lower platform 96 also contains alignment pins 144 which cooperate with alignment sockets 50 (see FIG. 3C) for properly aligning the dispensing device 12 within the dispensing cell 16. Finally, the bottom of the dispensing device 12 may carry machine-readable indicia 146. In this document, whenever reference is made to machine-readable indicia or a bar code, any type of identification mechanism appropriate under the circumstances can be employed such as, for example, radio frequency (RF) tagging of the dispensing devices 12 or, in the case of a user, RF tagging, retinal scanning, scanning finger prints, etc. would all be appropriate identification mechanisms.

Figure 12A:
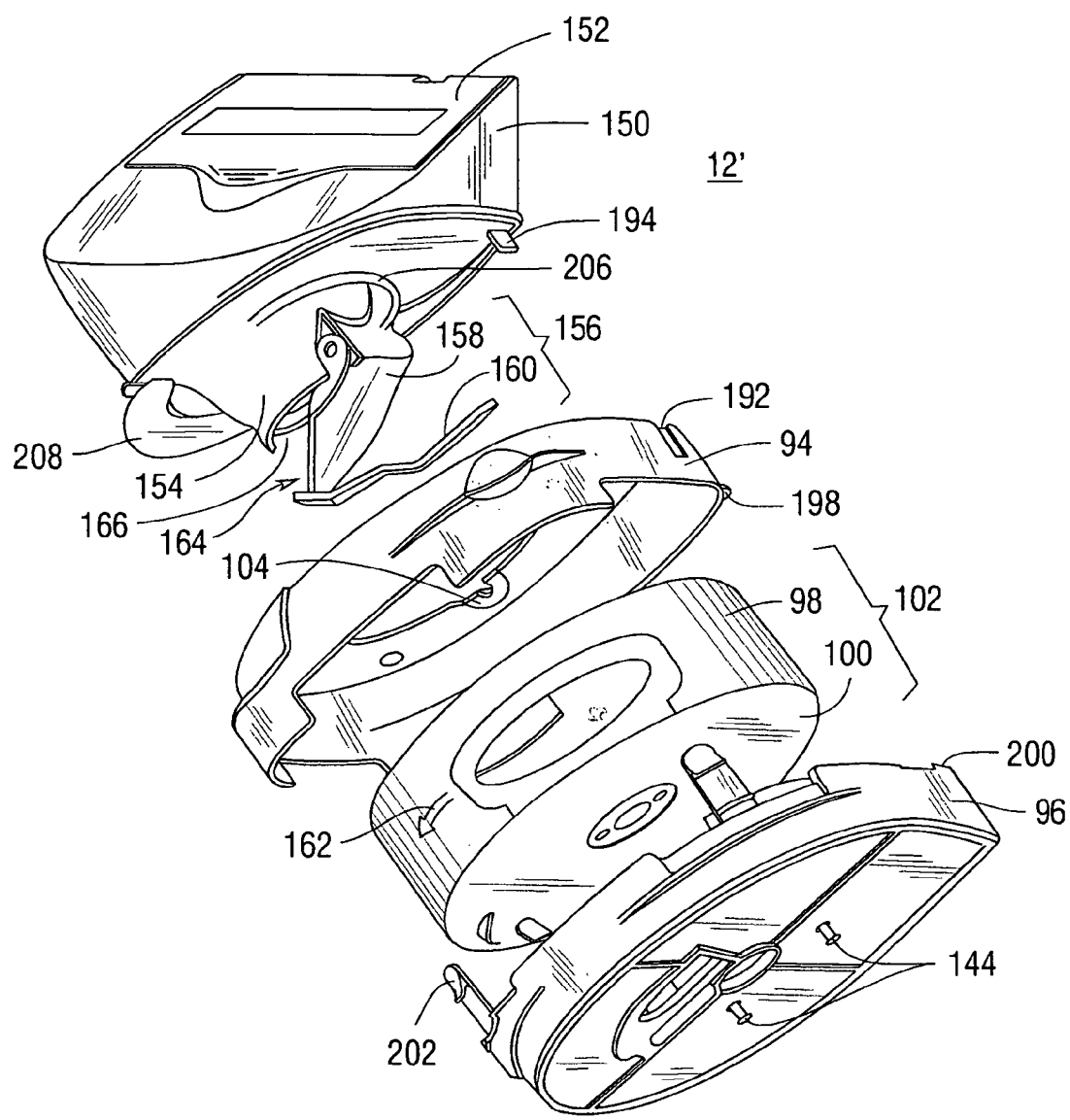
FIGS. 12A and 12B are exploded perspective and cross sectional views, respectively, of another embodiment of a dispensing device.
Figure 12B:
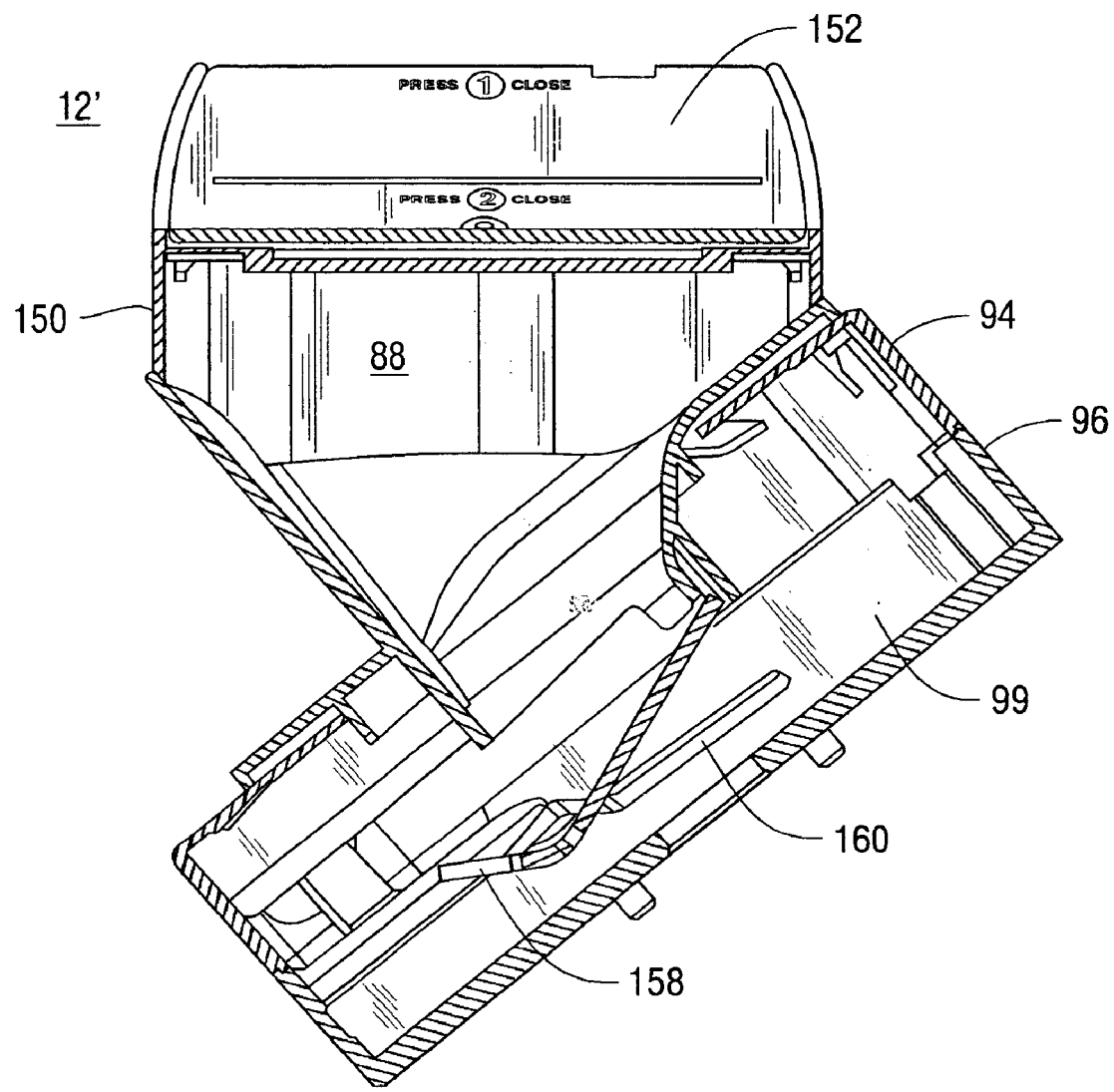

Another embodiment of a dispensing device 12' constructed according to the teachings of the present invention is illustrated in FIGS. 12 and 13. In FIGS. 12 and 13, components identical in construction and operation to those previously identified are provided with the same reference numerals. In FIG. 12A, the dispensing device 12' is comprised of an upper hopper 150 and lid 152 of a similar function, but somewhat different construction, as the upper hopper 80 and lid 68, respectively. The dispensing device 12' is also comprised of an upper platform 94 and lower platform 96 which contain the lower hopper shell 98 and dispensing disc 100 as previously described.

Medicament stored in the upper chamber 88 is fed by gravity through a feed nozzle 154 into the dispensing chamber 99. A feed regulator 156 restricts the flow of medicament through the nozzle 154 into the dispensing chamber 99 to maintain an optimum medicament quantity level for dispensing by the slotted disc 100. The feed regulator 156 is comprised of a trap door valve 158 pivotally connected to nozzle 154, and further connected to a float 160.

The float 160 is oriented within the hopper disk 102 where the majority of the medicament concentrates as the dispensing device 12' operates. As the hopper disk 102 rotates in the direction shown by arrow 162, the medicament migrates to the outer edge of the hopper disk 102 and is pulled upward by the slotted dispensing disk 100 and into the vicinity of the float 160. The leading edge of the float 160 is designed to direct the medicament flow underneath the float 160 to thereby allow float 160 to "ride on" the medicament. The level of medicament in dispensing chamber 99 determines the position of float 160.

As the medicament level in the dispensing hopper disk decreases, the float 160 is lowered which opens the valve 158, allowing medicament from the upper chamber 88 to flow through the feed nozzle 154 and into the dispensing chamber 99. The valve 158 opens as a result of gravity and the weight of the medicament. As the medicament level rises, the float 160 also rises forcing the valve 158 toward its closed position.

Figure 13A:
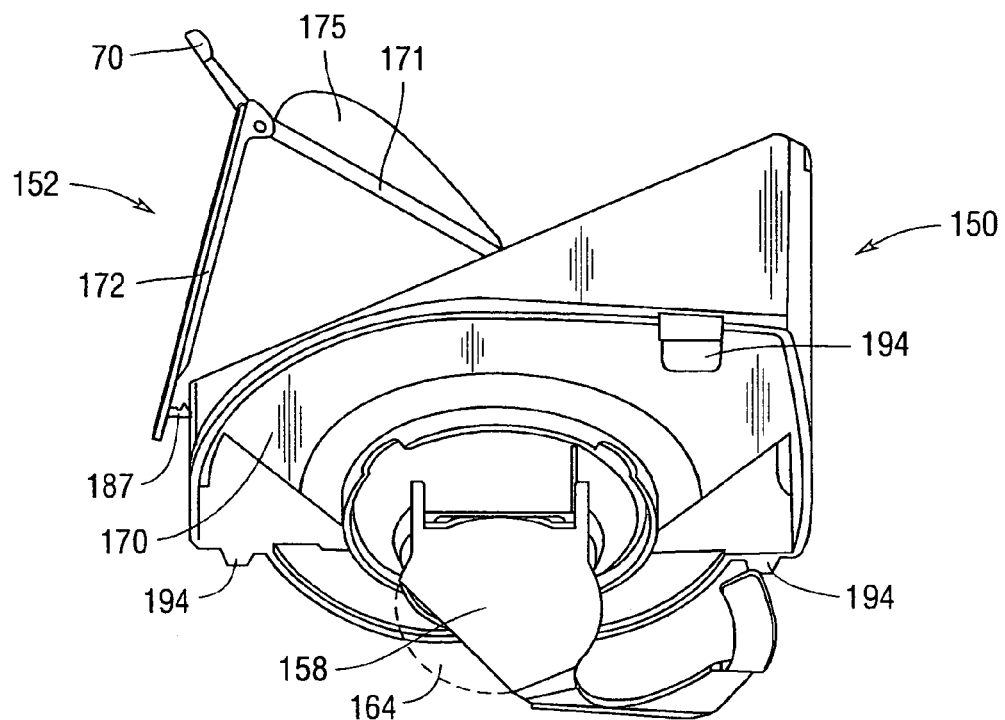
FIGS. 13A and 13B are a side view and a perspective view, respectively, of the upper hopper and feed regulator of the dispensing device shown in FIGS. 12A and 12B.
Figure 13B:
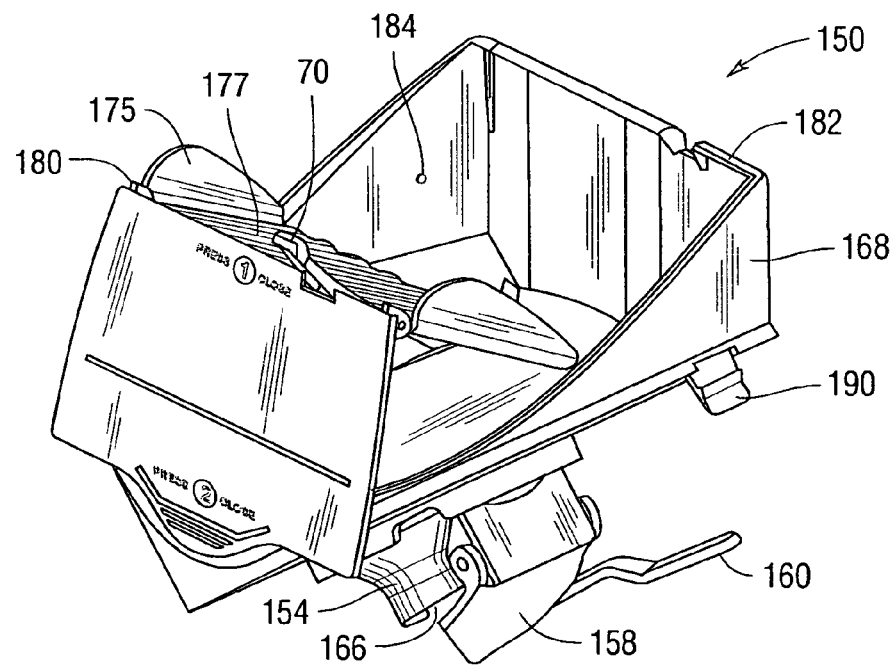
Figure 13C:
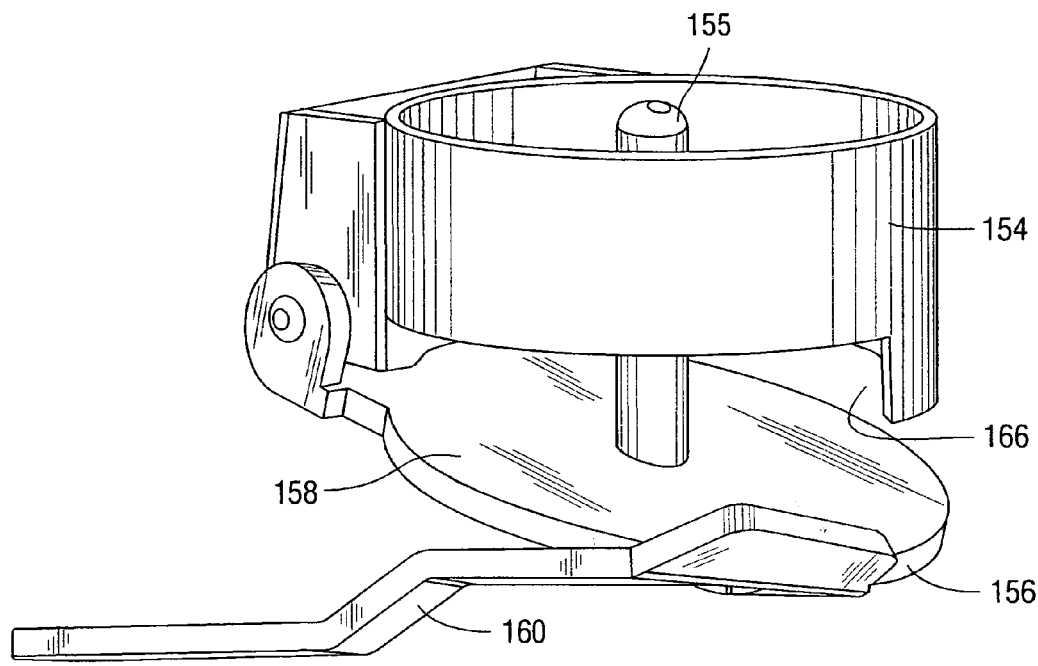
FIG. 13C illustrates the feed nozzle, trap door valve and float.
Figure 13D:
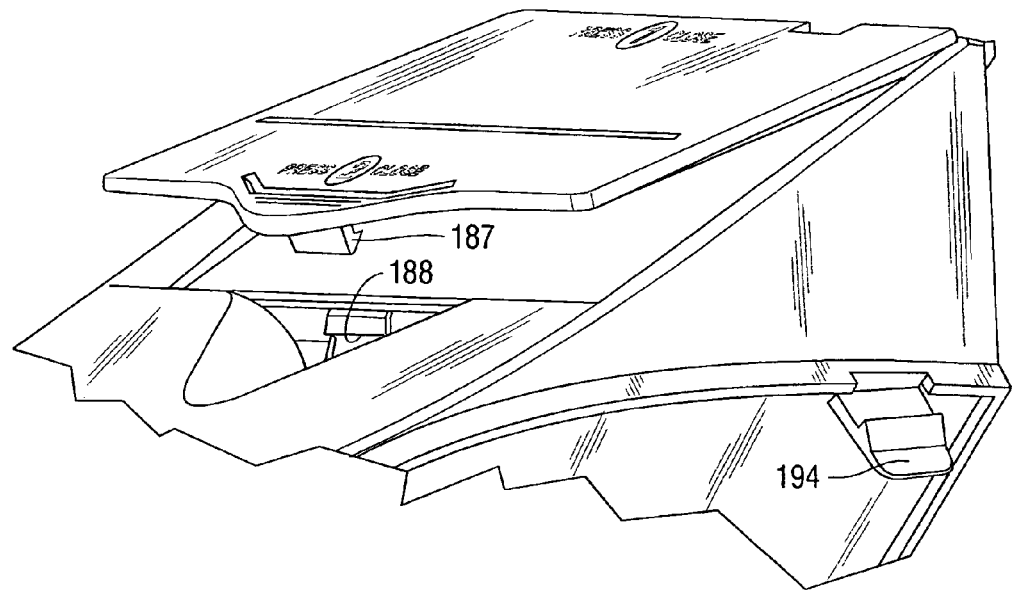
FIG. 13D illustrates details of the lid closure.

The valve 158 may be designed so that a portion of the feed nozzle 154 is never closed by the valve 158 as indicated by numeral primer 164 and referred to as the feed regulator primer (See FIG. 13C). The feed regulator primer 164 allows medicament to flow into the dispensing chamber 99 when the upper hopper chamber 88 is initially filled with medicament. A probe 155, responsive to the valve 158, may be provided for agitating the medicament as the valve 158 moves up and down.

Another mechanism to allow a small amount of medicament to continuously flow into the dispensing chamber 99 as the hopper disc assembly 102 operates is to remove a portion 166 of the feed nozzle 154 as shown in FIGS. 12A, 13B, and 13C.

Because of the pivot connection between valve 158 and feed nozzle 154, there is a natural tendency for the valve 158 to remain open under the influence of gravity. The valve 158 is closed by the medicament randomly becoming stacked and layered between the regulator float 160 and disk 99 as the medicament rotates inside the hopper disk assembly 102.

The preferred embodiments disclose a dispensing device which eliminates the overfilling of the dispensing chamber 99 by virtue of the feed regulators 105, 156 maintaining an ideal quantity of medicament within the dispensing chamber 99. When the ideal medicament level is maintained in the dispensing chamber 99, the dispensing disk 100 is able to operate efficiently and effectively. By maintaining the proper medicament level in the dispensing chamber 99, the medicament is not crushed, jammed or damaged by the rotating dispensing disk 100. The medicament is allowed to freely tumble within the rotating hopper disk assembly 102 and is gently agitated into the dispensing disk slots 101 for dispensing.

FIGS. 13A and B illustrate the upper hopper 150 and lid 152. The upper hopper 150 defines an upper hopper area 168 and a lower hopper area 170. The lid 152 is comprised of a first lid part 171 and a second lid part 172. The upper hopper 150 is, in general, filled from the top through the lid 152 and empties through the feed nozzle 154. The first lid part 171 has sides 175 creating a funnel to assist the worker during the replenishment of the dispensing device 12' from medicament stock bottles. Ridges 177 on the surface of the first lid part 171 guide the medicament into the upper hopper area 170 while the worker pours the medicament from the medicament stock bottle. The large opening created by the unique design of the upper hopper 150 and its lid 152 allows the worker to easily pour medicament from all size medicament stock bottles used in the pharmacy.

To close the lid 152, the worker places the lid parts 171 and 172 in a closed position and presses down on the rear center of the lid part 172. As seen in FIG. 13B, a pair of curved lid snaps 180 deflect a lip 182 outward. The lid snaps 180 snap into a latched position under lip 182 while lid sides 175 are restricted from further movement by a pair of lower lid stops 184. The lower lid stops 184 restrict the movement of the first lid part 171 into the upper hopper area 168. The worker then presses on the front of the second lid part 172 such that a latching tab 187 (See FIG. 13D) is deflected by its leading edge and snaps under an upper lid catch 188. When in the latched position, the lid 152 prevents medicament from exiting the upper hopper chamber 88 while device 12' is being transported.

The upper hopper area 168 and lower hopper area 170 are constructed to create a bulk storage chamber without abrupt interior edges or ledges for medicament to become lodged in or on. All surfaces of the lower hopper area 170 are sloped and curved to eliminate edges and ledges that prevent medicament from flowing into the lower section of the lower hopper area 170 which becomes the feed nozzle 154. The upper hopper 150 relies completely upon gravity to affect medicament flow from the upper hopper area 168 and lower hopper area 170 into the feed nozzle 154.

Turning now to the issue of assembly, as shown in FIG. 12A the float 160 is inserted through a center opening in the upper platform 94. Upper hopper latching tabs 194 are aligned with and inserted into slots 192. As the worker presses the latch tabs 194 into the slots 196, the upper hopper 150 is locked to the upper platform 94.

The hopper disk assembly 102 is inserted into the lower platform 96 and the upper platform 94 is aligned by the worker. An upper platform housing pin 198 is oriented and aligned with a lower platform socket 200 and inserted underneath the platform socket 200. At the same time platform latch slots (not shown) align with platform latches 202. The worker presses the upper platform 94 onto the lower platform 96; the platform latches 202 are deflected by the platform latch slots and come to rest behind the slots, latching the two pieces together. Hopper tension springs 204 (Seen best in FIG. 6) located on the upper platform 94 maintain a constant pressure between the hopper disk assembly 102 and upper platform 94 once the upper platform 94 is latched to the lower platform 96.

A lower hopper sealing ring 206 and hopper spring 208 prevent medicament inside the dispensing chamber 99 from migrating outside of the device 12' during operation or transportation.

Figure 14:
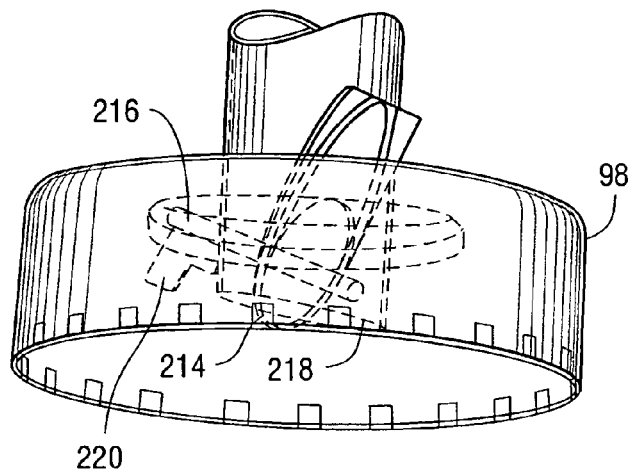
FIG. 14 illustrates a butterfly valve which may be used in place of the trap door valve for purposes of regulating feed between the upper hopper and the lower hopper.

Turning now to FIG. 14, FIG. 14 illustrates a butterfly valve 214 which may be used in place of the trap door valve previously described for purposes of regulating feed between the upper hopper 80 and lower hopper 82. The butterfly valve 214 is connected to a rotatable arm 216 which is positioned within an opening 218 such that upon rotation of the arm 216, the position of the butterfly valve 214 within opening 218 is adjusted. Rotatable arm 216 has a flag portion 220 extending outwardly therefrom. Those of ordinary skill in the art will appreciate that flag portion 220 is capable of interacting with medicament held within dispensing chamber 99 so as to rotate arm 216. Thus, when the level of medicament is low, the flag 220 points substantially downward thus holding the butterfly valve 214 in an open position. Conversely, when the level of medicament in the dispensing chamber 99 is high, the flag 220 begins to move from the vertical downward position toward a horizontal position thereby moving the butterfly valve 214 to close the opening 218. The butterfly valve 214 may be designed such that even in the fully closed position, a portion of the opening 218 remains unblocked by the butterfly valve 214 to insure some minimal amount of continuous flow.

Figure 15A:
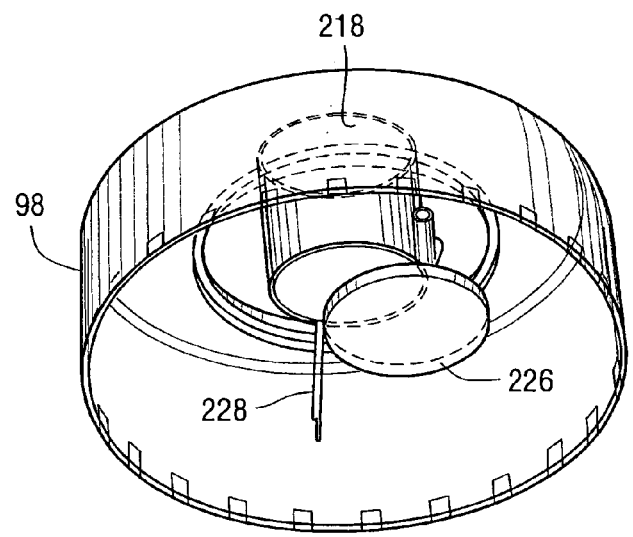
FIG. 15A illustrates an automatic guillotine valve and FIG. 15B illustrates a manual guillotine valve, respectively, which may be used in place of the trap door valve for purposes of regulating feed between the upper hopper and the lower hopper.

In FIG. 15A a guillotine valve 226 is illustrated for controlling the opening 218. The guillotine valve 226 is connected to an arm 228 which interacts with the volume of medicament in the dispensing chamber 99 to control the area of the opening 218 that is restricted by the guillotine valve 226. The guillotine valve 226 is pivotally connected at an angle to the feed nozzle such that it is urged in one direction by gravity and urged in the other direction by arm 228. Guillotine valve 226 may be configured or connected such that a portion of the opening 218 is always open.

Figure 15B:
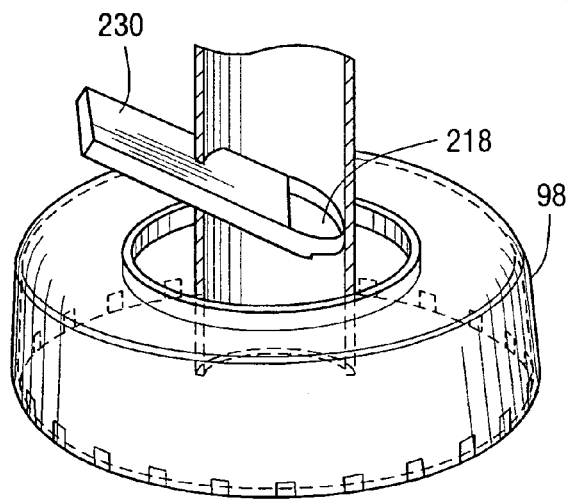

FIG. 15B illustrates another type of guillotine valve 230 which may be used to control the opening 218. The guillotine valve 230 in FIG. 15B is adjusted by the user prior to being put into operation. Thus, the guillotine valve of FIG. 15B may be thought of as a fixed valve as it is manually set by the user and that setting does not change based on the level of medicament in the dispensing chamber 99.

Figure 16:
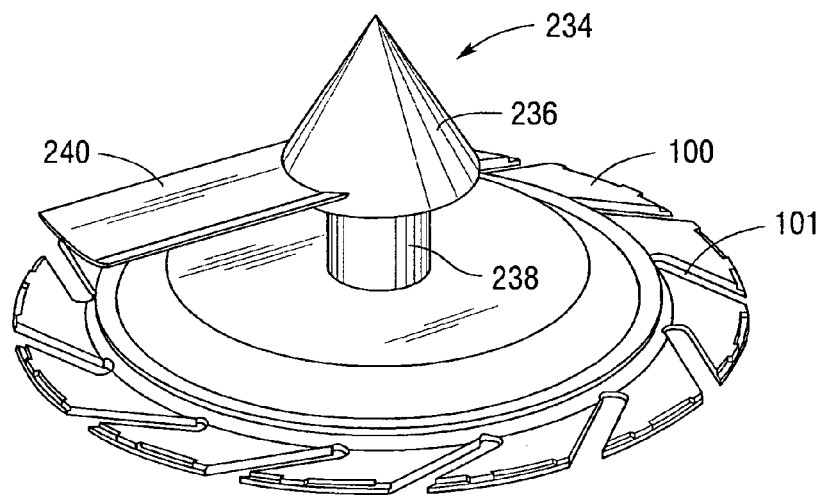
FIG. 16 illustrates a conical plunger which may be used in place of the trap door valve for purposes of regulating feed between the upper hopper and the lower hopper.

FIG. 16 illustrates a conical plunger valve 234 which may be used in place of the previously described valves. As seen in FIG. 16, the plunger valve 234 is comprised of a cone 236 which is capable of riding up and down on shaft 238. Shaft 238 is connected to the dispensing disk 100. Cone 236 may also carry one or more wings 240, angled in the direction of motion as shown in FIG. 16. The wing 240 interacts with the medicament present in the dispensing chamber 99. The greater the volume of medicament in the dispensing chamber 99, the higher the cone 236 on shaft 238, thereby tending to close the opening 218, not shown in FIG. 16. Conversely, the lower the level of medicament in the dispensing chamber 99, the lower the cone 236 on shaft 238, such that the cone 236 is withdrawn from opening 218 thereby allowing a greater volume of medicament to enter the dispensing chamber 99.

Figure 17:
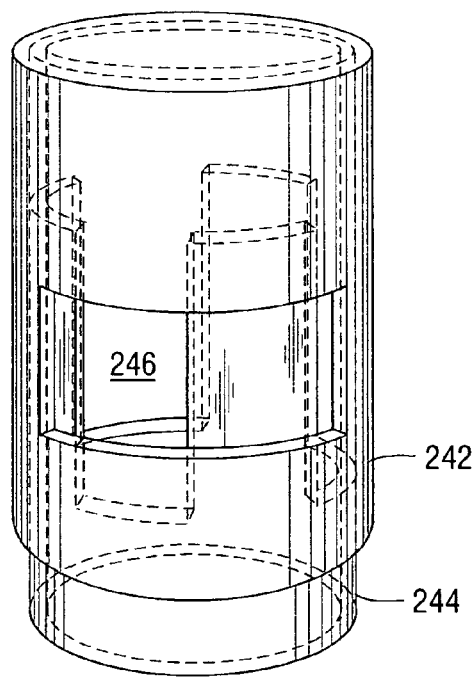
FIGS. 17 and 18 illustrate variable sized nozzles comprised of two cylinders which may be used in place of the trap door valve for purposes of regulating feed between the upper hopper and the lower hopper.
Figure 18:
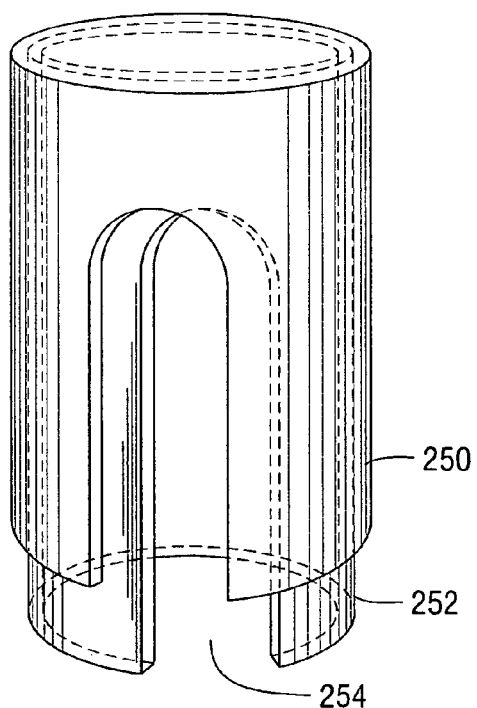

FIGS. 17 and 18 illustrate variable sized nozzles comprised of two cylinders which may be used in place of the trap door valve for purposes of regulating feed between the upper hopper 80 and the lower hopper 82. In FIG. 17, two cylinders 242 and 244 each have a plurality of openings formed therein. The cylinders 242 and 244 are capable of nesting within one another such that upon relative rotation the size of the openings 246 can be manually set by the user. FIG. 18 illustrates a similar embodiment. However, cylinders 250 and 252 each have a single opening such that the size of an opening 254 can be manually set by the user through relative rotation of the cylinders 250 and 252.

Figure 19:
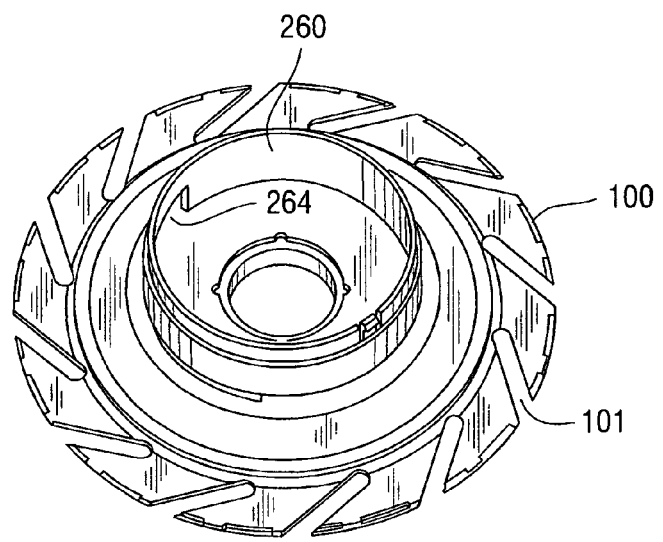
FIGS. 19 and 20 illustrate fixed size nozzles formed of a rotating cylindrical member.
Figure 20:
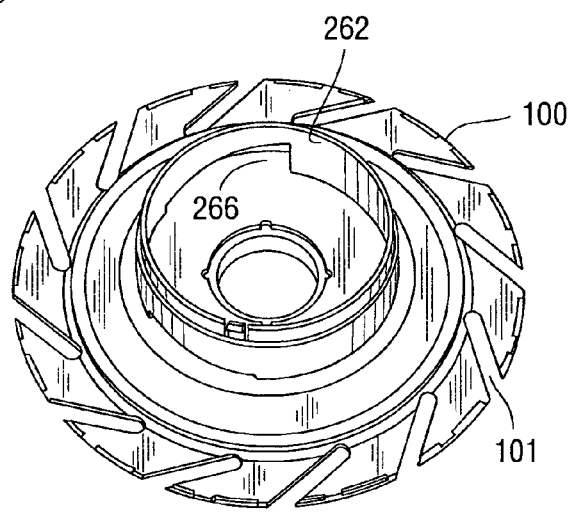

FIGS. 19 and 20 illustrate fixed size nozzles formed in rotating cylinder members 260 and 262, respectively, carried by the dispensing disk 100. The cylinder 260 has an opening 264 formed therein while the cylinder 262 has a larger opening 266 formed therein. The openings 264 and 266 are sized to enable a desired volume of medicament to be fed to the dispensing grooves 101.

Figure 21:
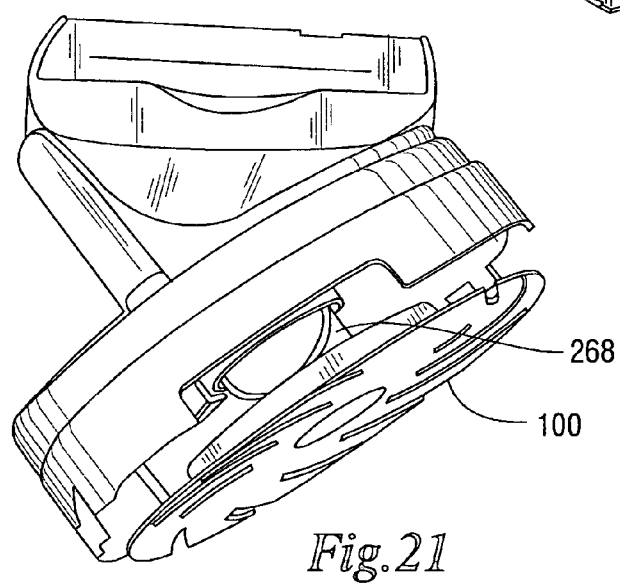
FIG. 21 illustrates a rotating dose cup which may be used in place of the trap door valve for purposes of regulating feed between the upper hopper and the lower hopper.

FIG. 21 illustrates a rotating dose cup 268 which is connected to and rotates with dispensing disk 100. As seen in the figure, the dose cup 268 is mounted at an angle e.g. 45°, with respect to the dispensing disk 100. Upon rotation of the dispensing disk 100 and dose cup 268 the volume of medicament fed to the dispensing grooves 101 can be controlled.

In FIG. 22, a perspective view of the dispensing cabinet 10 is illustrated in which the drawers 14 and the doors 19 and 26 have been removed. The dispensing cabinet 10 is comprised of a frame 330. The frame 330 carries a plurality of shelves 332 equal in number to the number of drawers 14. The shelves 332 are each carried by a pair of drawer glides 334 which enable the shelves 332 to move between a fully closed position, in which the drawer is retracted and positioned within the frame 330, and a fully open position in which the shelf 332 extends outward from the frame 330. The frame 330 together with the shelves 332 define a plurality of drawer openings 336. The shelves 332 and drawer openings 336 are configured so that each shelf may carry a drawer 14. In that manner, the drawers 14 can be moved between their fully closed and fully opened positions.

FIG. 23 is a sectional view of the cabinet 10 shown in FIG. 22 taken along the lines 23-23. As will be seen in FIG. 23, each of the shelves 332 is mounted at an angle with respect to the horizontal such that the front of the shelf, and hence the front of each drawer, is lower than the rear of each shelf and the rear of each drawer. Thus, when a drawer is moved to its fully open position, it extends downwardly and outwardly from the frame 330, whereas when each drawer is in its fully closed position, it remains at the same downwardly extending angle, but is maintained substantially completely within the frame 330. The phrase "substantially completely" refers to the fact that the shelf 332 and drawer glides 334 are retracted such that no portion of the drawer glides 334 is exposed, even though portions of the drawer 14, as seen in FIG. 1, may extend beyond the frame 330.

Figure 24:
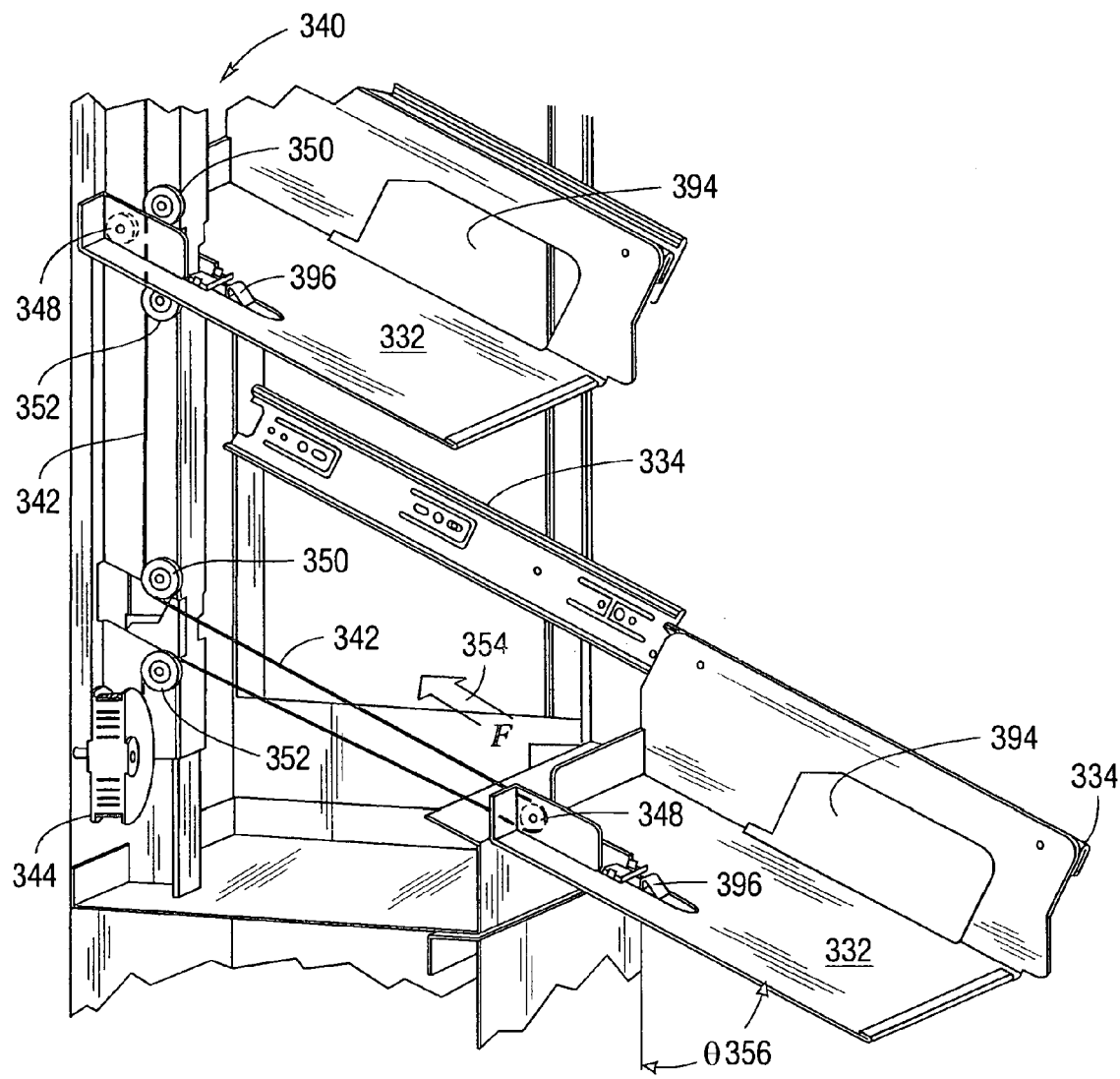
FIG. 24 illustrates the detail of the drawer interlink and counter balance system.

Illustrated in FIGS. 23 and 24 is a drawer interlink and counterbalance system 340. The interlink and counterbalance system 340 is comprised of a flexible member 342 having one end connected to a tensional spring 344 and another end 346 connected either to the frame 330 or to the drawer 14 positioned furthest from the tensional spring 344. As seen in FIG. 23, the flexible member 342 runs behind each of the shelves 332.

Referring now to FIG. 24, each shelf 332 carries a guide member 348 which travels with the shelf 332 and, as shown in FIG. 24, is positioned to the left of flexible member 342. Positioned above and below each guide member 348 is an upper roller 350 and lower roller 352, each of which is carried by the frame 330. Once a drawer 14 is unlocked, as will be described below, the drawer glides 334 enable the shelf 332 to be moved from the fully closed to the fully open position. As the shelf 332 moves from the fully closed position, the guide member 348 engages flexible member 342 between the upper roller 350 and lower roller 352. As the shelf 332 is moved to its fully open position, the tensional spring 344 is played out enabling the drawer to move to its fully open position. The tensional spring 344 exerts a force through member 342 which creates counterbalance force 354 opposing the gravitational forces on the drawer 14.

The flexible member 342 is under constant tension by virtue of the tensional spring 344. The force exerted by the tensional spring 344 may be calculated to support the average weight of a drawer, which is approximately 23 pounds. Because the guide member 348 pulls the flexible member 342 in a manner to cause the flexible member 342 to engage both the upper roller 350 and lower roller 352, the force of the tensional spring 344 is doubled. Most of the drawer weight is supported by the frame 330 through drawer glides 334. The outward force component is equal to the sine of the drawer angle 356. The force of the tensional spring 344 required to support a drawer 14 is found using the formula:

$F = W*(\theta/2)$ where

F=spring force

W=weight of drawer glides 334+drawer 14

θ=angle of drawer outward slope in degrees.

For example, F=23 pounds*sine(25/2)=4.86 pounds

For a typical pharmacy application, a spring force of between 4.5 and 5 pounds will normally be adequate to counterbalance a drawer, including drawer glides, weighing approximately 23 pounds. The counterbalance force 354 restricts the rate of descent of the drawer, allowing the worker to maintain control of the drawer as it is opened. Furthermore, the counterbalance force 354 also makes it easier to move the drawer from its fully opened to its fully closed position. The counterbalance force 354 may be generated using other types of devices such as coil springs, helical springs, leaf springs, weights, pneumatic cylinders, etc.

The system 340 is referred to as an interlink and counterbalance system because the flexible member 342 and tensional spring 344 may be sized such that only one drawer 14 may be fully opened at a time, per cabinet 10. Thus, the system 340 not only provides a counterbalance force for each drawer, but provides an interlink between the drawers such that only one drawer may be opened at a time.

Figure 25A:
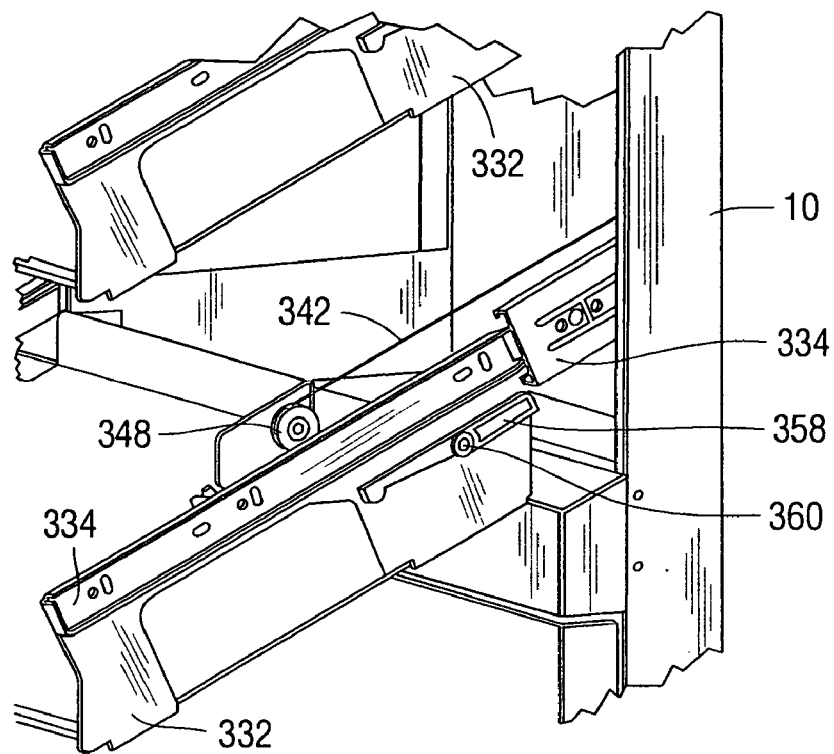
FIGS. 25A and 25B illustrate the rotatable locking arms used to hold the drawer in the open position.
Figure 25B:
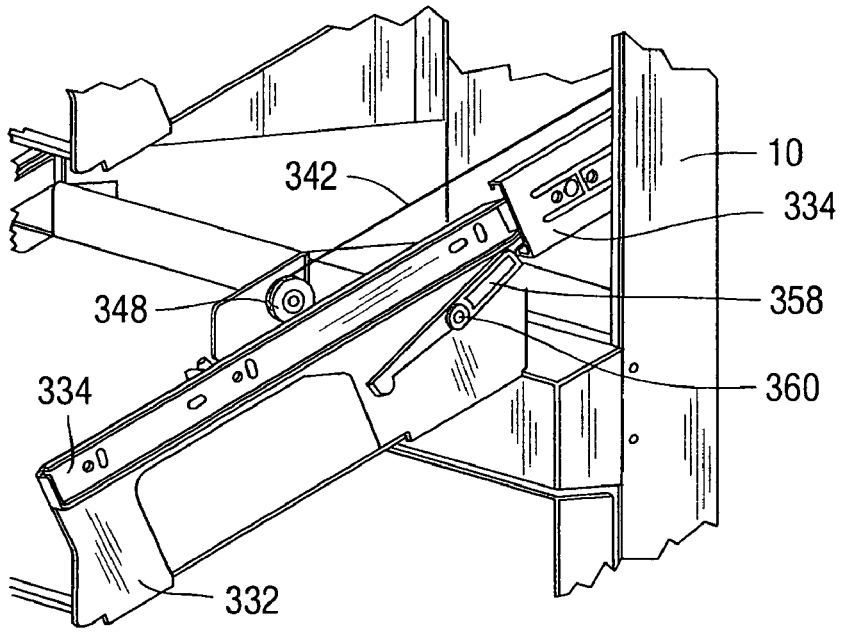
Figure 26:
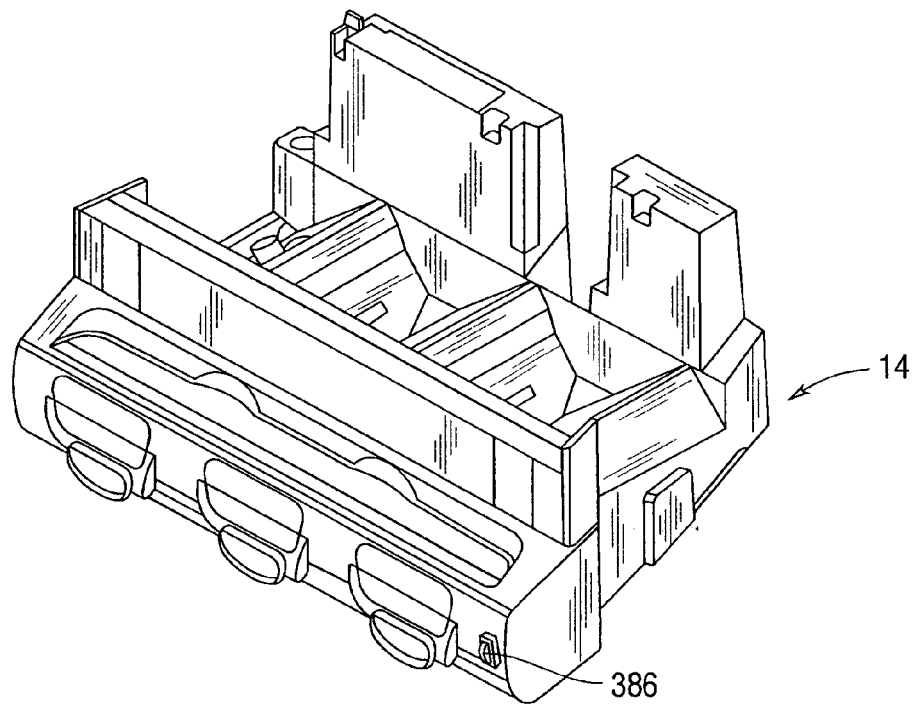
FIG. 26 is a perspective view of the drawer of FIG. 1 with the dispensing devices removed.
Figure 27:
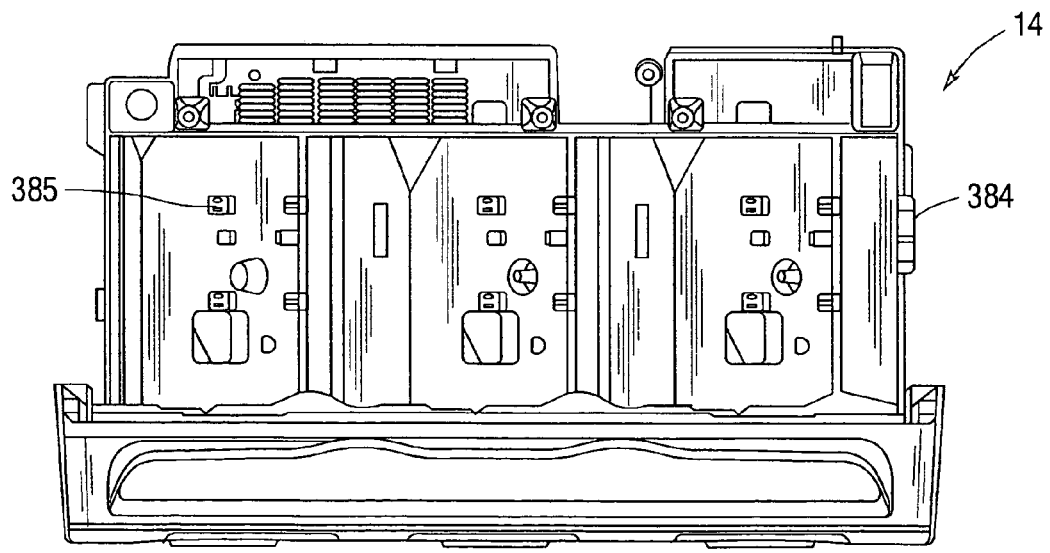
FIG. 27 is a top view looking down on the drawer of FIG. 26.

When the shelf 14 reaches its fully opened position, as shown by the bottom shelf 332 in FIG. 24, the tensional spring 344 has reached its maximum extended position. As a result of the counterbalance force 354, the shelf 332 has a tendency to move toward its fully closed position. To counteract the counterbalance force 354, the drawer 14 may be locked in its fully opened position. As shown in FIGS. 25A and 25B, a pair of rotatable locking arms 358 (one per side) is provided on each shelf 332 just below the drawer glide 334. The rotatable locking arms pivot about pivot point 360 and are weighted at one end such that when the shelf 332 is in the fully opened position, the rotatable locking arms 358 clear the drawer glide 334 and pivot about pivot point 360 such that one end of the rotatable locking arm abuts the drawer glide 334 while the opposite end abuts a portion of the shelf 332. In that manner, the shelf 332, and hence the drawer, are automatically locked into the fully opened position as soon as the drawer 14 assumes the fully opened position without any further action needed by the user.

To move the drawer to its fully closed position, the user rotates both rotatable locking arms 358 into a position parallel to the drawer glide 334 as shown in FIG. 25A. The counterbalance force 354 will start pulling the drawer toward its fully closed position and, with additional force supplied by the user, can be easily moved to its fully closed position where it will be locked in place, as described below.

It is anticipated that the flexible member 342 may be implemented using a plastic coated stranded steel cable although other flexible materials can be used. It is further anticipated that if a flexible member 342 is chosen which also has elastic properties, such as a rubber strand, then the tensional spring 344 may be eliminated. In such an embodiment, pulling on the flexible member 342 will place the member in a state of expansion, and the spring-like properties of the member will produce the necessary counterbalance force.

Figure 3B:
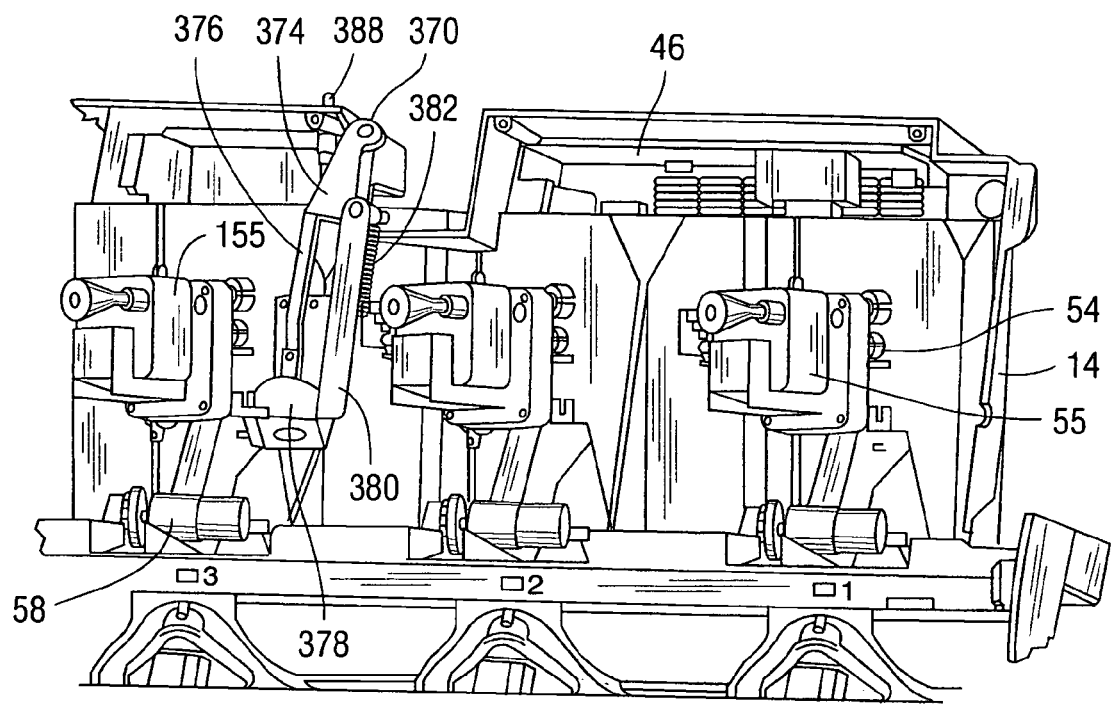
FIG. 3B is a bottom view of the medicament dispensing drawer of FIG. 2A with all three dispensing devices and the shell removed.
Figure 3C:
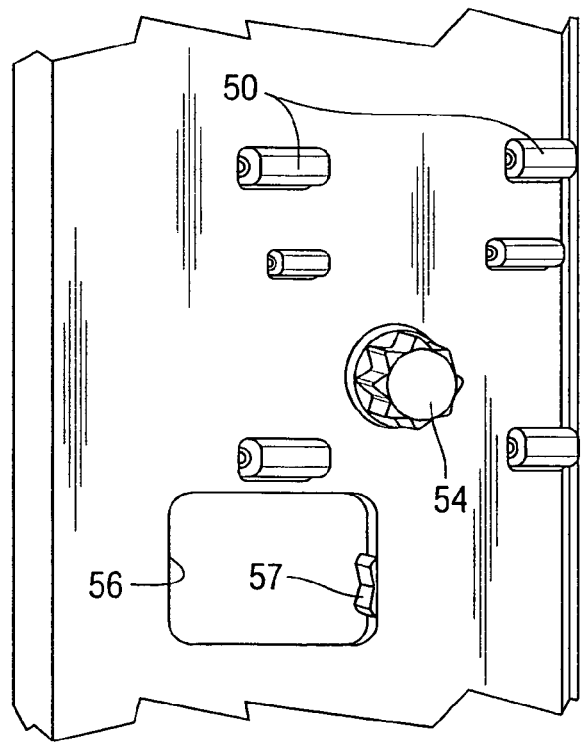
FIG. 3C illustrates the motor disc block and cell drop out opening.
Figure 28:
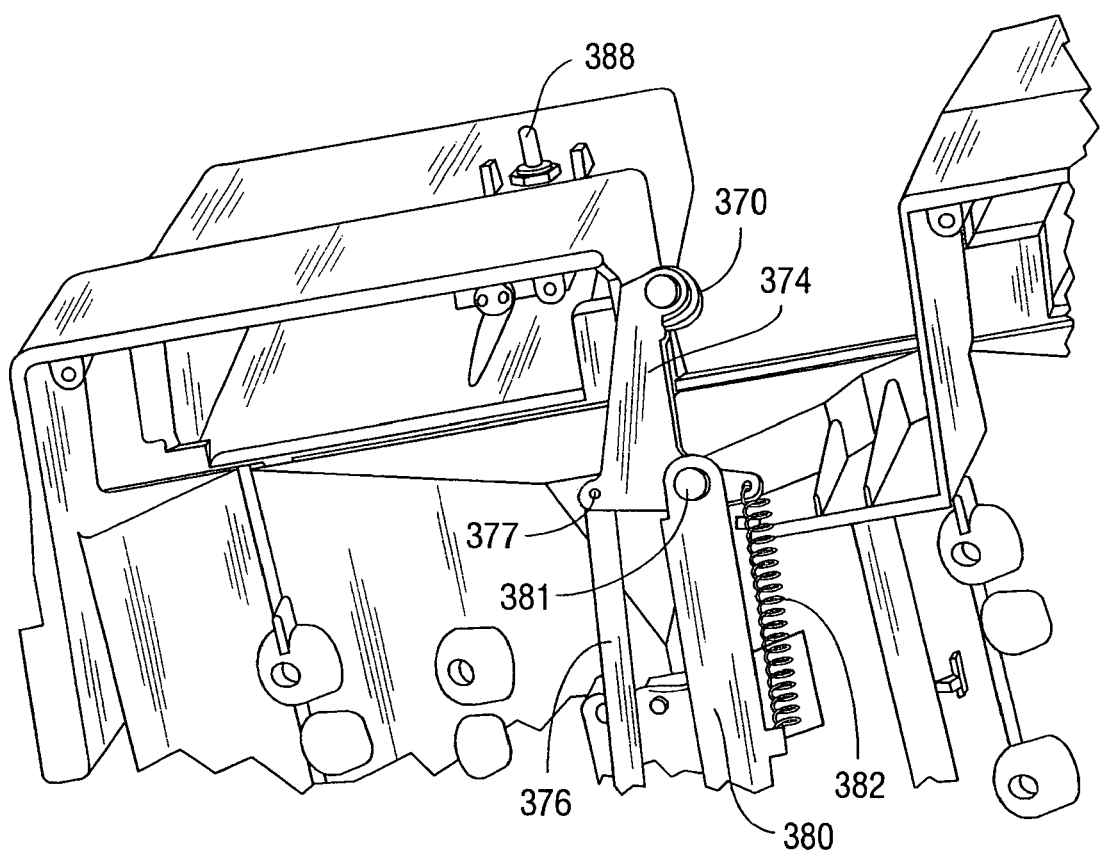
FIG. 28 illustrates the details of a locking assembly.
Figure 29:
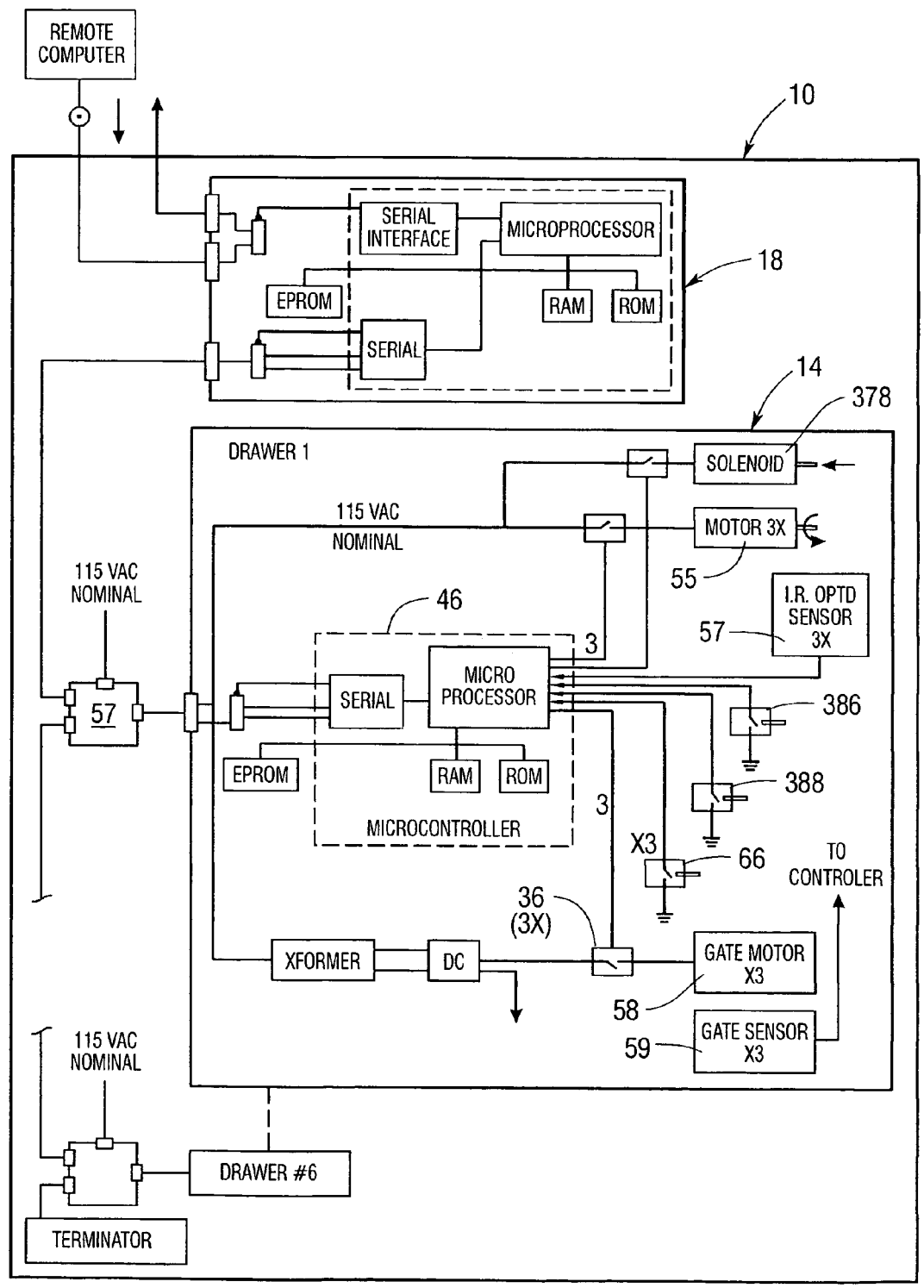
FIG. 29 is an electrical schematic illustrating the cabinet and drawer controllers and associated electronics.
Figure 30:
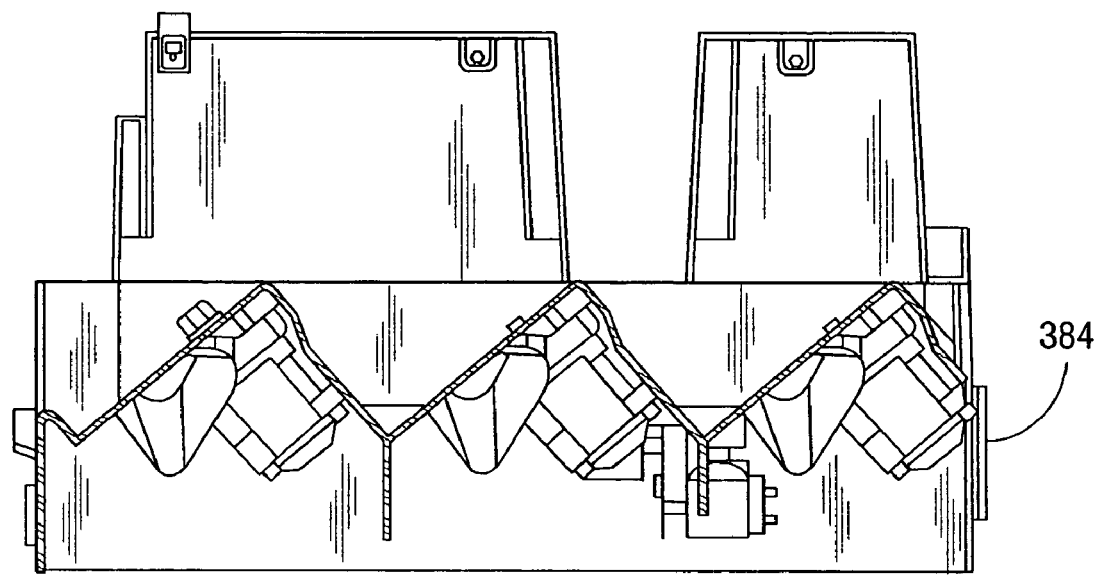
FIG. 30 is a sectional view taken along the lines A-A of FIG. 27.
Figure 31:
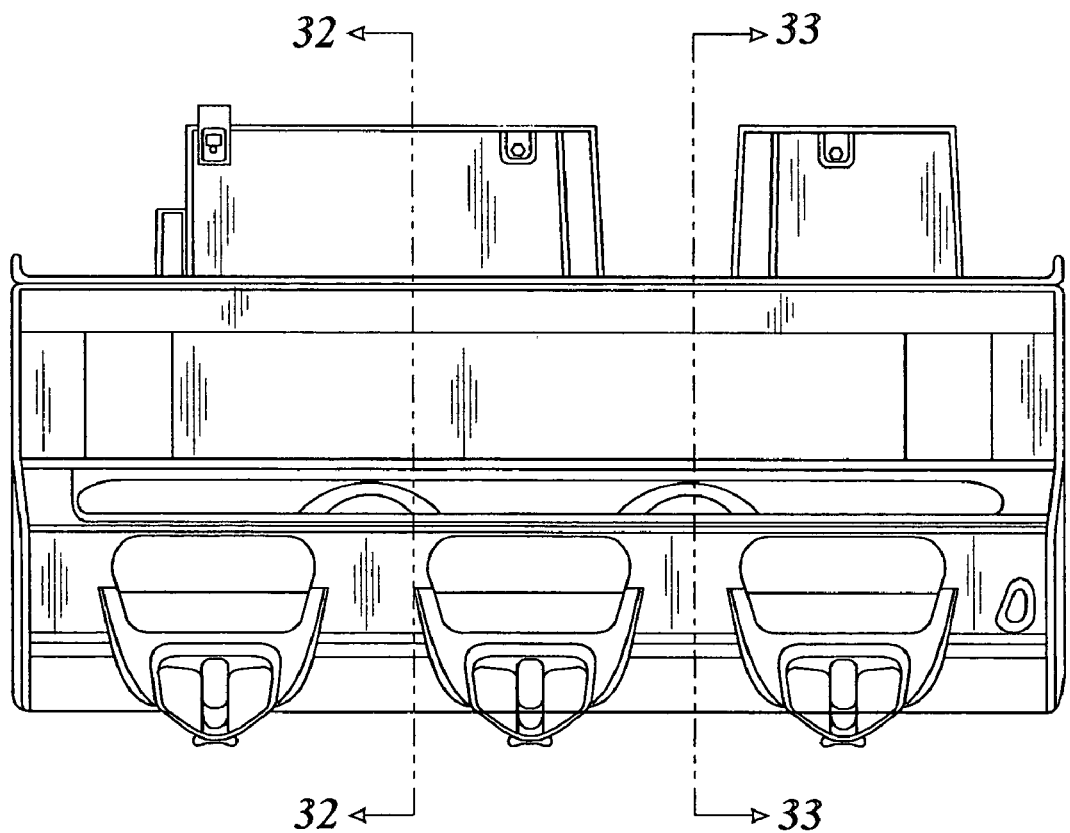
FIG. 31 is a front view of the drawer of FIG. 26.
Figure 32:
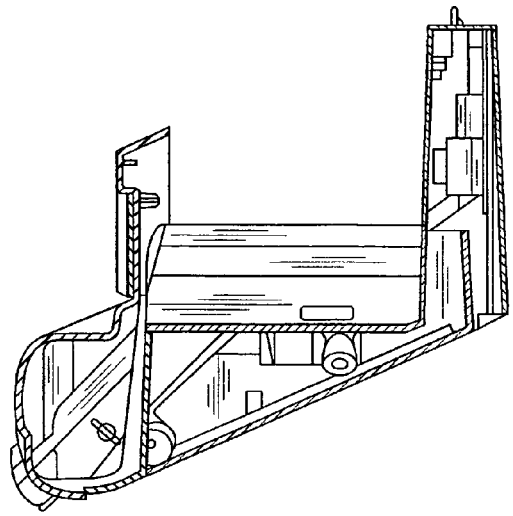
FIG. 32 is a sectional view taken along the lines 32-32 in FIG. 31.
Figure 33:
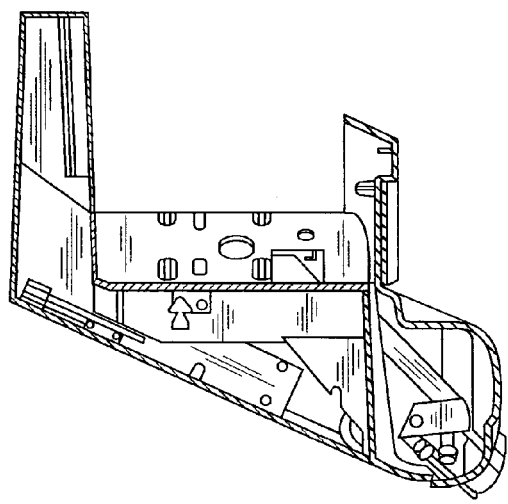
FIG. 33 is a sectional view taken along the lines 33-33 in FIG. 31.
Figure 34:
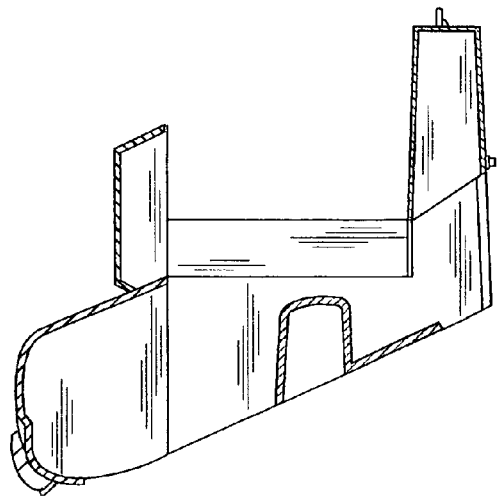
FIG. 34 is a right side view of the drawer of FIG. 26.
Figure 35A:
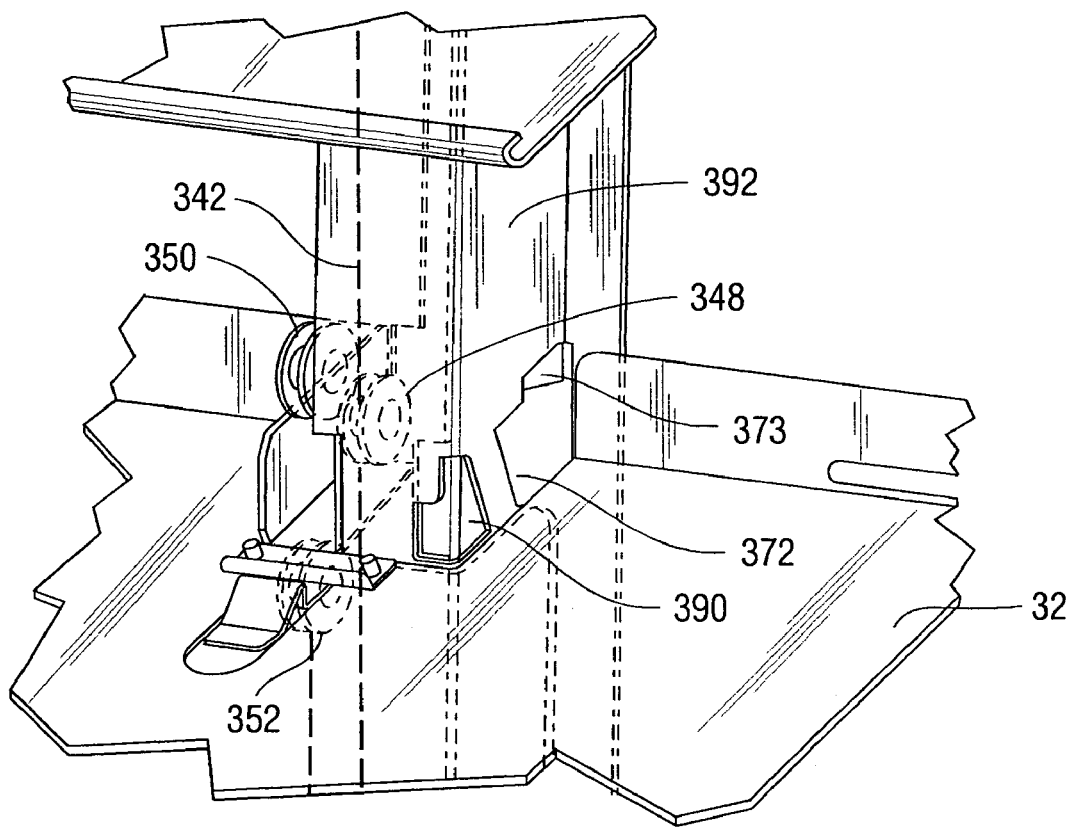
FIGS. 35A and 35B illustrate details of an override mechanism for unlocking drawers in the event of a loss of power or controller failure.

The drawers 14 are shown in greater detail in conjunction with FIGS. 26, 27 and 30-34 while a locking assembly is illustrated in conjunction with FIGS. 3B, 28 and 29. Turning to the locking assembly as shown in FIGS. 3B and 28, the drawer 14 carried by each shelf 332 has a locking assembly which includes a latch roller 370 which engages a strike plate formed by a notch 372 in member 392. (See FIG. 35A.) When each of the drawers 14 is in its fully closed position, the latch roller 370 engages strike plate notch 372 so as to lock the drawer 14 in its fully closed position. Also visible in FIG. 3A is an emergency unlatch rod 373, discussed below.

Figure 35B:
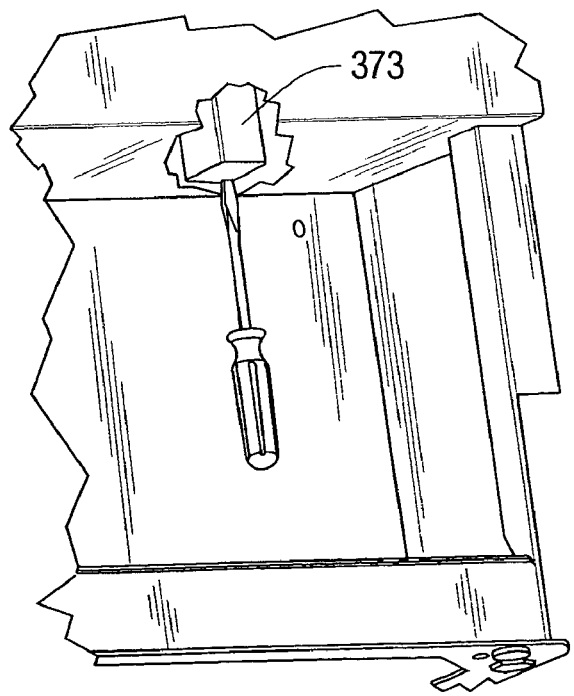

In the event of a power failure and it is necessary to unlock the drawers, a manual override of the drawer locking system is provided. As shown in FIG. 35B, the bottom of emergency unlatch rod 373 is accessible within storage area 24. By pushing upward on rod 373, portions along the rod push each latch roller 370 away from its associated notch 372. Thus, each of the drawers is manually unlocked and can be moved to its fully opened position. A mechanical lock could be placed on the movable member 373 to control access to the manual override.

Turning to FIG. 28, the latch roller 370 is carried by a latch pawl 374. Latch pawl 374 is connected to latch arm 376 at a first pivot point 377. The other end of latch arm 376 is connected to a solenoid 378. (See FIG. 3B). Latch pawl 374 is also pivotally connected to a fixed member 380 at a second pivot point 381. A latch pawl return spring 382 is connected between the latch pawl 374 and the fixed member 380. The connection between spring 382 and latch pawl 374 is at a position opposite to the first pivot point 377 with respect to the second pivot point 381.

With reference to FIG. 29, if the control (remote) computer sends an appropriate command, the cabinet controller 18 forwards the command to the appropriate drawer controller 46 which acknowledges receipt of the command by returning a command response to the control computer via the cabinet controller 18. The drawer controller 46 then begins to monitor a drawer release switch 386 (see also FIG. 26). When a worker presses the drawer release switch 386, the drawer controller 46 issues a command to activate the solenoid 378 (see also FIG. 3B). When the solenoid 378 is activated, the latch arm 376 will be pulled downward in FIGS. 3B and 28, causing latch pawl 374 to rotate counterclockwise about second pivot point 381, overcoming the opposing tension applied by the latch pawl return spring 382. The rotation of the latch pawl 374, counterclockwise as shown in FIGS. 3B and 28, moves the latch roller 370 away from and clear of the strike plate notch 372, thereby unlocking the drawer 14 from the frame 330. The drawer release switch 386 is positioned on the drawer 14 so as to allow the worker to positively grip the drawer 14 while guiding and pulling the drawer 14 to its fully opened position. The activation of solenoid 378 can be timed so that the solenoid is not burned out should the user continue to hold drawer release switch 386 in the closed position.

The drawer controller 46 monitors a drawer position switch 388 (see also FIGS. 3B and 28). Once the drawer 14 has been unlocked, and the drawer 14 begins to move away from the frame 330, the drawer position switch 388 will change state. After a slight delay, the drawer controller 46 will disable drawer release switch 386.

To move the drawer from its fully open to its fully closed position, it is first necessary to rotate locking arms 358 into a horizontal position as discussed above. The user then pushes the drawer back into the frame 330. As the latch roller 370 encounters the strike plate notch 372, the latch pawl 374 rotates away from the strike plate notch 372 in opposition to the force provided by spring 382 as a result of the user pushing the drawer 14 toward its fully closed position. After the latch roller 370 has cleared strike plate notch 372, spring 382 causes the latch pawl 374 to rotate in a direction toward strike plate notch 372 thus securing the latch roller 370 behind strike plate notch 372 and thereby locking the drawer 14 in its fully closed position.

Those of ordinary skill in the art will recognize that alternative embodiments may be used to construct the electronic drawer lock assembly. Such embodiments include the solenoid 378 being connected directly to the latch pawl 374, replacing linear solenoid 378 with a rotary solenoid, further eliminating the need for various pivot points. Additionally, latch roller 370 could be replaced by a cam surface. Although in the present embodiment an unlock command from the control device and user input in the form of depressing drawer release switch 386 are both required to unlock a drawer 14, in other embodiments users might elect to allow the drawer to be unlocked in response to either a command from the control device or user input, without requiring both the command and user input to be present.

FIGS. 30-34 illustrate various views of a drawer 14. As will be seen most clearly in FIGS. 32, 33 and 34, each of the drawers 14 has a sloped bottom thereby enabling each of the drawers 14 to be received by one of the shelves 332 as will now be described.

One side of each drawer contains a protrusion 384 (See FIG. 27) which extends through an opening 394 in shelf 332 (See FIG. 24). The other side of the drawer has a catch tab 385 (See FIG. 27). In addition a spring tab 396 carried by shelf 332 (See FIG. 24) grips the bottom rear of the drawer. To remove a drawer, spring tab 396 is pulled downward while the left side of the drawer is lifted upward away from shelf 332. When the left side of the drawer is sufficiently high above shelf 332, the protrusion 384 can be moved from opening 394 by lifting the drawer up and to the left. Other mechanisms for connecting the drawer to the shelf can be devised by those skilled in the art. The particular mechanism for connecting the drawer to the shelf is not important for purposes of the present invention.

Figure 36:
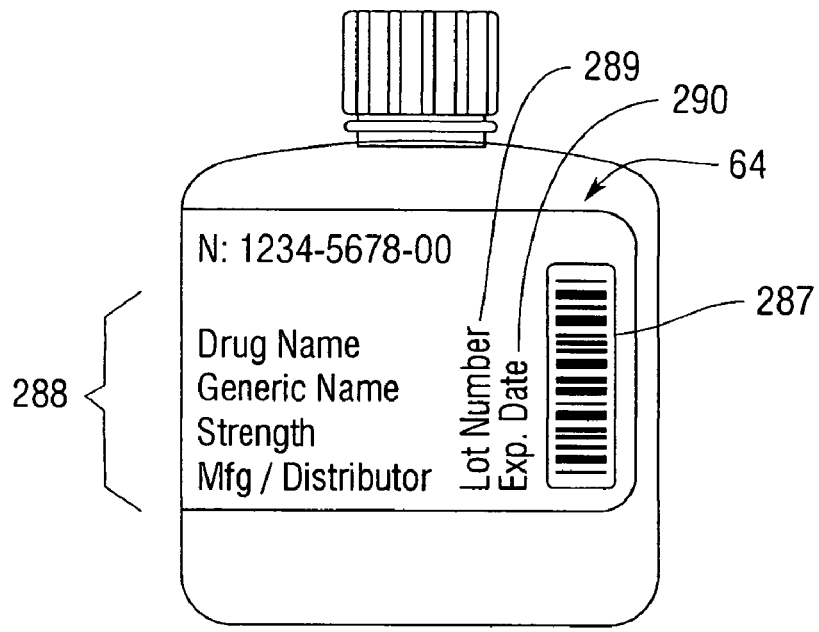
FIG. 36 illustrates a typical bulk medicament stock bottle and label.

FIG. 36 illustrates a typical bulk medicament stock bottle 64 as supplied to a pharmacy by a medicament manufacturer. The bulk medicament stock bottle 64 will generally contain a stock bottle bar code indicia 287 which is unique to the medicament and may also contain a package size code which represents the quantity of medicament in the bulk medicament stock bottle 64. The bulk medicament stock bottle 64 also contains textual information 288 specific to the batch or lot of medicament contained within bottle 64. A lot number 289 and expiration date 290 are printed by the manufacturer when the medicament is packaged into the bulk medicament stock bottle 64. The lot number 289 is used by the pharmacy to track medicament dispensed to patients should the medicament be recalled by the manufacturer. The expiration date 290 is the date by which the medicament must be repackaged into a patient prescription and sold by the pharmacy.

Figure 37:
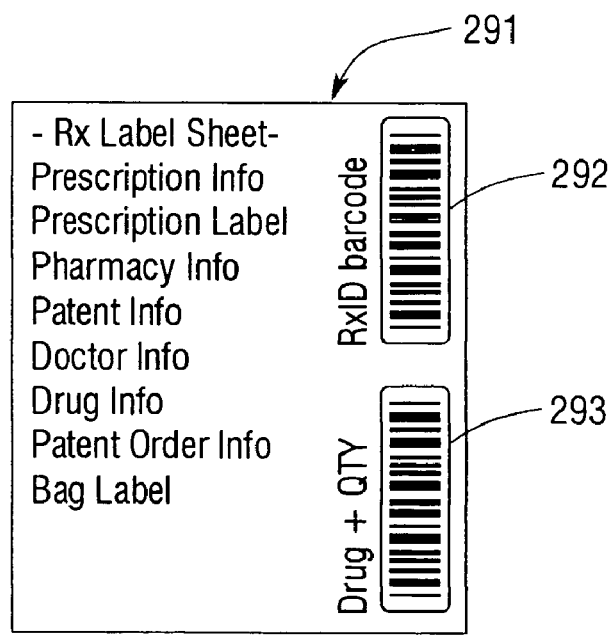
FIG. 37 illustrates a typical patient prescription label sheet as used by a pharmacy.

FIG. 37 illustrates a patient prescription sheet 291 printed by the pharmacy computer system for each patient prescription. The patient prescription sheet 291 comprises a vial label that is applied to the prescription vial 30, prescription bar code indicia 292, and medicament bar code indicia 293, among others. The prescription bar code indicia 292 is a machine readable indicia and represents the patient prescription and allows a dispensing computer 400 (See FIG. 38) to retrieve various elements of the patient prescription transmitted to the dispensing computer 400 by an interface to the pharmacy computer system. The various elements of the patient prescription electronically transmitted may comprise the prescription information (e.g. prescription number, refill number, number of refills, quantity), medicament information (e.g. drug number, drug name, generic drug name, strength, dosage form, manufacturer/distributor), prescription label as required by the particular state pharmacy laws, patient information, prescribing doctor information, order grouping information used to associate all of the patient prescriptions, a bag label to be placed on the completed prescription bag containing the prescription vial 30 and other prescription instruction sheets or coupons, among others.

Figure 38:
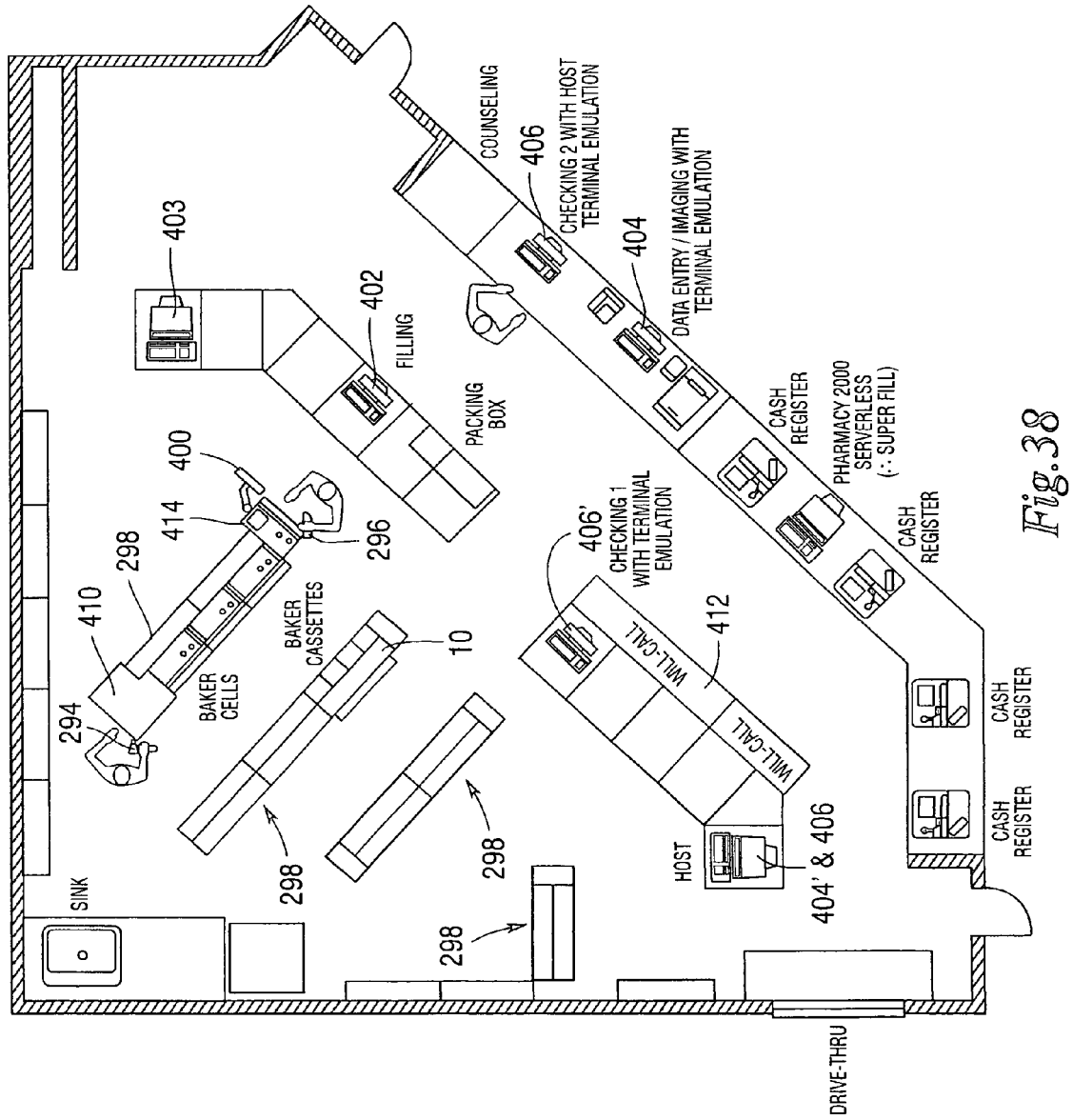
FIG. 38 illustrates a typical pharmacy layout utilizing a medicament dispensing cabinet of the present invention.

FIG. 38 illustrates a layout of a typical pharmacy utilizing the medicament dispensing cabinet 10, open shelving 298, dispensing computer 400, cordless bar code scanner 294 (RF, IR, ultrasonic, etc.), handheld computer or handheld computer which incorporates a bar code scanning device 296, filling workstation 402, pharmacy system 403, data entry workstation 404, pharmacist checking workstation 406, inventory workstation 410, an area for completed prescriptions generally known as 'will call' area 412 and a check out station 414. Additionally, one or more duplicate medicament dispensing cabinets 10, dispensing computers 400, filling workstations 402, pharmacy systems 403, data entry workstations 404, pharmacist checking workstations 406, inventory workstations 410, 'will call' areas 412 and check out stations 414 are also intended to be within the scope of the present invention, which may be used to simultaneously interact to properly fill and verify patient prescriptions. For example, multiple medicament dispensing cabinets 10, cordless bar code scanners 294 and handheld computers or handheld computers 296 which incorporates bar code scanning devices may be used simultaneously to properly replenish, operate and maintain the removable dispensing device 12 and dispensing cell 16.

Figure 39:
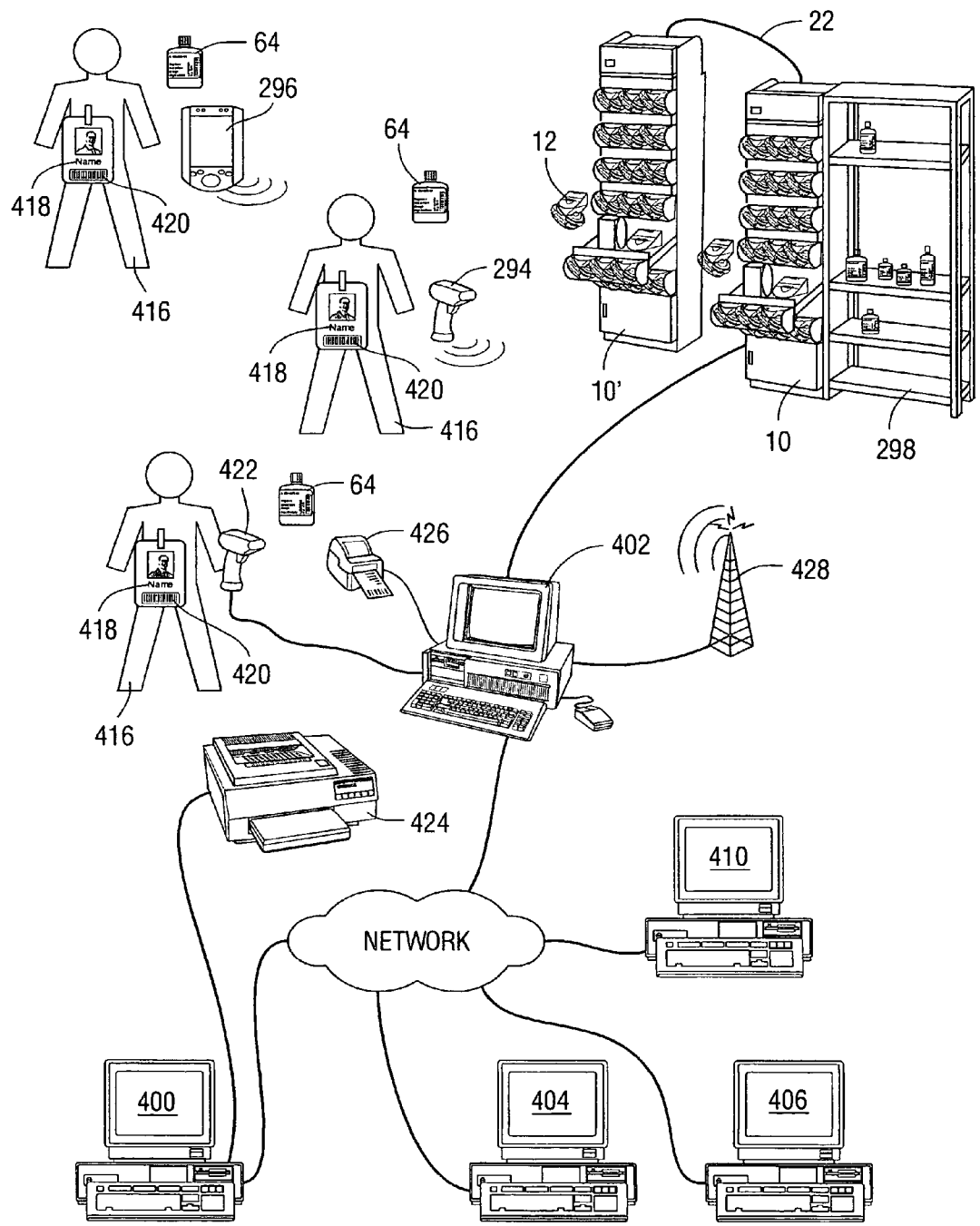
FIG. 39 illustrates a pharmacy computer system and medicament dispensing cabinets.

Turning to FIG. 39 each worker 416 in the pharmacy is assigned an identification badge 418 or bracelet (not shown) which contains bar code indicia 420 that can be scanned by a bar code reader 422, cordless bar code reader 294 or handheld computer or handheld computer which incorporates a bar code scanning device 296 or can be manually entered into one of the computers. FIG. 39 further illustrates a medicament dispensing system showing the various workstation configurations and functional interconnection of the components as they are used to implement the processes of filling a patient prescription, replenishing the removable dispensing devices 12, and maintaining or cleaning the dispensing devices 12. In the present embodiment, the filling workstation 402, dispensing computer 400, and the remainder of the pharmacy computer system are interconnected via a network providing intercommunication of files, data and instructions among the connected computers and workstations. In addition, the remainder of the pharmacy computer system may be further comprised of the data entry workstation 404, checking workstation 406, inventory workstation 410, and a printer 424.

In the present embodiment, the filling workstation 402 comprises a computer, display, and keyboard although, as previously mentioned, the terms "computer", "workstation" or the like are to be construed to mean any type of control device. The filling workstation 402 is responsive to the bar code reader 422 and may control a printer such as prescription label printer 424. A radio frequency transmitter/receiver 428 may be provided for communication with the cordless bar code scanner 294 and the handheld computer or handheld computer which incorporates a bar code scanning device 296. The filling workstation 402 is connected to a first medicament dispensing cabinet 10 by the cable 20. Additional medicament dispensing cabinets 10' may be connected to the first medicament dispensing cabinet 10 by the cable 22.

Figure 40:
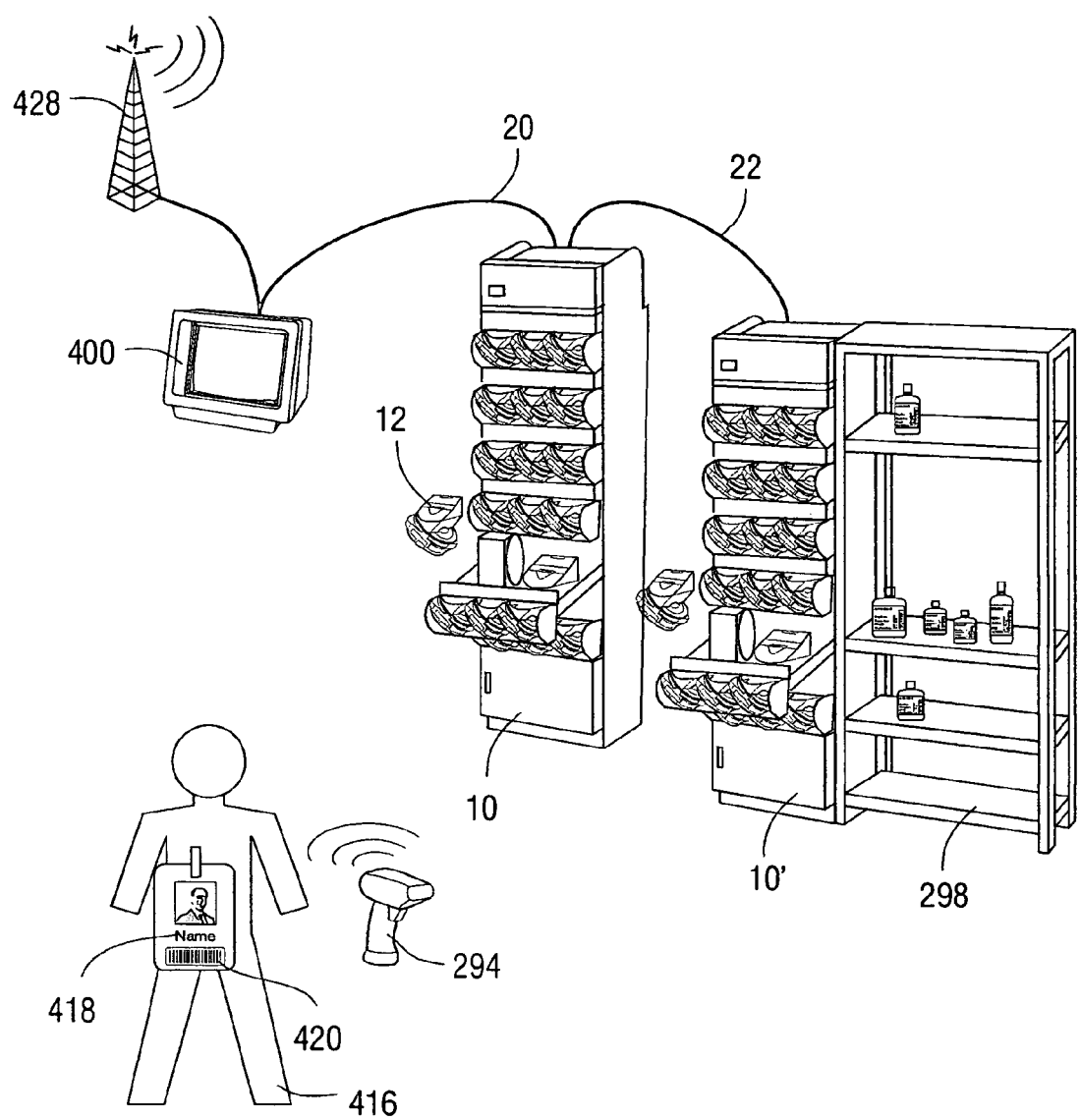
FIG. 40 illustrates a dispensing computer utilizing a cordless bar code scanner in conjunction with dispensing cabinets and open shelving.

FIG. 40 is an illustration of a medicament dispensing system showing the filling workstation 402 implemented by utilizing a dispensing computer 400 to control the processes of filling a patient prescription, replenishing the removable dispensing devices 12, and maintaining or cleaning the dispensing devices 12. In the present embodiment, the dispensing computer 400, and pharmacy computer system are interconnected via a central network providing intercommunication of files, data and instructions. The dispensing computer 400 is further connected to the radio frequency transmitter/receiver 428 for communication with, for example, cordless bar code scanner 294 and handheld computer or handheld computer which incorporates a bar code scanning device 296. The dispensing computer 400 may control the prescription label printer (not shown in FIG. 40). It should be apparent to those skilled in the art, however, that some of the components may be combined while remaining within the scope of the present invention. For example, the dispensing computer 400, radio frequency transmitter/receiver 428, and medicament dispensing cabinet 10 may be combined into a single unit to perform the same operations.

For simplicity of discussion, the filling workstation 402 and dispensing computer 400 as illustrated in FIGS. 39 and 40, respectively, are shown as separate components. Is should be apparent to those skilled in the art, however, that the functions of the filling workstation 402 and dispensing computer 400 are similar in scope and in general are interchangeable with each other. Additionally, although in the embodiments shown, workers 416 identify themselves by badges or bracelets carrying bar codes, other forms of identification may be used including radio frequency (RF) tags, among others.

Figure 41:
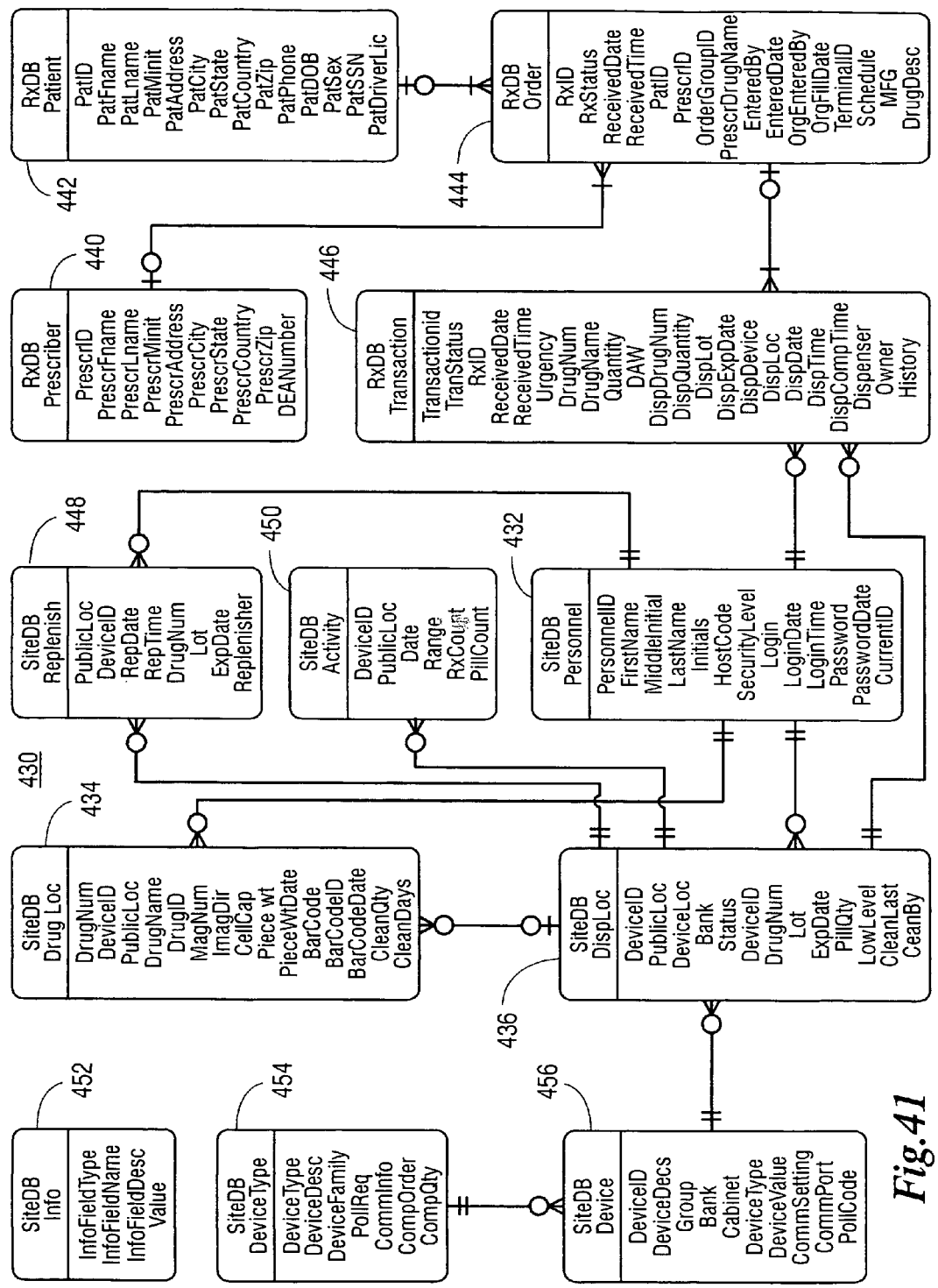
FIG. 41 illustrates a database which may be used in conjunction with the pharmacy computer system shown in FIG. 39.

FIG. 41 is a representation of a database 430, utilized by the dispensing computer 400 and by the pharmacy workers. The database 430 has several fields, certain of which represent specific information about a specific worker. The database 430 has a personnel database 432 which includes fields representing the worker's name or initials, password, badge or bracelet indicia, worker classification or security level, medicament access security level, among others. Each worker is also assigned configurable settings that allow them the ability to fill prescriptions, replenish or access the removable dispensing devices 12, and retrieve another worker's fill prescription request.

The worker classification may be selected from a group which comprises a pharmacy technician, inventory clerk, pharmacist, or pharmacy manager (sometimes collectively referred to as a pharmacy worker). Each worker classification allows the worker to access or perform different functions or procedures within the dispensing computer 400. In addition, the worker classification defines a hierarchy to operating the dispensing computer 400. The pharmacy manager has the highest security level and is allowed access to all dispensing computer functions, including maintaining workers and their worker classifications. The pharmacist reports to the pharmacy manager and has the ability to perform tasks and override errors created by either a pharmacy worker or inventory clerk or other pharmacist but is restricted from modifying the worker database or each worker's classification. The pharmacy worker is allowed to operate the dispensing computer 400 to fill patient prescriptions; but may not be given access to all medicaments or may not be given the ability to replenish the removable dispensing devices 12 or perform maintenance (including cleaning) of dispensing cells 16, collectively referred to as servicing. The inventory clerk is allowed to replenish the dispensing devices 12, remove and replace removable dispensing devices 12 or return medicament to a dispensing device 12.

In addition, each worker is given a drug access level based on their experience and training. The medicaments used in a pharmacy are classified by the Food and Drug Administration (FDA) as being Over-The-Counter (OTC), prescription (Rx), controlled substance (C2, C3, C4 or C5) or narcotic. These classifications determine the level of training or restrictions in handling while dispensing patient prescriptions or replenishing the removable dispensing device. The dispensing computer 400 maintains two levels of drug access security. If a worker is assigned an access security level of 'Controlled', they may access any medicament within the dispensing system. If a worker does not have the 'Controlled' access security level, the dispensing computer 400 will restrict their access to only the OTC or prescription drugs. The dispensing computer 400 will check the access level required for all medicaments in an entire dispensing drawer 14 before the worker will be allowed access. If the drawer contains a 'Controlled' medicament and the worker does not have access to 'Controlled' medicaments, the worker will not be allowed to replenish, clean or maintain the removable dispensing device 12 or dispensing cell 16 requested by the worker. The allocation of responsibility/access may change from pharmacy to pharmacy or periodically within a pharmacy. Security can thus be individualized based on employees as discussed above or based on dispensers (dispensing cell 16 plus dispensing device 12) as discussed below.

The dispensing computer 400 also maintains a database 434 of each medicament that may be dispensed from the medicament dispensing cabinet 10. Each medicament is assigned a drug access level that corresponds to the user drug access level. The medicament database is typically maintained only by a pharmacist or pharmacy manager.

The dispensing computer 400 also maintains a database 436 for each dispensing cell 16 comprising dispensing cell indicia, e.g. bar code 44, textual drug description for display, textual drug number (NDC or DIN), removable dispensing device indicia 146 (see FIG. 11), medicament stock bottle indicia 287 (see FIG. 36), among others. Each dispensing cell 16 may be associated to several medicament stock bottle indicia 287.

The database 430 also contains a prescriber database 440, patient database 442, order database 444 and transaction database 446. A replenish database 448 and site activity database 450 are provided, as are site information database 452, device type database 454 and site device database 456 as shown in FIG. 41.

As will become more apparent from the description of various processes below, the present invention overcomes the problems inherent in other medicament dispensing units and provides a medicament dispensing cabinet 10 utilizing a removable dispensing device for dispensing specific quantities of bulk medicament 62 to fill a patient prescription. The medicament dispensing cabinet 10 may utilize any of a wide variety of displays to display and insure the proper pharmacy worker is retrieving the proper medicament from the dispensing cell 16 for the patient prescription being filled by the dispensing cell 16. For example, each medicament dispensing cell 16 may contain the alpha-numeric display 38 for indicating the worker's identification by displaying either the worker's initials or another code that is easily recognized by the pharmacy worker.

The medicament dispensing cell 16 may use the display 38 for clearly communicating various types of information to the pharmacy worker. When operating in various secure modes, the drawer locking mechanism may be used for limiting access to the dispensing cell 16 and removable dispensing device 12. The electronically controlled chute gate 34 and gate release 36 may be used to insure medicament retrieval by the proper pharmacy worker 416. The dispensing cell label 42 with bar code indicia 44 may be used to positively identify the dispensing cell 16, removable dispensing device 12, and medicament 62. The medicament dispensing cabinet 10 of the present invention includes a means to positively indicate the current state of each dispensing cell 16 which includes displaying the operation being performed, the pharmacy worker associated with the task to be performed and other state specific information needed by the pharmacy worker to efficiently operate the medicament dispensing equipment. However, the dispensing cell 16 can also be operated in a "Baker Cell mode" in which the dispensing cell 16 simply counts medicament.

Figure 42:
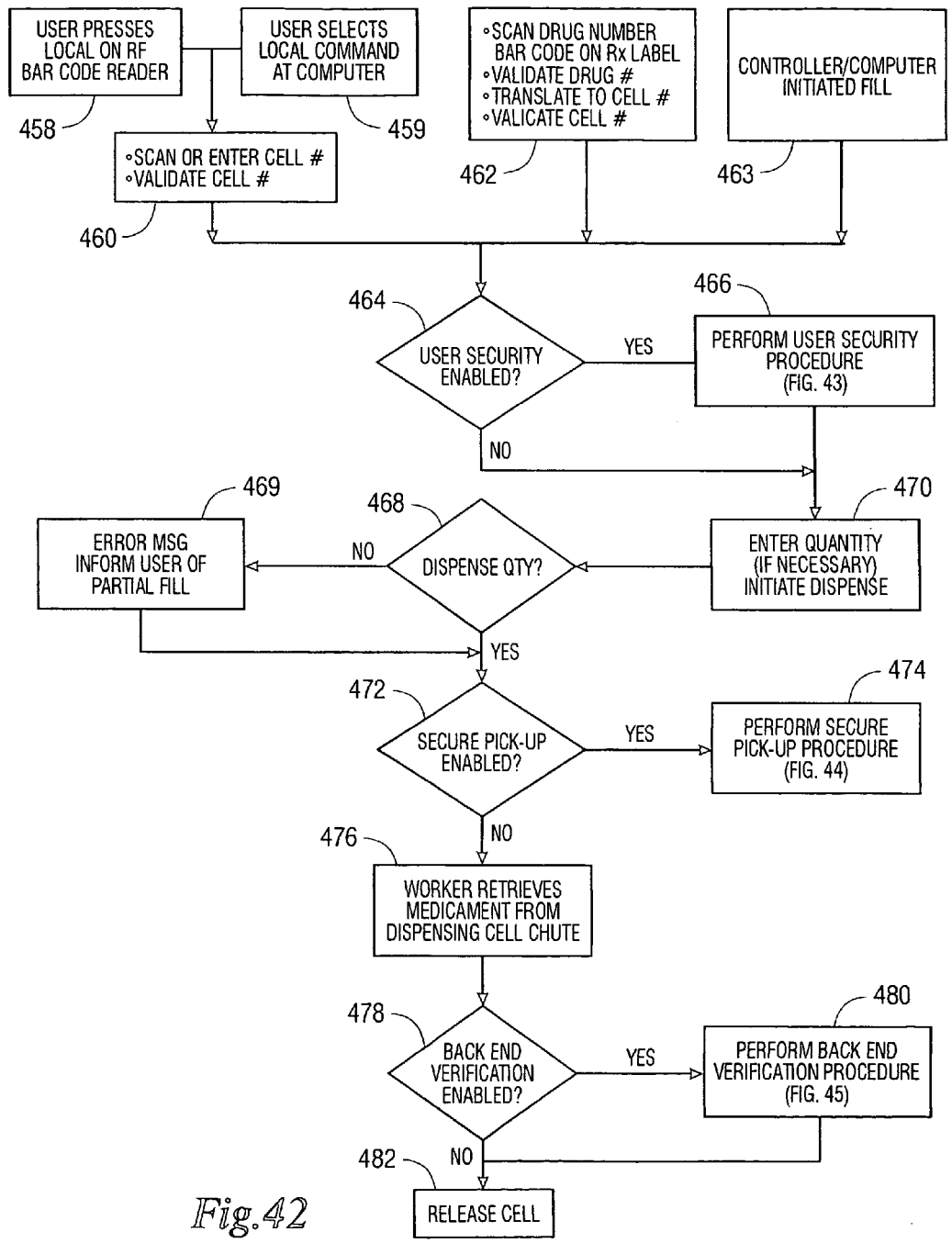
FIG. 42 is a high level flow chart illustrating a patient prescription filling process.

Now referring to FIG. 42, the present invention includes a method for directing and tracking the patient prescription filling process and verifying the proper steps are taken by a pharmacy worker and recording the medicament and prescription filling details which occur during the patient prescription filling process. During normal operation of the medication dispensing cabinet 10, the dispensing cell 16 is idle, waiting for instruction, e.g. from the dispensing computer 400.

The prescription filling process may be initiated in one of several ways as shown in FIG. 42. As shown at 458, a user may press the "local" button on a cordless bar code reader followed by scanning or entering a cell number at 460. Additionally, the process could begin by entering a command on a host computer or controller to enter the "local" mode as shown at 459. Thereafter, the system validates the cell number. Alternatively, as shown in block 462, the user may scan a drug number bar code on a prescription label which causes the system to validate the drug number, translate the drug number to the appropriate cell number, and validate the cell number. Alternatively, prescription filling could be initiated electronically by a host computer, or a controller such as the AutoLink™ controller (available from McKesson Automation Systems) as shown at 463.

From either block 460, 462, or 463 the system then determines if user security is enabled at 464. If user security has been enabled, then a user security procedure is performed as shown by block 466. That procedure is described in detail in conjunction with FIG. 43. After performance of the user security procedure, or if the user security was not enabled, the process proceeds with block 470. When the patient prescription is to be dispensed by a dispensing cell 16, the dispensing computer 400 instructs the appropriate dispensing cell 16 of the proper quantity of medicament 62 to dispense at 470. As the medicament 62 is dispensed, the cell display 38 associated with the dispensing cell 16 indicates the present quantity dispensed into the chute 32 located in the dispensing cell 16.

When the patient prescription dispensing is complete, a determination is made at step 468 as to whether the entire quantity was dispensed. If the entire quantity was dispensed, the pharmacy worker 416 is notified by the drawer controller 46 through the illumination of the 'READY' annunciator LED 40 or displaying a message on the cell display 38. If the entire quantity was not dispensed, an error message is displayed at 469 and the worker is advised that the prescription was only partially filled. After 469, or if the query at 468 is answered in the positive, the process continues with decision 472 where a determination is made if the secure pick up procedure is enabled. If yes, the secure pick up procedure is performed as shown by block 474 and described in detail in conjunction with FIG. 44. After the secure pick up procedure has been performed, or if the secure pick up procedure has not been enabled, the worker retrieves the medicament from the dispensing cell chute as shown by 476.

Based on the security configuration settings maintained by the dispensing computer 400, the dispensing cell's gate release 36 is enabled after the appropriate worker and dispensing cell identification security checks have been completed. Once these security verification checks have been successfully completed, the pharmacy worker 416 may press the gate release 36 (with the prescription vial 30 under the chute 32), which opens the electronically operated dispensing chute gate 34, allowing the medicament 62 to fall from the dispensing cell's chute 32 into the patient's prescription vial 30.

Completing the description of the workflow illustrated in FIG. 42, after the worker retrieves the medicament, a determination is made at block 478 if a back end verification procedure has been enabled. If the procedure has been enabled, it is performed as shown by block 480 and described in detail in conjunction with FIG. 45. After the performance of the back end procedure or if the back end procedure has not been enabled, the cell is released at 482.

Figure 43:
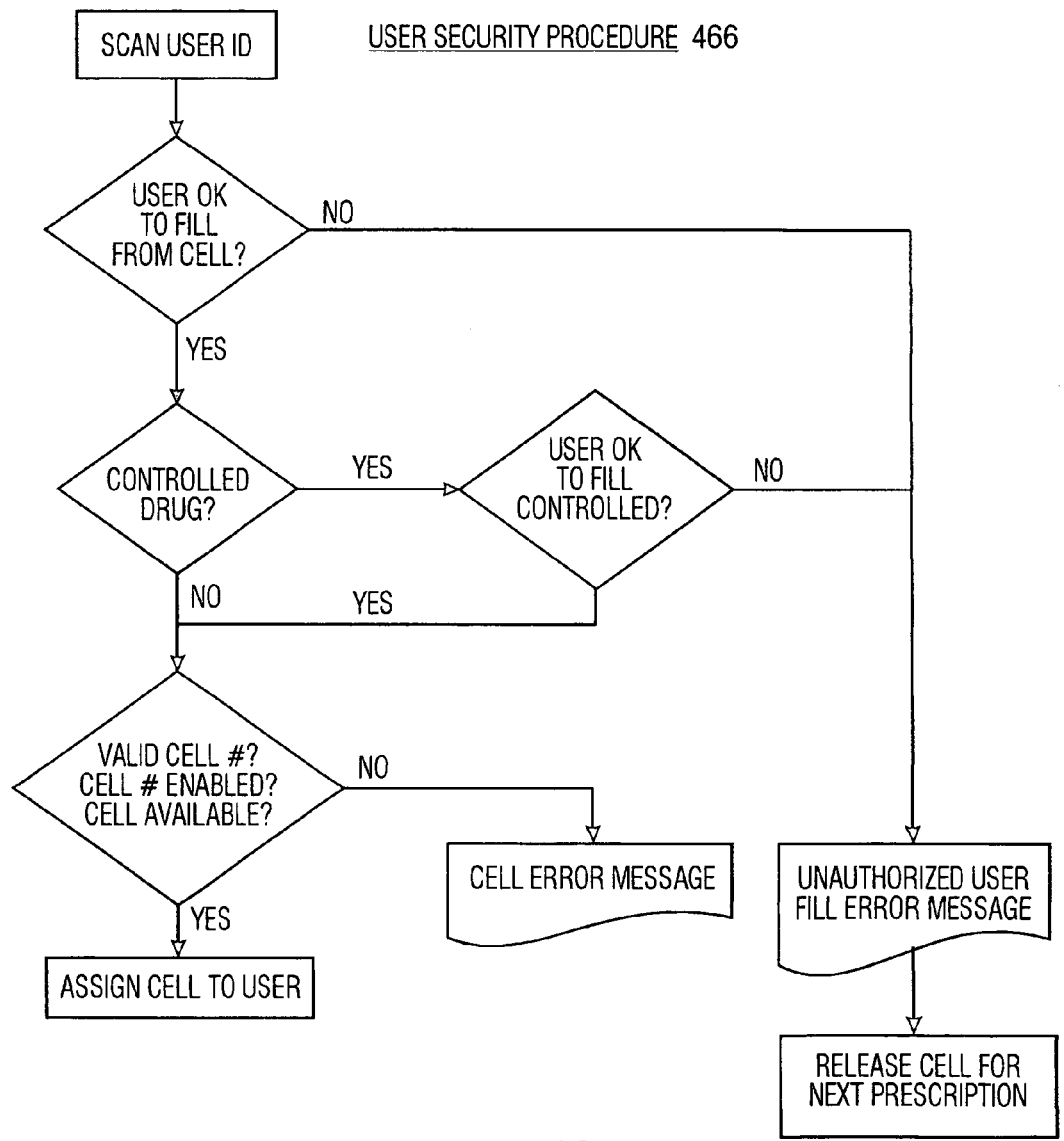
FIG. 43 is a flow chart illustrating the user security process shown in FIG. 42.

The user security procedure 466 is illustrated in FIG. 43 and is used to insure the worker security level will allow the worker to dispense medicament from a dispensing cell 16 based on medicament configuration settings maintained in the database in, e.g. the database 430. After the worker has initiated a medicament to be dispensed by one of the several methods illustrated in FIG. 42, the dispensing computer 400 directs the worker to scan their worker bar code indicia 420 on their identification badge 418 or bracelet. Other forms of user identification that could be implemented are an RF tag assigned to each user, fingerprint recognition, retinal scan, or other alternatives known in the art to specifically and uniquely identify an individual. The dispensing computer 400 will verify the pharmacy worker 416 has a medicament access level sufficient to dispense the medicament from the dispensing cell 16 by going through the following sequence of questions:

User OK to fill from cell?
Controlled drug? If yes, is user OK to fill this controlled drug?
Valid cell number?
Cell number enabled?
Cell available?

If the worker has the correct medicament access level, and the cell number is valid, enabled and available, the dispensing cell 16 is temporarily assigned to the worker, if not, the cell is released.

Figure 44:
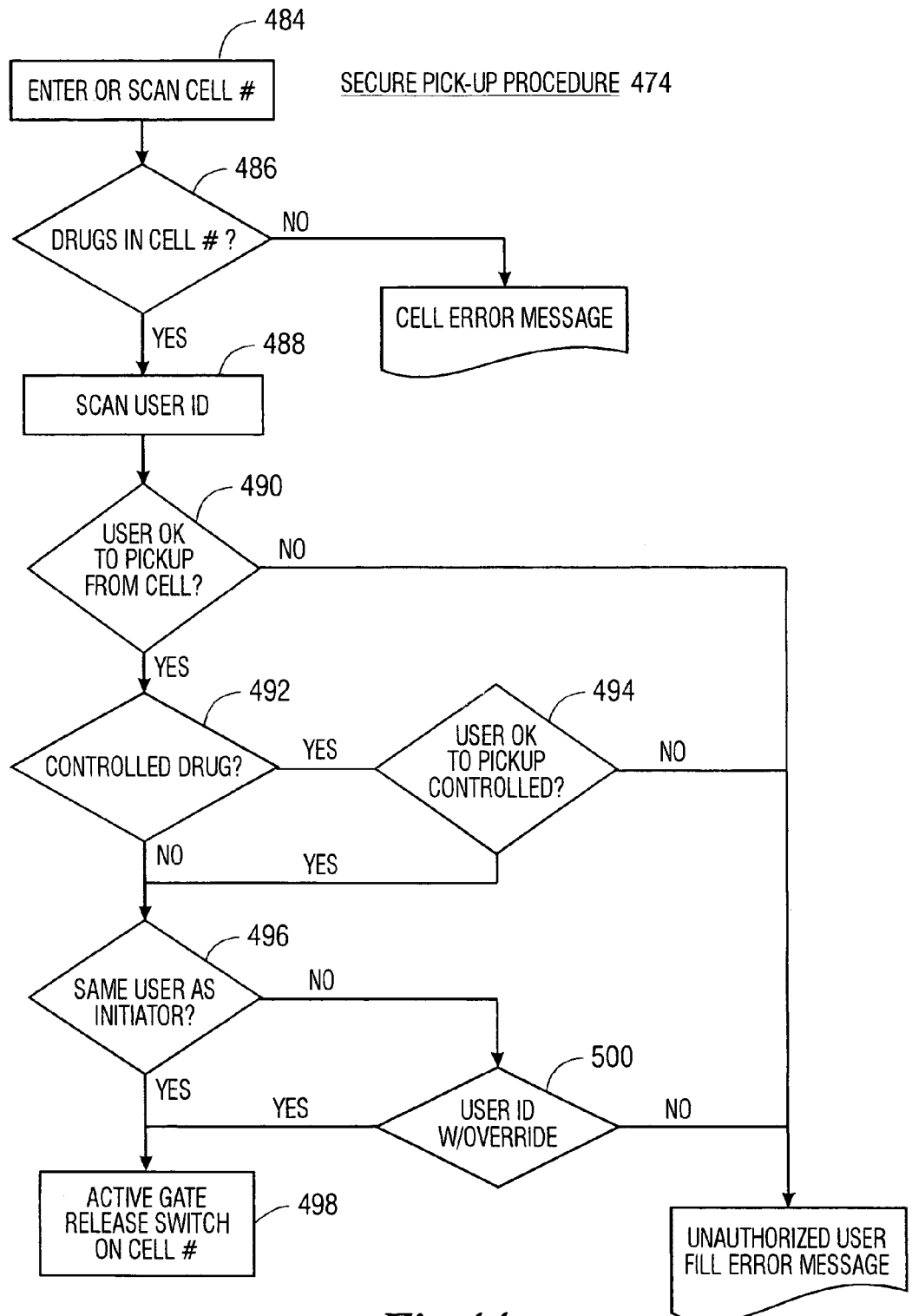
FIG. 44 is a flow chart illustrating the secure pick-up procedure shown in FIG. 42.

The steps required for verifying the pharmacy worker or pharmacist which originally initiated the dispensing event and for verifying that the cell 16 has the proper medicament access level, i.e. the secure pick up procedure 474, are shown in FIG. 44. The worker is instructed by the dispensing computer 400, cordless bar code reader 294, or handheld computer or handheld computer which incorporates a bar code scanning device 296 at 484 to scan the dispensing cell bar code indicia 44 to identify the dispensing cell 16 from which medicament 62 is being retrieved by the pharmacy worker. If the identified dispensing cell 16 contains medicament ready for pick up as shown at 486, the dispensing computer 400 then directs the worker to scan the worker bar code indicia 420 of the worker's identification badge 418 or bracelet at 488. The dispensing computer 400 verifies at 490, 492 and 494 that the medicament access level of the worker will allow retrieval of the medicament in the dispensing cell 16. The dispensing computer 400 then verifies if the worker picking up the dispensed medicament is the same worker that initiated the dispensing event by checking if the dispensing cell was temporarily assigned to this worker at 496. If there is a match, the dispensing computer 400 will enable the gate release 36 by sending instructions to the drawer controller 46 at 498. If the worker did not originally initiate the dispensing event, the dispensing computer must check the worker database configuration setting to verify the worker seeking to retrieve the medicament has permission to retrieve a patient prescription initiated by another worker. If the worker is allowed to pick up another worker's prescription as shown at 500, the gate release 36 is enabled for the dispensing cell 16.

During continued use of the medication dispensing cell 16, the status of the dispensing cell may change and this state change may be indicated on the appropriate dispensing cell annunciator LED 40 and/or the cell display 38. The dispensing cell 16 may indicate to the pharmacy worker 416 when the removable dispensing device 12 should be replenished by illuminating the 'MAINTENANCE' annunciator LED 40 and also displaying additional replenishment message information on the cell display 38. Should a problem be detected in the dispensing cell 16 or dispensing device 12, need for this type of service may be indicated using the 'ERROR' annunciator LED 40 in combination with messages displayed on the cell display 38.

In some extremely busy pharmacies, the patient prescription filling task is subdivided further and requires the dispensing computer 400 to allow a first pharmacy worker to initiate the medicament dispensing while a second pharmacy worker retrieves the medicament 62 from the dispensing cell 16 upon completion as shown in FIG. 44. As discussed above in conjunction with FIG. 41, the dispensing computer 400 maintains a pharmacy worker database 432 of security levels for each worker that may be set which allows a worker to retrieve medicament from the dispensing cell initiated by another worker. This capability allows a second pharmacy worker to initiate the secure pickup of a patient's prescription from a dispensing cell while maintaining the verification and pharmacy worker auditing trail needed in busy pharmacies. The same security level for both fill and pickup can be enabled or disabled independently.

Another level of pharmacy worker auditing captured by the dispensing computer 400 or other computer within the pharmacy network is the back end verification procedure shown in FIG. 45. That procedure requires the pharmacy worker identification bar code indicia 420 to be scanned immediately after the medicament 62 retrieval from the dispensing cell 16 as shown in FIG. 45 at 502. The dispensing computer 400 receives a signal from the medicament dispensing cabinet 10 indicating the dispensing cell 16 from which medicament 62 was retrieved. This signal is associated with the pharmacy worker 416 identified by the worker identification badge scanned and verifies the correct pharmacy worker retrieved the patient prescription. The user ID is assigned to the filled and picked up prescription as shown at 503.

The back end verification procedure can be expanded to allow the worker the capability to instruct the dispensing computer 400 when the medicament 62 retrieved from the dispensing cell 16 will be returned to the removable dispensing device 12. An example of such a "return to stock procedure" is illustrated in FIG. 45C. This procedure provides the user with a way of dealing with a patient canceling a prescription, a prescription not being picked up, prescription errors that may be caught after the prescription has been initiated for dispensing, or returning stock after a cycle count. The return to stock portion of the back end verification process insures accurate inventory quantity records while also insuring the dispensing device's medicament integrity by directing, tracking and verifying the worker while performing the steps of the return to stock task.

Figure 45A:
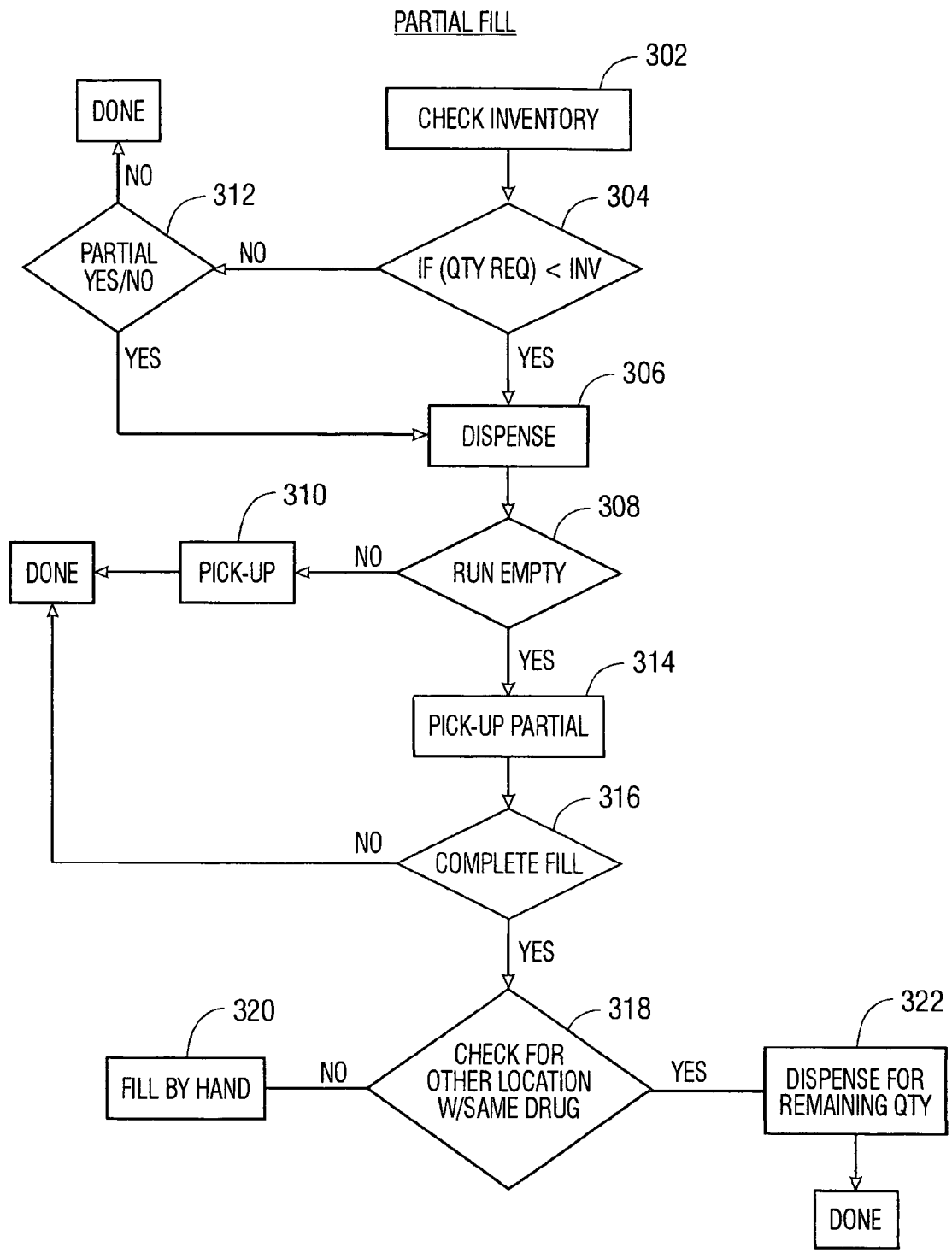
FIG. 45A is a flow chart illustrating a partial fill process.
Figure 45B:
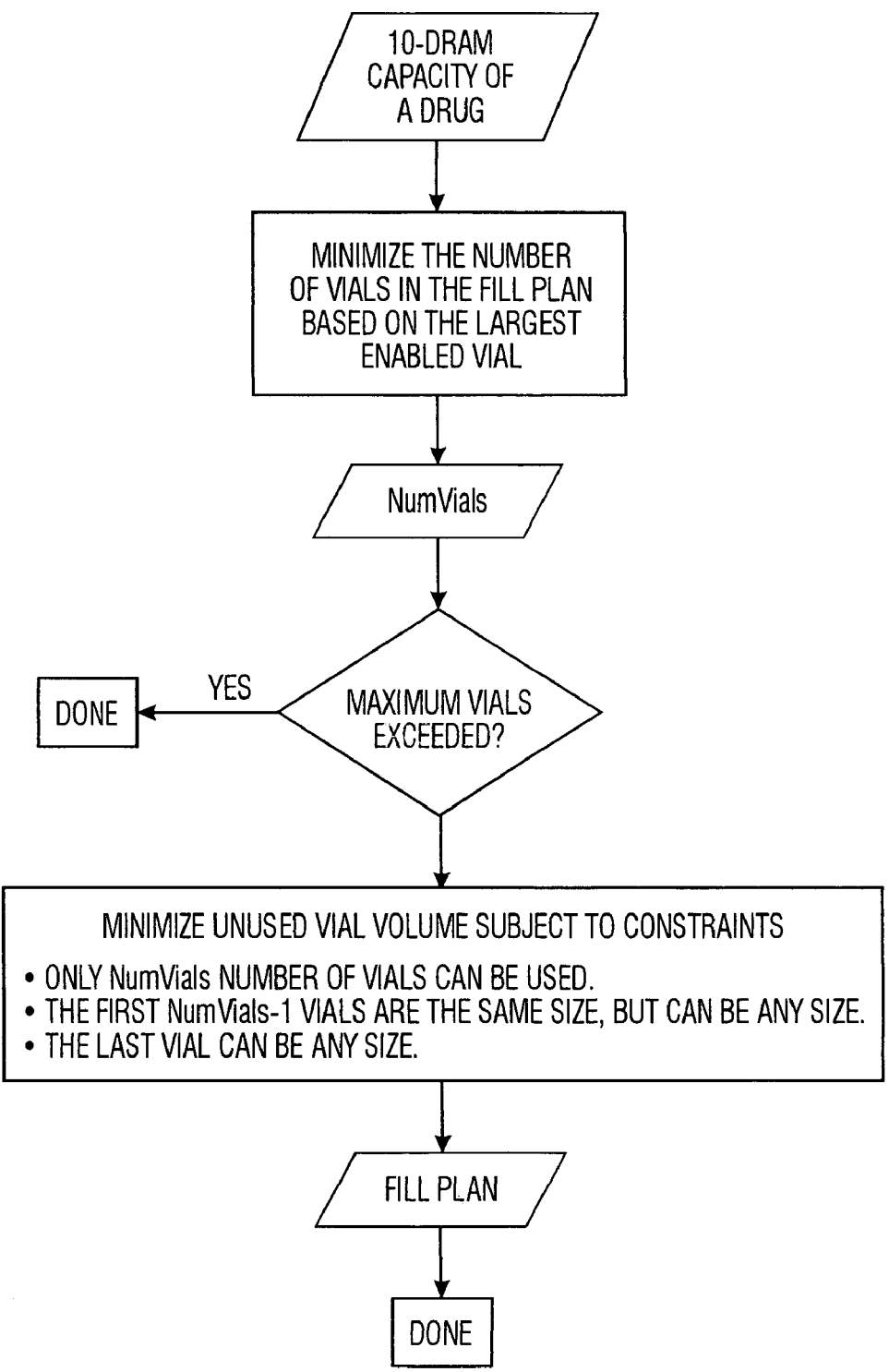
FIG. 45B is a flow chart illustrating a best fit vial sizing process and FIG. 45C is a flow chart illustrating a return to stock procedure.
Figure 45C:
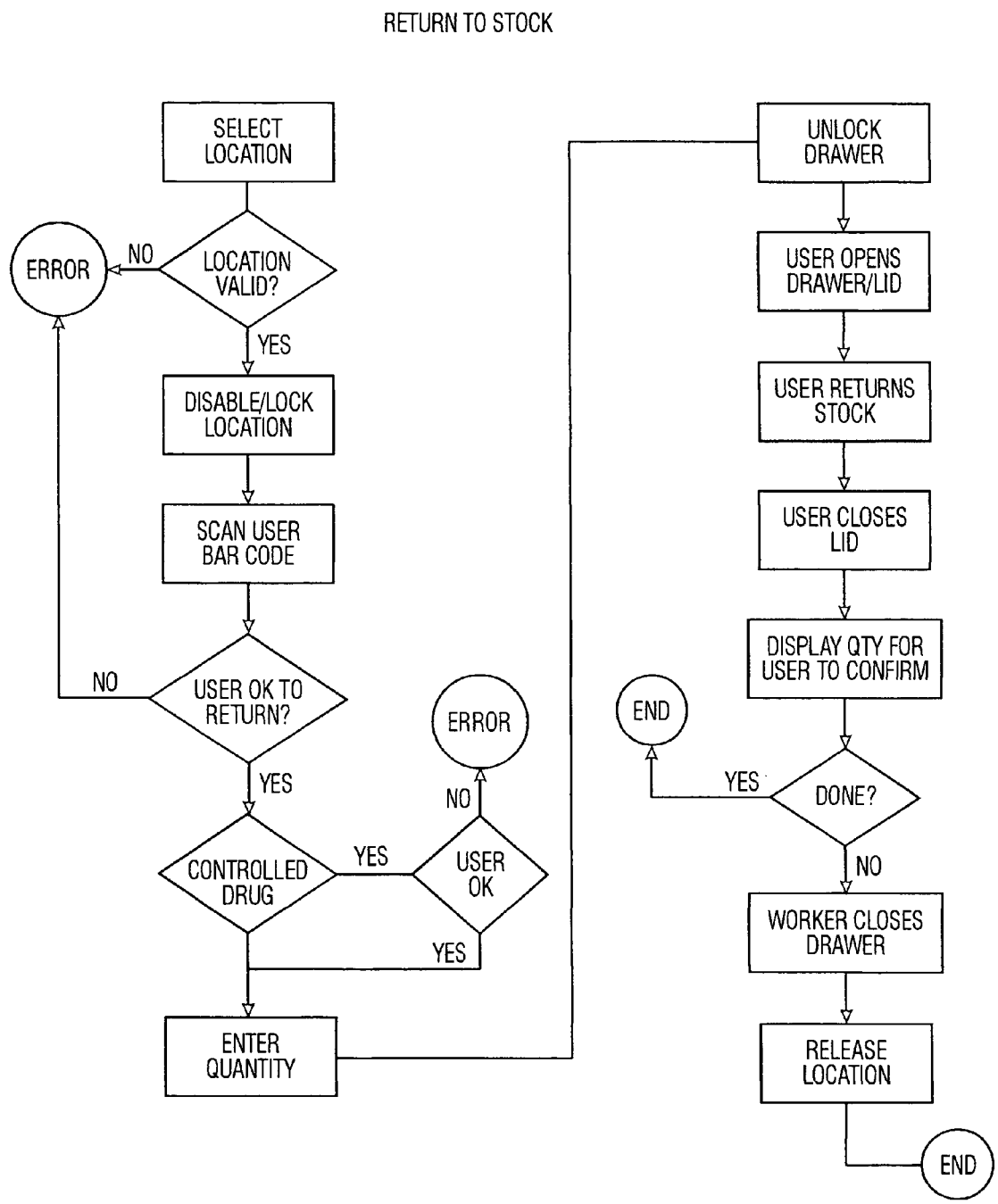

The back end verification procedure can be further expanded to allow the worker to handle partial prescription fills when the dispensing device runs empty while dispensing a patient prescription as shown in FIG. 45A.

In FIG. 45A, after a dispensing location for filling has been selected, and the desired quantity requested, a check is made at 302 to ascertain the inventory at that dispensing location. At 304, if the quantity requested is less than the inventory at that location, a dispensing event occurs at 306. At 308, a decision is made as to whether the dispense ran the inventory at that location to zero. Recall that in 304 the quantity required was determined to be less than the current inventory, so the determination at 308 will be negative leading to a pick up event at 310 followed by the conclusion of the process.

If at 304 the quantity required was equal to or greater than the inventory at the dispensing location, a decision is made at step 312 whether a partial dispense is acceptable. If not, the process terminates with an appropriate message. If a partial dispense is possible, then a dispensing event occurs at 306.

From 306, at decision 308, because the quantity required was greater than the inventory, this dispensing location has been emptied by the partial fill, which may be picked up at 314. A decision is made at 316 if the fill should be completed. If not, the process concludes; if yes, another location with the same drug is searched for at 318. If no automated dispensing device is located, instructions are provided at 320 to complete filling the prescription by hand. If, on the other hand, an automated dispensing device is identified, then a dispensing event occurs at 322 for the remaining quantity. The partial fill process can track the identification of both the worker retrieving the first prescription portion from the dispensing cell 16 and the worker completing the second prescription portion, or the worker retrieving the second prescription portion from another dispensing cell 16, and finalizing the complete prescription before it is checked by the pharmacist. Additional labels for multiple vials can be prepared as needed.

Should a patient prescription require multiple prescription vials 30, the dispensing computer 400 will inform the worker of the vial size needed for each portion of the complete prescription. An example of that process in shown in FIG. 45B. The dispensing computer 400 maintains a site configuration allowing a patient prescription to be broken into 'Best Fit' or 'Same Size' prescription medicament vials. The 'Best Fit' setting would select from the available site medicament vial sizes to best fill a prescription. When multiple vials are required, the largest medicament vial size would be used on the first and subsequent portions; while the smallest medicament vial size needed for the remainder of the prescription would be used on the final portion. The 'Same Size' setting would select from the available site medicament vial sizes to fill the complete prescription and all portions of the prescription would be in the same medicament vial size. The dispensing computer 400 would inform the worker of the vial size to use and the medicament quantity to dispense into each vial. Once all medicament vials 30 with the appropriate quantities were dispensed by a worker, the back end verification process would finalize the prescription as being completely filled and ready for checking by the pharmacist. The dispensing computer 400 maintains a database of medicament vial sizes, volumetric capacity and the recommended fill level. The dispensing computer maintains a medicament volumetric database and the quantity of medicament per volumetric standard which can be used to determine the appropriate vial size for a patient prescription quantity. Various vial combinations may be used, e.g., two medium vials instead of a large and a small vial based on business rules that could include cost, stock on hand, etc. The medicament volumetric database in the dispensing computer may be remotely updated on a periodic basis without intervention by a pharmacy worker.

Figure 46A:
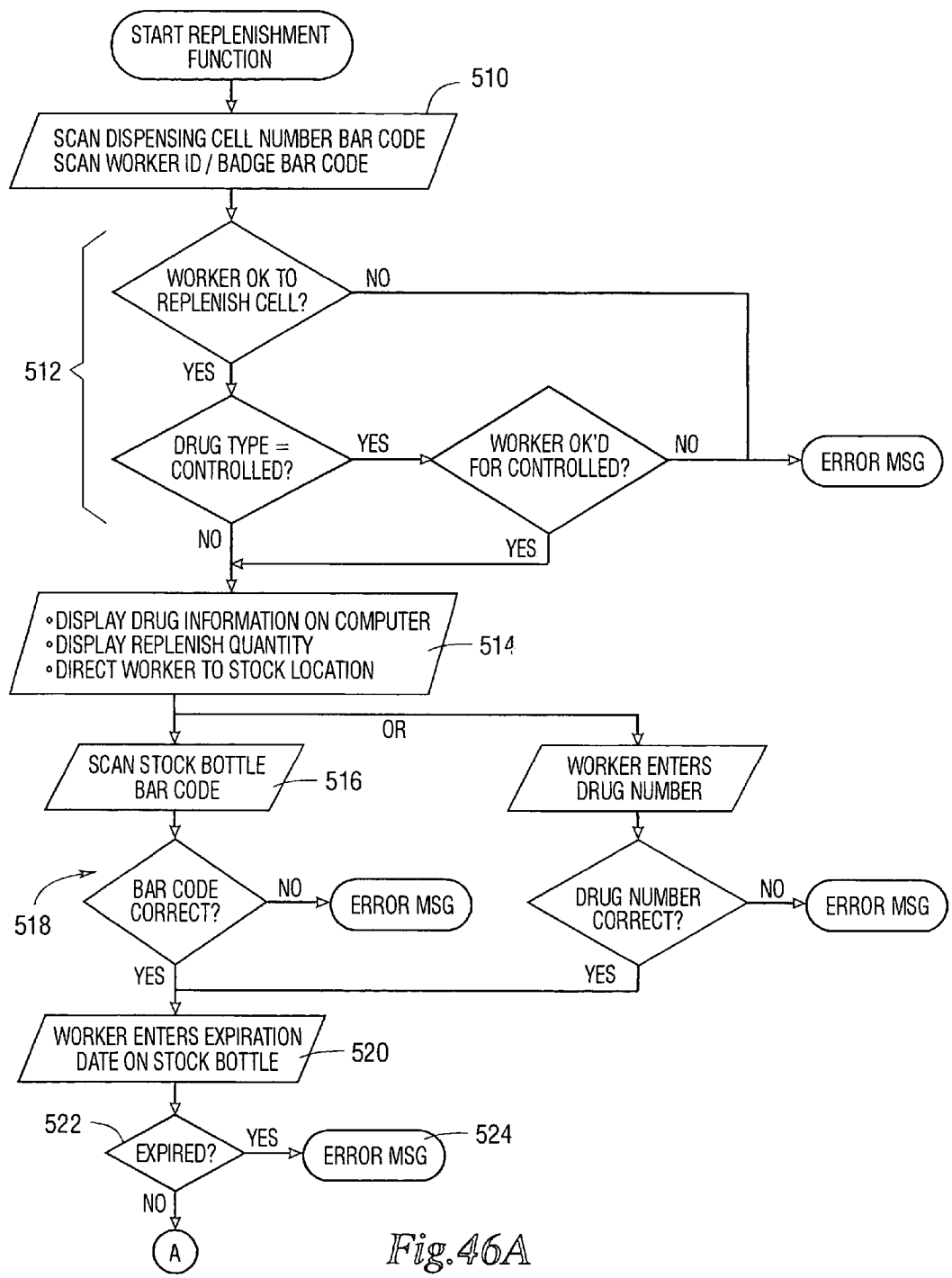
FIGS. 46A and 46B is a flow chart illustrating the dispensing cell and dispensing device replenishment function.
Figure 46B:
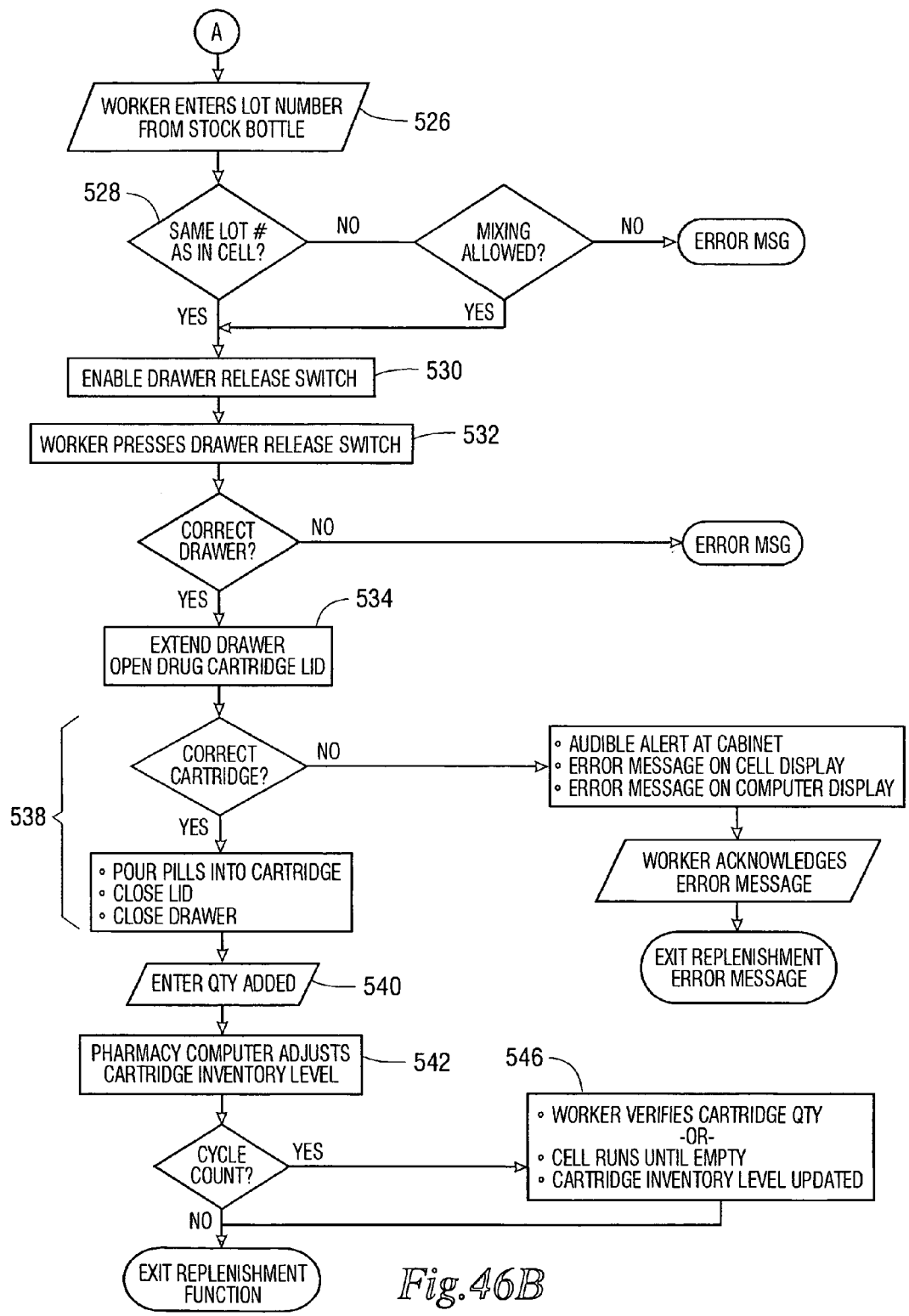

Now referring to FIGS. 46A and 46B, the present invention includes a method for verifying a pharmacy worker 416 correctly replenishes the removable dispensing device 12 in a medicament dispensing cell 16 with the correct medicament 62 retrieved from the pharmacy storage shelves 298. The worker initiates the replenishment procedure on the dispensing computer 400, cordless bar code reader 294 or handheld computer or handheld computer which incorporates a bar code scanning device 296 and is then instructed to scan the dispensing cell bar code indicia 44 on the dispensing cell 16 to be replenished at 510. The worker identification bar code indicia 420 is scanned and the dispensing computer 400 confirms at 512 if the worker is authorized to replenish the identified cell. The dispensing computer 400 displays the recommended replenishment quantity and other medicament information while also directing the worker to the bulk medicament stock shelf 298 within the pharmacy at 514. The dispensing computer 400 insures the correct medicament bulk stock bottle 64 is retrieved from the shelf 298 by requiring the pharmacy worker 416 to scan the bar code 287 located on the bulk stock bottle 64 at 516. The dispensing computer 400 then compares the bulk stock bottle bar code indicia 287 to the information stored in a database of approved bar code indicia values for the appropriate removable dispensing device 12 as shown at 518.

The dispensing computer 400 instructs the worker to enter the expiration date 290 printed on the bulk medicament stock bottle 64 at 520 and then compares the expiration date to the current date at 522. If the bulk medicament has expired, the worker is notified at 524 and prevented from replenishing the removable dispensing device 12. By checking the expiration date, the dispensing computer 400 insures the medicament 62 is not repackaged into patient prescriptions if it is beyond the expiration date.

The dispensing computer 400 instructs the worker to enter the lot number 289 printed on the bulk medicament stock bottle 64 at 526. If the current removable dispensing device 12 inventory quantity is not zero, the lot number of the medicament remaining in the dispensing device 12 at 528 is compared to the lot number 289 entered by the worker. If the two lot numbers do not match, the dispensing computer 400 must check a medicament dispensing system configuration setting for allowance of mixed lot numbers. If the mixing of lot numbers is not allowed, the worker is prevented from replenishing the dispensing device 12. By the dispensing computer 400 preventing mixing of medicament lot numbers 289, the pharmacy can accurately track the specific medicament lot number 289 used to dispense a patient prescription should the medicament be recalled by the manufacturer.

The pharmacy worker 416 and dispensing cell 16 are indicated by corresponding bar code scans of the pharmacy worker identification badge 418 and dispensing bar code indicia 44, respectively. The dispensing computer 400 confirms the pharmacy worker 416 is authorized to replenish the identified cell and can access all other dispensing devices 12 in the same dispensing drawer, and the correct medicament is available for the dispensing device 12 replenishment before unlocking the medicament dispensing drawer 14 through the process described above.

Once the dispensing cell 16 identification, pharmacy worker 416 identification, bulk medicament stock bottle 64 identification, expiration date 290, and lot number 289 have been entered and verified, the dispensing computer 400 will instruct the drawer controller to enable the drawer release switch 386 as shown at 530. The pharmacy worker 416 then has access to the removable dispensing device 12 to be replenished by pressing the drawer release switch 386 (see block 532) which actuates the electronic drawer locking mechanism into the unlocked position allowing the dispensing drawer 14 to be extended from the cabinet 10 as shown at 534.

The medicament dispensing drawer controller 46 and cabinet controller 18 monitor the drawer position switch 388 to confirm when a dispensing drawer 14 is unlocked and extended from the cabinet 10 far enough to change the state of switch 388. The dispensing drawer and cabinet controllers monitor the dispensing device switch 66 while the medicament dispensing drawer 14 is unlocked and extended from the cabinet to insure the correct dispensing device 12, and only the correct dispensing device 12, is opened for replenishment as shown at 538. The worker has the option of removing the dispensing device 12 from the dispensing cell 16 to better position the removable dispensing device 12 in a more convenient location or position for pouring medicament 62 from the stock bottle 64 and then returning the removable dispensing device 12 to the dispensing cell 16. The dispensing computer 400 records the actions of the pharmacy worker 416 and will not dispense a patient prescription from a dispensing device 12 incorrectly opened during the replenishment process. Once the pharmacy worker has replenished the dispensing cell 12, the drawer controller 46, cabinet controller 18 and dispensing computer 400 monitor the dispensing device switch 66 and the drawer position switch 388 to insure the dispensing cell lid 68 is closed and the drawer 14 returned to the closed and locked position, respectively, before dispensing medicament from the dispensing cells within the drawer.

The dispensing computer 400 instructs the pharmacy worker 416 to either accept the default replenishment quantity maintained in the dispensing computer medicament database or enter the quantity of medicament added at 540. The dispensing computer increases the dispensing cell inventory level by the quantity added and maintains this value in the dispensing computer medicament database at 542.

If during the replenishment procedure, and assuming appropriate security measures are set to "on", should the worker inadvertently open an incorrect removable dispensing device 12, the dispensing computer 400 will require a pharmacist to correct the error. This insures the medicament 62 within each dispensing device 12 is correct. The dispensing computer 400 will not dispense a patient prescription from either the dispensing cell associated with the dispensing device that should have been replenished or the dispensing cell associated with the dispensing device that was incorrectly opened by the pharmacy worker during the replenishment process. The corrective actions taken by the pharmacist will be recorded by the dispensing computer 400. The dispensing computer records the pharmacist identification provided by a bar code scan of the pharmacist's identification badge 418 and the pharmacist scanning the dispensing cell bar code indicia 44 from each dispensing cell checked or corrected by the pharmacist.

The pharmacy worker 416, e.g. inventory clerk, may initiate the cycle count procedure shown in FIG. 46B for a particular dispensing cell 16. The worker is guided through the steps as shown in the box labeled 546 to empty the removable dispensing device 12 of medicament 62 by the dispensing cell 16 operating and dispensing all medicament into the chute 32 for retrieval by the worker into a temporary container. The drawer controller 46 will pause the operation of the dispensing cell should it dispense a quantity equal to the maximum capacity allowed in the chute 32. The worker will be instructed to remove the medicament from the chute by pressing the gate release 36 with the temporary container under the chute. The drawer controller 46 will resume the inventory cycle count process once the worker has released the gate release 36 and the gate open sensor 59 detects the chute gate 34 is in the closed position. When the drawer controller 46 has detected the removable dispensing device 12 is empty, the drawer controller 46 will stop the dispensing and instruct the worker to retrieve the medicament from the chute 32. The cell display 38 will indicate the total quantity dispensed during the cycle count procedure. The drawer controller 46 and cabinet controller 18 report the total quantity to the dispensing computer 400 and the worker will be allowed to accept this quantity as the correct inventory quantity for the dispensing cell 16. The dispensing computer 400 will record any variances for future processing or reporting. The worker is instructed to return the entire medicament dispensed during the cycle count procedure back into the removable dispensing device 12. At this time, the inventory value maintained in the dispensing computer is in agreement with the physical inventory stored in the dispensing cell 16. The dispensing computer 400 monitors and tracks the worker and each step during the inventory cycle count procedure until the dispensing drawer 14 is returned to the fully closed position within the cabinet 10 and is in the locked position.

In summary, the dispensing computer 400 will direct, track and verify the worker during the replacement of the dispensing device 12 into the dispensing cell 16. The dispensing computer directs the worker to identify the dispensing device 12, dispensing cell 16 and worker by scanning each item's unique bar code indicia. The dispensing computer then directs the worker to the dispensing cell, illuminates the 'MAINTENANCE' annunciator LED 40, displays an appropriate message on the cell display 38 and unlocks the dispensing cabinet drawer 14 containing the dispensing cell 16. The dispensing computer 400 verifies the worker is allowed to access the dispensing device 12 identified by the dispensing cell bar code indicia 44 and all other dispensing devices in the dispensing drawer before unlocking the dispensing drawer. The dispensing computer monitors the dispensing device switch 66 to insure the proper dispensing device 12 was opened or inserted into the proper dispensing cell 16.

Figure 47:
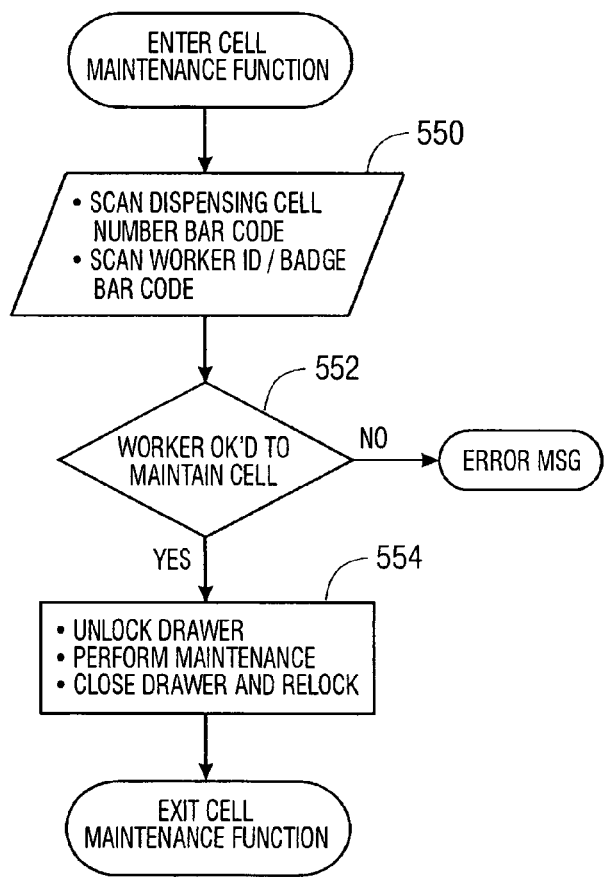
FIG. 47 is a flow chart illustrating a maintenance function.

The dispensing computer 400, or other computer within the pharmacy system, indicates to the pharmacy worker 416 when each dispensing cell 16 requires cleaning to maintain optimal dispensing cell performance. The dispensing computer 400 maintains two cleaning cycle fields for each dispensing cell. See FIG. 41 database 434. The first cleaning cycle field is the quantity of medicament to be dispensed from the removable dispensing device 12 before the 'MAINTENANCE' annunciator 40 is illuminated, indicating to the worker the dispensing cell should be cleaned. The second cleaning cycle field is the number of days between each cleaning cycle. Once the dispensing computer determines the dispensing cell has not been cleaned in this number of days, the 'MAINTENANCE' annunciator LED 40 is illuminated. The pharmacy worker 416 may initiate the cleaning procedure from the dispensing computer 400, cordless bar code scanner 294 or handheld computer or handheld computer which incorporates a bar code scanning device 296. Referring to FIG. 47, the worker will be instructed to scan the dispensing cell bar code indicia 44 for the removable dispensing device 12 to be cleaned at 550. The worker 416 identification bar code indicia 420 must also be scanned and the dispensing computer 400 verifies the worker is allowed to clean the identified cell and may access all cells in the dispensing drawer 14 at 552. At 554, electronic drawer locking mechanism may be actuated by the worker pressing the drawer release switch 386 to unlock the dispensing drawer 14 containing the dispensing device 12 and dispensing cell 16. The drawer controller 46 and cabinet controller 18 monitor the dispensing device switch 66 to verify the worker removes the correct dispensing device 12 from the dispensing cell 16 and the drawer position switch 388 to verify when the drawer is closed.

After the dispensing device and or dispensing cell have has been cleaned, or other maintenance performed, the pharmacy worker 416 must initiate the dispensing device insertion procedure on the dispensing computer 400, cordless bar code scanner 294 or handheld computer or handheld computer which incorporates a bar code scanning device 296. The worker will be directed through the proper steps required to return a removable dispensing device 12 to a dispensing cell 16. The dispensing cell must be identified by scanning the dispensing cell bar code indicia 44 and then the worker identified by scanning his indicia 420. The dispensing computer 400 verifies the worker is allowed to return a dispensing device 12 to the dispensing cell 16 and can access any cell 16 within the dispensing drawer 14. The electronic drawer locking mechanism may be actuated by the worker pressing the drawer release switch 386 to unlock the dispensing drawer 14 containing the dispensing device 12 and dispensing cell 16. The drawer controller 46 and cabinet controller 18 monitor the dispensing device switch 66 to verify the worker inserts the dispensing device into the correct dispensing cell. When the dispensing device is inserted into the dispensing cell, the dispensing cell tab 70 actuates the dispensing device switch 66. The drawer controller 46, cabinet controller 18, and dispensing computer 400 monitor the drawer position switch 388 to indicate the drawer has been closed and the dispensing device insertion procedure completed. Once the dispensing device has been correctly inserted, the worker may indicate to the dispensing computer the cleaning process was completed which resets the quantity dispensed and number of days between cleaning intervals.

The present invention thus includes a pharmacy medicament filling system utilizing the medicament dispensing cabinet 10, dispensing device 12, and prescription 292 or medicament 293 bar codes from a patient prescription label sheet 291 to initiate, direct, record and verify each patient prescription filled in the pharmacy. Referring to FIG. 42, the filling workstation 402 can receive orders for patient prescriptions via an electronic interface connected to the pharmacy computer system or via a bar code scanner (422, 294, or 296) in communication with the filling workstation 402. The pharmacy worker 416 can initiate the dispensing of a patient prescription by scanning the patient prescription label bar code 292 (See FIG. 37), scanning the dispensing cell label bar code 44 (see FIG. 2A), or selecting the proper command on an input device of a control device. When the pharmacy worker initiates the filling of a patient prescription by scanning the patient prescription label bar code 292, the filling workstation 402 may decode the data value into two components; the first component being a drug number which is associated with a dispensing cell 16 by, e.g., the dispensing computer 400, and the second component representing the quantity of medicament 62 desired. When the pharmacy worker 416 initiates a patient prescription by scanning the dispensing cell bar code label 44, the pharmacy worker 416 would be required to enter the quantity into the cordless bar code reader 294 or handheld computer or handheld computer which incorporates a bar code scanning device 296 as indicated on the patient's prescription label sheet 291.

The cordless bar code reader 294 or handheld computer or handheld computer which incorporates a bar code scanning device 296 provide the worker complete mobility while performing the tasks of filling a patient prescription, replenishing a dispensing cell, and removing or inserting a removable dispensing device. The dispensing computer 400 receives the specific bar code indicia values of the dispensing cell 16 to insure the worker is physically positioned in front of the dispensing cell 16 to prevent errors from being introduced into a patient prescription. The cordless bar code reader 294 or handheld computer which incorporates a bar code scanning device 296 also allows the pharmacy worker to fill patient prescriptions using non-automated medicament dispensers with similar verification and monitoring steps while providing the mobility to perform these filling tasks throughout the pharmacy and at the pharmacy worker's convenience. The worker is provided access to patient prescription data from the dispensing computer 400 while operating anywhere within the pharmacy. This mobile access improves the efficiency of the pharmacy worker while decreasing the time needed to fill each prescription, and also reducing the potential for errors.

Regardless of the method used to initiate the filling of a patient prescription, the pharmacy worker identification must be provided to the dispensing computer 400 e.g., by using a bar code reader (422, 294 or 296) to scan the pharmacy worker's identification badge 418. The dispensing computer 400 will verify the pharmacy worker 416 has authorization to operate and dispense medicament 62 from the medicament dispensing cabinet 10. If the worker fails to retrieve the medicament 62 from the dispensing cell 16 within a prescribed time, the worker will be required to re-initiate the secure pick up procedure. When the worker identification bar code indicia 420 is scanned and input to the dispensing computer 400 to initiate retrieval of the patient prescription, the worker must retrieve the medicament from the dispensing cell's chute 32 before another retrieval is initiated by the worker or another worker. This insures that only one dispensing cell's gate release 36 is activated at a time preventing incorrect medicament dispensing. However, if a worker is physically in front of a cell, and the cell's bar code indicia 44 is scanned and input to the dispensing computer to initiate retrieval of the patient prescription, multiple dispensing cell gate releases 36 may be activated at a time because the workers are physically close to the dispensing cell 16, preventing incorrect medicament dispensing.

Some medicaments, such as narcotic or controlled substance medicaments, may have further handling restrictions requiring a secondary security check to be made by the dispensing computer 400 to insure the pharmacy worker 416 may dispense, replenish or maintain these medicaments. As discussed in conjunction with FIG. 41, the dispensing computer 400, or other computer within the pharmacy network, maintains a database of pharmacy workers and their security level. In addition, the database of pharmacy workers includes such fields as the pharmacy worker's name, initials, password, identification badge bar code indicia 420, security authorization level for dispensing, replenishment, access to normal medicament, and access to narcotic or controlled medicament, among others.

Figure 48:
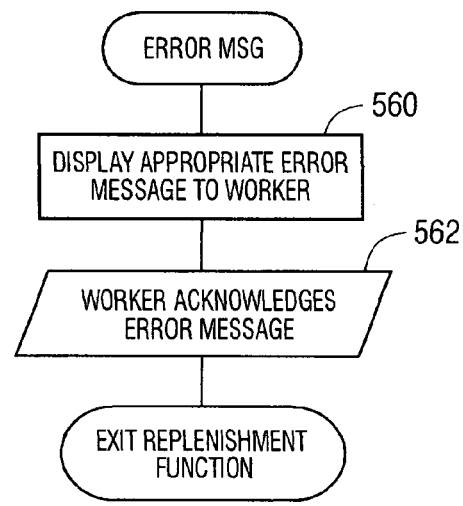
FIG. 48 is a flow chart illustrating an error message routine.

FIG. 48 is a flow chart illustrating an error message routine. The error message routine illustrated in FIG. 48 may be called in connection with any of the procedures previously discussed which requires the generation of an error message. As shown in FIG. 48, the error message is displayed at 560 followed by an acknowledgement by the worker at 562. Thereafter, the routine illustrated in FIG. 48 is exited.

While the present invention has been described in connection with preferred embodiments thereof, those of ordinary skill in the art will recognize that many modifications and variations are possible. For example, it is anticipated that by providing one or more switches on each dispensing cell 16, the dispensing cabinet 10 may be placed in a bypass mode. Using the switches, a number can be input to a dispensing cell which then operates to dispense the quantity of medicament manually set by the user via the switch. Another example of a modification is to use the cycle count procedure of block 546 of FIG. 46B in a pre-pack mode. Pre-pack, as the term implies, involves a situation where a pharmacy knows that it is going to sell a particular drug in a particular count. As a result, vials with that drug and that count are filled ahead of having a prescription for them such that when a prescription is received, the "pre-pack" need only be labeled. The cycle count would be modified so that the dispensing cabinet 10 is informed that the medicament is being removed, and will not be replaced after the cycle count. Another variation involves modifying the secure pick up procedure so as to be used with other dispensing devices. For example, if the dispensing device is a Baker cell, the user scans the cell's location, at which time the controller dispenses, the pills. The user then retrieves the pills and scans her ID if security requires such a scan. The difference in the procedures is that the dispensing does not take place until the dispensing location has been scanned by the user, meaning that the user is at the correct location. Such modified procedures are also applicable to RxPorts. The present invention is intended to be limited only by the following claims and not by the foregoing description which is intended to be exemplary and not limiting.

What is claimed is:

1. A method, comprising:
   dispensing an amount of medicament into a chute;
   inputting information identifying a person requesting access to the dispensed medicament after the medicament has been dispensed into the chute;
   determining if said person requesting access has authority to pick up the dispensed medicament; and
   selectively permitting access to the dispensed medicament in the chute in response directly to said determining.

2. The method of claim 1 wherein said determining includes determining if the person requesting access is the same as a person initiating the dispensing or if the person requesting access has authority to pick up medicament for the person initiating the dispensing.

3. The method of claim 1 additionally comprising inputting information identifying a person picking up the dispensed medicament after the medicament has been picked up.

4. The method of claim 1 additionally comprising inputting information identifying the dispenser which has performed said dispensing.

5. A method, comprising:
   identifying a dispenser which requires service;
   inputting user information;
   determining if said user has authority to access all dispensers in a drawer carrying the dispenser requiring service and, if so:
   issuing an unlock command for the drawer carrying the dispenser requiring service;
   awaiting receipt of a signal from a drawer unlock switch;
   monitoring a dispensing device switch to insure that the dispenser requiring service is the dispenser removed; and monitoring a drawer position switch to determine when said drawer is closed.

6. The method of claim 5 wherein said service includes one of cleaning, stocking, and maintenance.

7. A method, comprising:
- identifying a dispenser which requires insertion into a drawer;
- inputting user information;
- determining if said user has authority to access all dispensers in the drawer into which the dispenser is to be inserted and, if so:
- issuing an unlock command for the drawer;
- awaiting receipt of a signal from a drawer unlock switch;
- monitoring a dispensing device switch to insure that the dispenser is inserted into the proper position; and
- monitoring a drawer position switch to determine when said drawer is closed.

8. A method of claim 1 wherein selectively permitting access comprises selectively releasing a chute gate in response to said determining.

* * * * *